US011318107B2

(12) United States Patent
Vasisht et al.

(10) Patent No.: US 11,318,107 B2
(45) Date of Patent: *May 3, 2022

(54) PHARMACEUTICAL ACTIVE-CONTAINING FILM DELIVERY DEVICE FOR ORAL TRANSMUCOSAL ADMINISTRATION

(71) Applicant: Avior, Inc., Cary, NC (US)

(72) Inventors: Niraj Vasisht, Cary, NC (US); Karl D. Kelly, Holly Springs, NC (US)

(73) Assignee: Avior, Inc., Cary, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/999,192

(22) Filed: Aug. 21, 2020

(65) Prior Publication Data
US 2021/0030693 A1     Feb. 4, 2021

Related U.S. Application Data

(63) Continuation-in-part of application No. PCT/US2019/019150, filed on Feb. 22, 2019.

(60) Provisional application No. 62/890,346, filed on Aug. 22, 2019.

(51) Int. Cl.
    *A61K 9/16*        (2006.01)
    *A61K 9/50*        (2006.01)
    *A61K 9/70*        (2006.01)
    *A61K 31/485*     (2006.01)

(52) U.S. Cl.
    CPC .............. *A61K 9/7007* (2013.01); *A61K 9/16* (2013.01); *A61K 9/50* (2013.01); *A61K 31/485* (2013.01)

(58) Field of Classification Search
None
See application file for complete search history.

(56) References Cited

U.S. PATENT DOCUMENTS

| | | | |
|---|---|---|---|
| 6,881,745 | B2 | 4/2005 | Hayes et al. |
| 9,265,760 | B2 | 2/2016 | Hartman et al. |
| 9,339,499 | B2 | 5/2016 | Hartman et al. |
| 9,901,545 | B1 | 2/2018 | Fuisz et al. |

(Continued)

FOREIGN PATENT DOCUMENTS

EP     1462095 A1     9/2004

OTHER PUBLICATIONS

Alpha-tocopheryl acetate [online] retrieved on Feb. 16, 2021 from: http://www.saapedia.org/en/saa/?type=detail&id=5910; 5 pages) (Year: 2021).*

(Continued)

*Primary Examiner* — Ernst V Arnold
(74) *Attorney, Agent, or Firm* — NK Patent Law

(57) ABSTRACT

A transmucosal delivery device comprises a polymer film comprising a polymer matrix, and a pharmaceutical composition disposed on a surface of the polymer film, the composition comprising at least one pharmaceutical active, a binding polymer, a surfactant, a solubilizing solvent, and an anti-crystallization agent, wherein a dry concentration of the pharmaceutical active is greater than 10 wt % and the composition has a pH in a range of about 4 to about 8. The delivery device exhibits a residence time in the mouth of a subject ranging from about 5 minutes to about 15 minutes and is substantially mucoadhesive to a mucosal surface when placed sublingually under the tongue or placed buccally at the inner lining of the cheek of the subject.

19 Claims, 18 Drawing Sheets

(56) References Cited

U.S. PATENT DOCUMENTS

| | | |
|---|---|---|
| 10,195,142 B2 | 2/2019 | Fuisz et al. |
| 10,238,600 B2 | 3/2019 | Fuisz et al. |
| 2008/0260807 A1 | 10/2008 | Sharp et al. |
| 2011/0129533 A1 | 6/2011 | Straub et al. |
| 2011/0262522 A1 | 10/2011 | Finn et al. |
| 2012/0009260 A1 | 1/2012 | Schobel et al. |
| 2012/0164191 A1 | 6/2012 | Finn et al. |
| 2013/0045268 A1 | 2/2013 | Finn et al. |
| 2014/0008831 A1 | 1/2014 | Yang et al. |
| 2014/0271867 A1 | 9/2014 | Myers |
| 2016/0235769 A1 | 8/2016 | Hill |
| 2017/0136078 A1 | 5/2017 | Li et al. |
| 2021/0085622 A1* | 3/2021 | Vasisht ............... A61K 9/7007 |

OTHER PUBLICATIONS

Hennequin et al. (Urol Res 1993;21:101-108). (Year: 1993).*
ISA/US; International Search Report and Written Opinion for International Patent Application No. PCT/US2019/019150 dated May 31, 2019, 21 pages.
EPO; Extended European Search Report for European Patent Application No. 19757114.4 dated Apr. 19, 2021, 9 pages.
EPO; Communication pursuant to Rules 70(2) and 70a(2) EPC for European Patent Application No. 19757114.4 dated May 7, 2021, 1 page.
USPTO; Non-Final Office Action for U.S. Appl. No. 16/971,339 dated Nov. 1, 2021, 11 pages.
IPO; Office Action for Indian Patent Application No. 202017039167 dated Mar. 1, 2022, 6 pages.

* cited by examiner 4 mg 2 mg 4 mg

PHARMACEUTICAL ACTIVE-CONTAINING FILM DELIVERY DEVICE FOR ORAL TRANSMUCOSAL ADMINISTRATION

CROSS REFERENCE TO RELATED APPLICATIONS

This application is a continuation in part of International Application No. PCT/US19/19150, filed Feb. 22, 2019. This application also claims priority to U.S. Provisional Application No. 62/890,346, filed Aug. 22, 2019. The entire contents of each of which are incorporated herein by reference.

TECHNICAL FIELD

The presently disclosed subject matter relates to a pharmaceutical active-containing film delivery device configured for oral transmucosal administration, a method of manufacturing the delivery device and methods of treatment using the delivery device. The disclosed subject matter includes pharmaceutical compositions comprising nalmefene that can be administered buccally or sublingually to a subject in need of treatment.

BACKGROUND

The United States is experiencing a growing opioid epidemic. More than 47,000 Americans died of opioid overdose in 2017 alone. There were approximately 10.3 million people aged 12 years and older in the United States in 2018 who misused opioids, including heroin. A Government Accountability Office report released in October 2018 declared the opioid crisis a public health emergency. According to the CDC, more than 31,000 deaths involving synthetic opioids (other than methadone) occurred in the United States in 2018. Synthetic opioid-involved death rates increased by 10% from 2017 to 2018 and accounted for 67% of opioid-involved deaths in 2018.

With the emergence of carfentanil-laced heroin, the number of opioid overdose-related deaths has significantly increased. As such, more potent and longer-acting opioid antagonists are critically needed.

Nalmefene is a µ-opioid receptor (MOR) antagonist and partial kappa-opioid receptor (KOR) agonist approved for use in the United States as an antidote for opioid overdose. Nalmefene is an opiate derivative similar in both structure and activity to the opioid antagonist naltrexone. However, nalmefene has a longer elimination half-life and greater oral bioavailability than naltrexone. The longer elimination half-life eliminates the need for repeat dosing in the event of an accidental overdose of a long-acting opioid. Nalmefene also has stronger receptor binding than naloxone. Naloxone is a medication currently being used to rapidly reverse opioid overdose. Naloxone can quickly restore normal respiration to a person whose breathing has slowed or stopped as a result of overdosing with heroin or prescription opioid pain medications. However, heroin and other highly addictive drugs are increasingly being laced with fentanyl and carfentanil, and naloxone has a limited ability to effectively control carfentanil related overdose. Thus, a need exists for a composition configured to rapidly deliver a therapeutically effective amount of an active ingredient for treating and controlling all opioid-related overdoses.

Apart from its utility in antagonizing the sedation, respiratory depression, and other actions of opioid agents, nalmefene has also been found useful in treating diverse conditions such as hyperkinesia in children, senile dementia, and sudden infant death syndrome, among others. Oral administration of nalmefene has also been shown to be safe and effective for use in treating alcohol dependence.

Nalmefene can also be used to treat chronic liver and kidney disease-associated pruritus, as well as pruritus associated to atopic dermatitis and/or prurigo nodularis. The term "pruritus" refers to an intense sensation of itching, commonly associated with chronic liver and kidney disease. Intermittent moderate-to-severe-pruritus (itch) is a common comorbid symptom of chronic liver diseases such as primary biliary cholangitis (PBC), primary sclerosing cholangitis (PSC), alcoholic liver disease (ALD), fatty liver disease (FLD), hepatitis (B/C), and liver cirrhosis. It is estimated that over 2.5 million patients suffer from intractable, persistent pruritus in liver disease patients with no FDA approved therapies currently available. Pruritus in liver disease is a refractory symptom and it reduces the patients' quality of life (QOL) causing insomnia, anxiety, depression, nocturnal scratching, excoriation, and bleeding. Pruritus occurs in patients with end-stage renal disease (ESRD, Stages III to V) and patients with hemodialysis. There are over 1.6 million patients suffering from moderate to severe pruritus from Stage III to V ESRD and almost 550,000 patients suffering from pruritus manifested from their hemodialysis. If mild cases were included, approximately 4.1 million patients in the United States suffer from pruritus associated with chronic kidney disease.

The disease state is also common in atopic dermatitis (eczema) where 91% of the 15.6 million patients experience pruritus. However, despite new therapies to treat atopic dermatitis, approximately 31% do not find relief for their pruritus. The presence of pruritus has been associated with poor quality of life, inadequate sleep, depression, and up to 37% higher adjusted mortality risk than patients with mild or no pruritus. In addition, patients often develop prurigo nodularis, a skin disease characterized by inflamed, scaly, and excoriated nodules and lesions. While the mild form of pruritus and prurigo nodularis is commonly treated with corticosteroids and antihistamines, such drugs are relatively ineffective in moderate and/or severe forms of chronic pruritus in both cholestatic (liver) and uremic (kidney) patients. As a result, clinicians commonly use a variety of medications for treatment such as cholestyramine for liver disease associated pruritus and gabapentin for kidney disease associated pruritus.

Since there are no approved products in the United States to treat chronic liver and kidney disease-associated pruritus, or prurigo nodularis, there is a dire unmet need towards development of a treatment for this morbidity condition.

Lastly, according to a National Survey on Drug Use and Health (NSDUH) 2015 report, 15.1 million adults ages 18 and older had alcohol use disorder (AUD). About 1.3 million adults received treatment for AUD at a specialized facility. The prevalence of binge drinking and heavy alcohol use has been increasing. In 2015, 26.9 percent of people ages 18 or older reported that they engaged in binge drinking in the past month, of which 7.0 percent reported that they engaged in heavy alcohol use in the past month. Alcohol misuse in the United States costs a staggering $249.0 billion (2010 statistics) and results in an estimated 88,000 deaths from alcohol-related causes annually, making alcohol the fourth leading preventable cause of death in the United States. The problem world-wide is even worse, where 3.3 million deaths (2012 statistics) occurred.

Nalmefene can be used for the treatment of alcohol dependence. Unlike other treatments for this disease, it can be taken on an 'as needed' basis to reduce the desire to drink, thus offering patients a novel treatment option compared to traditional methods, which are aimed at total abstinence and usually include intensive psychosocial therapy. U.S. Pat. No. 5,086,058 describes the use nalmefene in treating alcoholism.

Oral thin films can provide a convenient way to administer pharmaceutical actives to a subject in need thereof. This administration route is particularly relevant when the film product can provide transmucosal delivery to avoid first pass metabolism from the impaired liver, or impaired kidney which will need to excrete these metabolites. Current, commercially available films suffer from drawbacks. For example, current films, designed as fast dissolving oral films often have poor transmucosal delivery, which limits high dose strengths and results in low oral bioavailability. Particularly, available films may dissolve upon contact with saliva leading to the pharmaceutical active being swallowed and entering the gastrointestinal system. Thus, these films do not provide fast onset of drug action, do not have high bioavailability and have higher metabolites in the plasma. In addition, commercially-available films have incorporated pastes as film protectants and as drug delivery systems. However, the film-forming behavior and bioadhesion of such pastes do not last and the product exhibits a limited residence time. Further, commercially-available films that include multiple layers (such as BEMA® film technology) are difficult to manufacture and are more expensive to manufacture compared to single layered films. The fabrication time for multi-layered products is relatively long and is coupled with critical need for thickness control to maintain content uniformity for the underlying layers. Additionally, and importantly, none of the available multi-layered technologies offer the opportunity to load high dose strengths, high concentration and high bioavailability concurrently or individually, as available with the delivery device described herein.

A composition configured for delivery of an active ingredient to treat opioid overdose, pruritus, or other conditions using an improved film device that addresses the shortcomings in the prior art is desirable.

SUMMARY

In a first aspect of the invention, a transmucosal delivery device comprises a polymer film comprising a polymer matrix, and a pharmaceutical composition disposed on a surface of the polymer film. The composition comprises at least one pharmaceutical active, a binding polymer, a surfactant, a solubilizing solvent, and an anti-crystallization agent. A dry concentration of the pharmaceutical active is greater than 10 wt % and the composition has a pH in a range of about 4 to about 8. The delivery device exhibits a residence time in the mouth of a subject ranging from about 5 minutes to about 15 minutes and is substantially mucoadhesive to a mucosal surface when placed sublingually under the tongue or placed buccally at the inner lining of the cheek of the subject.

In a second aspect of the invention, a method of manufacturing a pharmaceutical active-containing transmucosal delivery device comprises blending a polymer matrix and a pH adjusting agent; solubilizing the blend; casting the blend into a polymer film; applying a pharmaceutical active composition onto a surface of the polymer film, wherein a viscosity of the composition is from about 1 cP to about 400 cP; heating and drying the polymer film with the pharmaceutical active composition applied thereto, and converting the heated and dried film with the pharmaceutical active composition applied thereto into individual unit doses thereby forming a pharmaceutical active-containing transmucosal delivery device.

In a third aspect of the invention, a method for treating or aiding in treating opioid overdose in a subject in need of such treatment comprises transmucosally administering to the subject a transmucosal delivery device comprising nalmefene.

In a fourth aspect of the invention, a method of treating pruritus in a subject in need of such treatment comprises transmucosally administering to the subject a transmucosal delivery device comprising nalmefene.

BRIEF DESCRIPTION OF THE DRAWINGS

The previous summary and the following detailed descriptions are to be read in view of the drawings, which illustrate some (but not all) embodiments of the presently disclosed subject matter.

DETAILED DESCRIPTION

Figure 1:
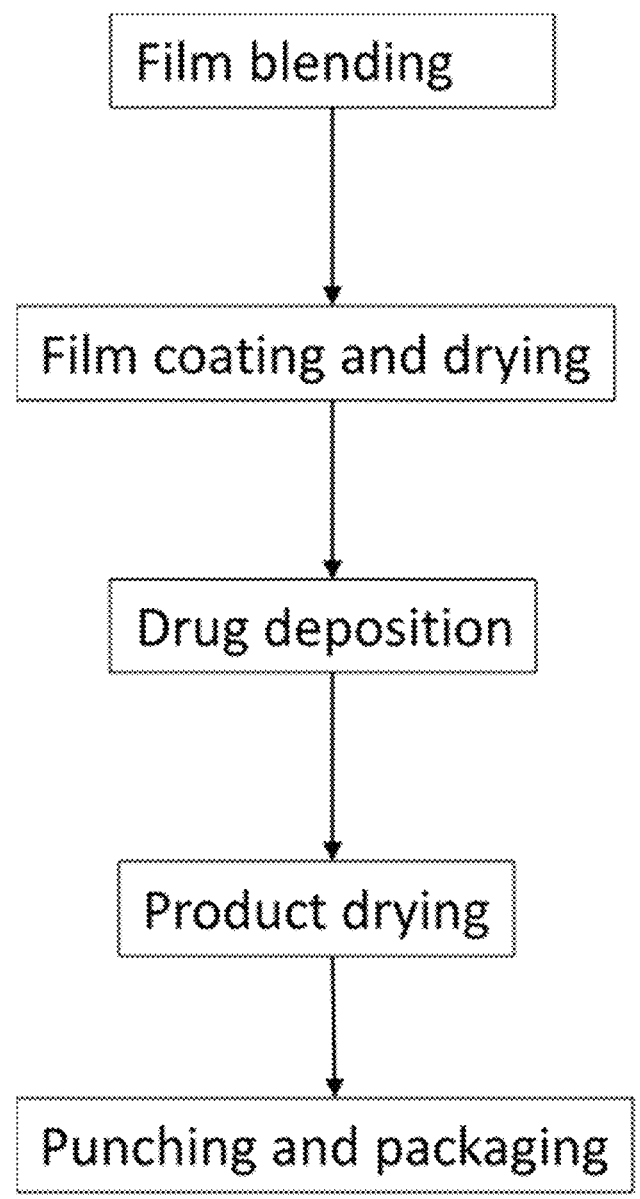
FIG. 1 is a schematic flow diagram of an exemplary manufacturing process.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a film" can include a plurality of such films, and so forth.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, linear-dimension, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

Described herein is a method of treating or aiding in treatment of rescue from opioid overdose, maintenance therapy for opioid dependence patients, treatment of moderate to severe pruritus, alcoholism, gambling addiction, and obsessive-compulsive disorder with a pharmaceutical composition. The methods described herein may also be used for treating or aiding in treating numerous conditions, including rescue treatment, such as, for example, epilepsy, seizure, anaphylactic shock, or other rescue type situations. Additionally, a person having ordinary skill in the art will understand that the pharmaceutical active-containing film delivery device described herein can be used for treating or aiding in treating any condition, disease, disorder, etc. that is amenable for treatment using a film delivery device configured for oral transmucosal administration. The method of treatment includes transmucosally administering (e.g., across a mucosal tissue, such as buccal and/or sublingual tissues) a pharmaceutical active composition to a subject in need thereof. Additionally, described herein is a method of treating chronic liver and chronic kidney disease-associated pruritus by transmucosally administering (e.g., across a mucosal tissue, such as buccal and/or sublingual tissues) a pharmaceutical active composition to a subject in need thereof.

The method of treatment described herein involves administering a pharmaceutical active composition via transmucosal administration. The composition comprises or consists essentially of an active ingredient. The composition may also include an anticrystallization agent, a binding polymer, a pH adjusting or buffering agent, a surfactant, and a solubilizing solvent. In an embodiment, the pharmaceutical composition comprises nalmefene as an active ingredient. In this embodiment, advantageously, in vivo, a dosage unit of the pharmaceutical composition provides a mean plasma concentration of nalmefene of at least 1 ng/ml, within 10 minutes after administration.

Also described herein is a method of manufacturing the pharmaceutical active-containing transmucosal delivery device involving spray or dropwise deposition of the pharmaceutical active composition. In an embodiment using dropwise deposition, a fixed amount or volume of a pharmaceutical active ingredient can be placed on the surface of a polymer film. The dropwise method enables discrete, constant volume deposition of the pharmaceutical active composition at a high degree of precision without loss of the same to the environment during deposition (versus spraying, for example). In embodiments, the composition is in the liquid phase and comprises a pharmaceutical active ingredient dissolved in a solvent or dispersed in a continuous phase. The composition has a concentration of pharmaceutical active ingredient that can be chosen based on intended end use or application. In embodiments, the concentration of the active ingredient is relatively high in comparison to other conventional film-based dosage forms, gels, creams, lotions or even tablets. The amount or volume of liquid composition deposited in droplet form can be precisely controlled using available deposition technologies. For example, a constant volume extruding system or a precision liquid flow-controlled system can be used to meter and control droplet volume.

Moreover, the size of the needle used for droplet deposition impacts the size of the drop deposited and the number of drops needed for a particular dose strength. The needle gauge diameter influences the size of the droplet deposited, and hence impacts the drug assay. In an embodiment, the needle gauge may vary from about 6G to about 24G. In another embodiment, the needle gauge may be between about 8G and about 14G. In a further embodiment, the needle may be between about 8G and about 10G.

The flow rate of the pharmaceutical composition may range from about 0.1 mL/min to about 20 mL/min per nozzle. As the number of nozzles increase, the production rate of manufacturing increases in proportion.

The treatment method comprises transmucosally administering a pharmaceutical composition containing an active ingredient to a subject in need of such treatment. In embodiments, the pharmaceutical composition comprises nalmefene as an active ingredient. In embodiments, the pharmaceutical composition may include one or more compounds other than nalmefene as alternative active ingredients or may include one or more compounds in addition to nalmefene as additional active ingredients.

In some embodiments, the pharmaceutical composition can comprise about 1 to about 32 mg of alternative or additional active ingredient. Thus, the alternative or additional active agent (or subsequent active agents) can be present in an amount of about 0.05 to about 24 mg, preferably of about 0.1 to about 16 mg, or most preferably between about 0.25 to about 8 mg.

The alternative or additional active ingredients may include, but not be limited to, an ace inhibitor (such as Benazepril, Captopril, Enalapril, Lisinopril, Moxepril, Perindopril, Quinapril, Ramipril and/or Trandolapril), addiction medicine (such as buprenorphine, disulfiram, naltrexone, cannabidiol, nalfurafine, and/or varenicline), alpha-1 adrenergic blockers (such as alfuzosin, doxazosin, prazosin, tamsulosin and/or terazosin), ALS agents (such as riluzole), Alzheimer's disease medications (such as donepezil, galantamine, rivastigmine, and/or memantine), allergy, antipyretic and antibiotics medications (such as allopurinol, azelastine, beclomethasone, budesonide, desmopressin, fluticasone, phenylephrine, barbiturates, metronidazole, carbamazepine, cimetidine, ibuprofen, penicillins, amoxicillin, cloxacillin, dicloxacillin, ticarcillin, phenyloin, quinidine, streptomycin and/or vancomycin), analgesics and anesthetics (such as ketamine, pentozocine, propofol, fentanyl, buprenorphine, oxycodone, hydrocodone, and/or nalbuphine); amlexanox, benzocaine, carbamide, peroxide, nystatin, lidocaine, and/or pilocarpine), angiotensin II receptor blockers (such as candesartan, eprosartan mesylate, olmesartan, telmisartan, and/or valsartan), anti-arrhythmics (such as adenosine, amiodarone, atropine, epinephrine, mexiletine, moricizine, procainamide, propafenone, quinidine, sotalol, and/or verapamil), antispasmotic and anticholinergics (such as hyoscyamine, scopolamine, darifenacin, oxybutynin, solifenacin, tolterodine, glycopyrrolate, hyoscyamine, oxybutynin, propantheline, scopolamine, promethazine, flavoxate, trospium, and/or tolterodine), anticonvulsants (such as carbamazepine, clonazepam, diazepam, ethosuximide, felbamate, pregabalin, levetiracetam, lamotrigine, lorazepam, midazolam, oxcarbazepine, phenobarbital, tiagabine, topiramate, and/or valproic acid), antidepressants (such as asenapine, buprorion, buprenorphine, citalopram, desipramine, doxepin, duloxetine, escitalopram, fluoxetine, fluvoxamine, imipramine, mirtazapine, nefazodone, nortriptyline, nortriptyline, sertraline, trazodone, and/or venlafaxine), anti-diarrheals (such as diphenoxylate, atropine, loparimide, and/or bismuth subsalicylate), anti-diabetic agents (such as acarbose, miglitol, and metformin, Avandamet®, glucovance, metaglip, metaglip, rosiglitazone, osiglitazone, repaglinide, chlorpropamide, glimepiride, glyburide, glipizide, tolazamide, tolbutamide, glucagon, extenatide, and/or pramlintide), antibodies and immunological drugs (such as adalimumab, anakinra, alitretinoin, becaplermin, calamine, doxepin, fluorouracil, masoprocol, pimecrolimus, tacrolimus, auranofin, azathioprine, etanercept, hydroxychloroquine, infliximab, leflunomide, methotrexate, and/or sulfasalazine), anti-emetics (such as aprepitant, dolasetron, droperidol, granisetron, metoclopramide, ondansetron, prochlorperazine, scopolamine, promethazine, and/or trimethobenzamide), antifungals (such as amphotericin B, anidulafungin, caspofungin, clotrimazole fluconazole, flucytosine, griseofulvin, itraconazole, ketoconazole, micafungin, nystatin, posaconazole, terbinafine, voriconazole, butenafine, ciclopirox, clotrimazole, enconazole, ketoconazole, miconazole, naftifine, nystatin, oxiconazole terbinafine, butenafine, ciclopirox, clotrimazole, econazole, ketoconazole, miconazole, naftifine, nystatin, oxiconazole, terbinafine clindamycin, metronidazole, butoconazole, clotrimazole, miconazole, terconazole and tioconazole, and/or tolnaftate), anti-hepatitis (such as adefovir, entecavir, lamivudine, peginterferon alfa-2a, peginterferon alfa-2b, rebetron, and/or ribavirin), anti-herpetic agents (such as acyclovir, famciclovir, valacyclovir, acyclovir, docosanol, and/or penciclovir), antihistamines (such as cetirizine, desloratadine, fexofenadine, loratadine, chlorpheniramine, clemastine, cyproheptadine, dimenhydrinate, diphenhydramine, and/or hydroxyzine), anti-hypertension (such as benazepril, captopril, enalapril, lisinopril, moexipril, losartan, valsartan, atenolol & chlorthalidone, bisoprolol, metoprolol, nadolol & bendroflumethazide, propranolol, timolol, amlodipine & benazepril, verapamil & trandolapril, amiloride, spironolactone, triamterene, clonidine, hydralazine, methyl-dopa, and/or prazosin & polythiazide), anti-hypertensives (such as aliskiren, aliskiren, eproprostenol, fenoldopam, hydralazine, minoxidil, nitroprusside, phentolamine, and/or treprostinil), anti-influenza agents (such as oseltamivir phosphate, rimantadine and/or zanamivir), anti-malarials, anti-protozoals, amebicides (such as atovaquone, chloroquine, Iodoquinol, mefloquine, primaquine, pyrimethamine, pyrimethamine, pyruvium, sulfadoxine, and/or quinine), anti-platelet agents (such as abciximab, dipyridamole/ASA, anagrelide, cilostazol, clopidogrel, dipyridamole, eptifabatide, ticlopidine, and/or tirofiban), antipsychotics (such as aripiprazole, chlorpromazine, clozapine, fluphenazine, haloperidol, loxapine, molindone, amantadine, rimantadine, and memantine, olanzepine, perphenazine, pimozide, quetiapine, risperidone, thioridazine, thiothixine, trifluoperazine, ziprasidone, and/or lithium), antispasmotics (such as dicyclomine, donnatal extentabs, propantheline, simethicone, hyoscyamine, Librax, tegaserod, baclofen, carisprodol, cyclobenzaprine, cyclobenzaprine, diazepam, metaxalone, orphenadrine, and/or bellergal-S), anti-herpetic agents (such as acyclovir, famciclovir, valacyclovir, docosanol, and/or penciclovir), anti-hypertensives (such as captopril, clonidine, enalaprilat, esmolol, fenoldopam mesylate, hydralazine, labetalol, nicardipine, and/or nitroglycerin), anti-tussives/expectorants (such as benzonatate and/or guaifenesin), atopic dermatitis medications (such as pimecrolimus and/or tacrolimus), anti-anxiolytic agents (such as benzodiazepines and non-benzodiazepine sedatives like alprazolam, buspirone, chlordiazepoxide, chlorazepate, clonazepam, diazepam, estazolam, eszcpiclone, flurazepam, imidazenil, lorazepam, midazolam, oxazepam, rameteon, temazepam, triazolam, zaleplon and zolpidem; beta blockers, such as atenolol, betaxolol, bisoprolol, carvedilol, esmolol, labetalol, metoprolol, nadolol, pindolol, propranolol, sotalol, and/or timolol), bile acid sequestrants (such as cholestyramine, colesevelam, and/or colestipol), bisphosphonates (such as alendronate, etidronate, pamidronate, risedronate, tiludronate and zoledronic acid, raloxifene, and/or teriparatide), benign prostatic hypertrophy medications (such as alfuzosin, doxazosin, dutasteride, finasteride, tamsulosin, and/or terazosin), calcium channel blockers (such as amlodipine, bepridil, diltiazem, felodipine, isradipine, nicardipine, nifedipine, and/or nisoldipine), cephalosporins (such as cefadroxil, cefazolin, cephradine, cephalexin, cefaclor, cefotetan, cefoxitin, cefprozil, cefuroxime, cefuroxime, loracarbef, cefdinir, cefixime, cefoperazone, cefotaxime, cefpodoxime, ceftazidime, ceftibuten, ceftizoxime, and/or cefepime), colony stimulating factors (such as darbepoietin alfa, erythropoietin, filgrastim, oprelvekin, pegfilgrastim, and/or sargramostim), corticosteroids (such as budesonide, cortisone acetate, dexamethasone, fludrocortisones, hydrocortisone, methylprednisolone and prednisone, Medrol®, aclometasone dipropionate, desonide, flucinolone acetonide, Hydrocortisone, betamethasone dipropionate, betamethasone valerate, clocortolone pivalate, desoximetasone, fluocinolone acetonide, flurandrenolide, fluticasone propionate, chydrocortisone butyrate, hydrocortisone valerate, mometasone furoate, prednicarbate, triamcinolone, amcinonide, augmented betamethasone dipropionate, betamethasone dipropionate, desoximetasone, diflorasone diacetate, fluocinolone acetonide, fluocinonide, halcinonide, clobetasol propionate, diflorasone diacetate and halobetasol propionate, and/or triamcinolone acetonide), decongestants (such as phenylephrine and/or pseudoephedrine), diuretics (such as acetazolamide, amiloride, amiloride and HCTZ bendroflumethiazide, bumetanide, chlorothiazide, chlorthalidone, dichlorphenamide, eplenerone, ethacrynic acid, furosemide, hydrochlorothiazide, HCTZ/triampterene, hydroflumethiazide, indapamide, methazolamide, methyclothiazide, methyclothiazide, metolazone, polythiazide, spironolactone, spironolactone, HCTZ torsemide, trichlormethiazide, and/or triamterene), endocrine agents (such as bromoc cinacalcet cosyntropin, riptine, cabergoline, calcitonin, desmopressin, Leuprolide, octreotide, and/or vasopressin), erectile dysfunction agents (such as sildenafil, tadalafil, and/or vardenafil), fibrates (such as clofibrate, fenofibrate, and/or gemfibrozil), fluoroquinolones (such as ciprofloxacin, gatifloxacin, levofloxacin, moxifloxacin, norfloxacin, and/or ofloxacin), gastrointestinal agents (such as alosetron, infliximab, mesalamine, misoprostol, neomycin, octreotidev, osalazine, orlistat, sucralafate, vasopressinallopurinol, colchicine, probenecid, cimetidine, famotidine, nizatidine, ranitidine, balsalazide, budesonide, infliximab, mesalamine, olsalazine, and/or sulfasalazine), Interferon (such as Interferon alfa-2A, Interferon alfa-2b, Interferon alfa-2b and ribavirin combo pack, Interferon alfa-N3, Interferon beta-1A, Interferon beta-1B (Betaseron®), cilostazol, and/or pentoxifylline), immunizations (such as Comvax, diphtheria-tetanus toxoid, hepatitis A vaccine, hepatitis B vaccine, influenza vaccine, Fluzone, lyme disease vaccine, and/or PNEUMOVAX® 23), heparins (such as dalteparin, danaparoid, enoxaparin, tinzaparin, and/or fondaparinux) macrolides (such as azithromycin, clarithromycin, and/or erythromycin), migraine medication (such as almotriptan, eletriptan, frovatriptan, naratriptan, rizatriptan, sumatriptan, zolmitriptan, and/or dihydroergotamine), neuromuscular blockers (such as atracurium, cisatracurium, doxacurium, mivacurium, pancuronium, rocuronium, succinylcholine, vecuronium, mivacurium, rapacuronium, rocuronium, succinylcholine, atracurium, cisatracurium, pancuronium, vecuronium, doxacurium, pipecuronium, and/or tubocurarine), nitrates (such as isosorbide dinitrate, isosorbide mononitrate, and/or nitroglycerin), NSAIDs (such as arthrotec, diclofenac, etodolac, indomethacin, ketorolac, sulindac, tolmentin, diflunisal salsalate meloxicam, piroxicam, nabumetone flurbiprofen, ibuprofen, ketoprofen, naproxen, oxaprozin, celecoxib, rofecoxib, and/or valdecoxib), opiates (such as codeine, fentanyl, hydrocodone, hydromorphone, meperidine methadone, morphine, oxycodone, propoxyphene, tramadol, paracetomol, buprenorphine, butorphanol, nalbuphine, pentazocine, nalmefene, naloxone, ziconotide meperidine, and/or morphine), Parkinson's disease treatments (such as amantadine, benztropine, bromocriptine, entacapone, pergolide, pramipexole, ropinirole, selegiline, Sinemet®, tolcapone, and/or trihexyphenidyl), proton pump inhibitors (such as esomeprazole, lansoprazole, omeprazole, pantoprazole, and/or rabeprazole sodium), psoriasis medications (such as acitretin, alefacept, anthralin, calcipotriene, efalizumab, and/or tazarotene), pulmonary medications (such as ipratropium, tiotropium, albuterol, bitolterol, levalbuterol, pirbuterol, metaproterenol, formoterol, salmeterol, Advair®, Symbicort®, beclomethasone, budesonide, flunisolide, fluticasone, Mometasone furoate, triamcinolone, montelukast, zafirlukast, cromolyn sodium, nedocromil, acetylcysteine, and/or aminophylline/theophylline), HMG COA reductase inhibitors (such as atorvastatin, fluvastatin, lovastatin, pravastatin, rosuvastatin, simvastatin, and/or ezetimibe), stimulants (such as atomoxetine, benzphetamine, caffeine, dexmethylphenidate, dextroamphetamine, diethylpropion, methylphenidate, modafinil, pemoline, phendimetrizine, phentermine and sibutramine), tetracycline (such as doxycycline, minocycline, and/or tetracycline), urology medication (such as pentosan, bethanecol, and/or phenazopyridine), vasodilators and vasopressors (such as fenoldopam mesylate, hydralazine, nesiritide, nitroglycerin, dobutamine, dopamine, epinephrine, inaminone, milrinone, nicotine, norepinephrine, phenylephrine, and/or vasopressin).

In embodiments, the treatment method comprises transmucosally administering nalmefene to a subject in need of such treatment. The structure of nalmefene ($C_{21}H_{25}NO_3$, 6-methylene-6-deoxy-N-cyclopropylmethyl-14 hydroxydihydronormorphine) is shown below as Structure (I):

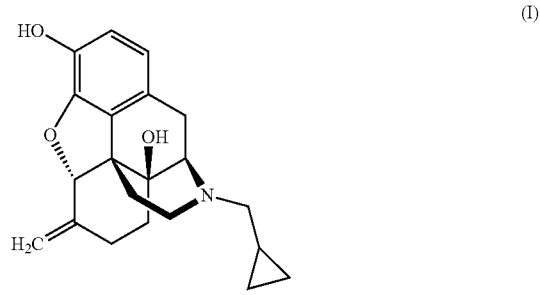

Nalmefene is a mixed µ-opioid receptor (MOR) antagonist and kappa-opioid receptor (KOR) agonist approved for use in the United States as antidote for opioid overdose. Apart from its utility in antagonizing the sedation, respiratory depression, and other actions of opioid agents, nalmefene has also been found useful in treating diverse conditions such as hyperkinesia in children, senile dementia, and sudden infant death syndrome, among others. Oral administration of nalmefene has also been shown to be safe and effective for use in treating alcohol dependence.

Nalmefene can be transmucosally administered to a subject to treat or aid in treatment of opioid overdose, as well as chronic kidney disease-associated pruritus. Transmucosal delivery refers to the delivery of a pharmaceutical agent across a mucous membrane in the oral cavity, pharyngeal cavity, or esophagus. Thus, the pharmaceutical agent is absorbed through the buccal, sublingual, gingival, pharyngeal, and/or esophageal mucosa. In some embodiments, the transmucosal administration of nalmefene is buccally or sublingually delivered. As used herein, "buccal" refers to administration directed towards the cheek, from within the mouth, through the mucosal membranes lining the cheeks (i.e., through the buccal mucosa). The term "sublingual"

refers to administration beneath the tongue, through the mucosal membranes lining the floor of the mouth under the tongue (i.e., through the sublingual mucosa).

In embodiments, the nalmefene can be transmucosally delivered through the use of a delivery device comprising an oral polymer film. The term "film" as used herein refers to a thin, flexible sheet of material and is intended to encompass coated films and film products. Particularly, a delivery device comprising an oral thin film having amorphous or crystalline nalmefene nano- and microparticles disposed on a surface thereof can be prepared. The term "nanoparticles" refers to nalmefene particles that are submicron in size. In some embodiments, the average longest dimension of a suitable nanoparticle is no greater than about 5,000 nanometers, 4,000 nanometers, 3,000 nanometers, 2,000 nanometers, 1,000 nanometers, 500 nanometers, 200 nanometers, 100 nanometers, 75 nanometers, 50 nanometers, 40 nanometers, 25 nanometers, or 20 nanometers. The term "crystalline" refers to a compound with a relatively well-defined crystal structure. The term "amorphous" refers to a compound in a non-crystalline state, without regions of crystallinity.

In some embodiments, the nalmefene nano- and microparticles reside in a discrete domain on the surface of an oral polymer film. In some embodiments, the film can be a single layer film that includes two or more discrete domains, wherein at least one domain includes the nalmefene nano- and microparticles. As used herein the term "domain" refers to a region within a film that includes substantially different physical composition, chemical composition, and/or measurable physical properties (such as dissolution of the nalmefene, mucoadhesion, and/or moisture content) compared to another region of the film.

The pharmaceutical composition may further comprise an anti-crystallization agent, a binding polymer, a pH adjusting or buffering agent, a surfactant, a viscosity-enhancing agent, plasticizer, and a solubilizing solvent. The concentration of the active ingredient can be at least about 10 to about 75% w/w relative to the total weight of the pharmaceutical active composition on a dry basis which is in sharp contrast to current drug concentration in conventional film manufacturing processes. This relates to a drug content of about 1 to 25% w/w on a drug blend basis.

The pharmaceutical composition has a pH in a range of about 4 to about 9, which is dependent on the pharmaceutical active(s) present in the composition. For example, factors affecting pH include pKa, log P, solubility, diffusibility and other attributes of the pharmaceutical active. For example, the pH range of nalmefene may be about 5 to about 8.5. The pH of the pharmaceutical composition can be controlled independently of the pH of the film on which the composition is applied. The pH of the pharmaceutical composition is influenced by the physical properties of the pharmaceutical active in the composition, while the pH of the film is generally a function of comfort and ease of administration for the subject. Thus, the pH of the composition and the pH of the film may be different in some situations or may be the same, depending on the pharmaceutical active in the composition.

In embodiments, the delivery device exhibits a residence time in the mouth of a subject ranging from about 1 minute to about 30 minutes and is substantially mucoadhesive to a mucosal surface when placed sublingually under the tongue or placed buccally at the inner lining of the cheek. In embodiments, the delivery device has a residence time of about 5 minutes to about 15 minutes. For example, the delivery device may have a residence time of about 5 minutes, 6 minutes, 7 minutes, 8 minutes, 9 minutes, 10 minutes, 11 minutes, 12 minutes, 13 minutes, 14 minutes, or 15 minutes.

The anti-crystallization agent may comprise various sugar alcohols and di-alcohols, including, for example one or more of sorbitol, mannitol, xylitol, isomalt, and the like. The anti-crystallization agent may be present in the composition in an amount that is about 1% to 25% w/w of the active ingredient. For example, the anti-crystallization agent may be present in the composition in an amount that is about 5%, 10%, 15%, 20%, or 25% w/w of the active ingredient. For example, if the weight of the active ingredient is 20 mg and the amount of anti-crystallization agent being used is 10 wt % of the active ingredient, the weight of the anti-crystallization agent in the composition would be 2 mg. The anti-crystallization agent may include a combination of one or more sugar alcohols, for example, a combination of sorbitol and mannitol. When sorbitol and mannitol are used collectively as the anti-crystallization agent, the amount of each may vary. For example, the ratio of the amount of sorbitol to mannitol may vary from 1-20:1 (sorbitol:mannitol). Thus, the ratio of sorbitol to mannitol may be 1:1, 5:1, 10:1, 15:1, and/or 20:1 or any ratio within the range of 1-20:1.

The pH adjusting or buffering agent may comprise a component selected from the group consisting of phosphate buffers, acetate buffers, citrate buffers, arginine buffers, TRIS buffers, histidine buffers, ammonium glycyrrhizinate, and mixtures thereof. For example, the buffering agent may comprise monobasic sodium phosphate (MBSP), dibasic sodium phosphate (DBSP), ammonium glycyrrhizinate NF, and mixtures thereof. The buffering agent may include a combination of one or more components, for example, a combination of DBSP and ammonium glycyrrhizinate NF. The amount of each may vary. For example, the ratio of the amount of DBSP to ammonium glycyrrhizinate NF may vary from 1-20:1 (DBSP: ammonium glycyrrhizinate NF). Thus, the ratio of DBSP to ammonium glycyrrhizinate NF may be 1:1, 5:1, 10:1, 15:1, and/or 20:1 or any ratio within the range of 1-20:1.

The pharmaceutical composition further comprises one or more solubilizing solvent or drug solubilizers. The term "drug solubilizer" or "solubilizing solvent" as used herein refers to an agent that forms a solubilized phase of a pharmaceutical active. Suitable drug solubilizers can include (but are not limited to) solvents, oils, surfactants, or phospholipids. In some embodiments, the solubilizing solvent can be present in an amount of about 0.001-5 wt. % of the total weight of the pharmaceutical composition (e.g., 0.001, 0.1, 0.5, 1, 1.5, 2, 2.5, 3, 3.5, 4, 4.5, or 5 wt. %). Exemplary solubilizing solvents may include, without limitation, National Formulary grade ethanol (ethanol NF), United States Pharmacopeia grade propylene glycol (propylene glycol USP), glycerol USP, purified water USP, isopropyl alcohol and combinations thereof. The solubilizing solvent may include a combination of one or more components, for example, a combination of ethanol NF and water USP or a combination of ethanol NF, water USP, and propylene glycol USP. The amount of each may vary. For example, the ratio of the amount of ethanol NF to water USP may vary from 1-90:1 (ethanol NF:water USP). Thus, the ratio of ethanol NF to water USP may be 3:1, 5:1, 10:1, 15:1, and/or 20:1 or any ratio within the range of 1-90:1.

Surfactants can serve multiple roles in pharmaceutical compositions. For example, they can modulate solubility and bioavailability of APIs; increase the stability of active ingredients in the dosage forms; help active ingredients maintain preferred polymorphic forms; maintain the pH and/or osmolality of liquid formulations; act as antioxidants, emulsifying agents, aerosol propellants, tablet binders, and disintegrants; prevent aggregation or dissociation; and modulate immunogenic responses of active ingredients. Non-ionic surfactants, such as ethers of fatty alcohols are commonly used in pharmaceuticals.

Figure 6:
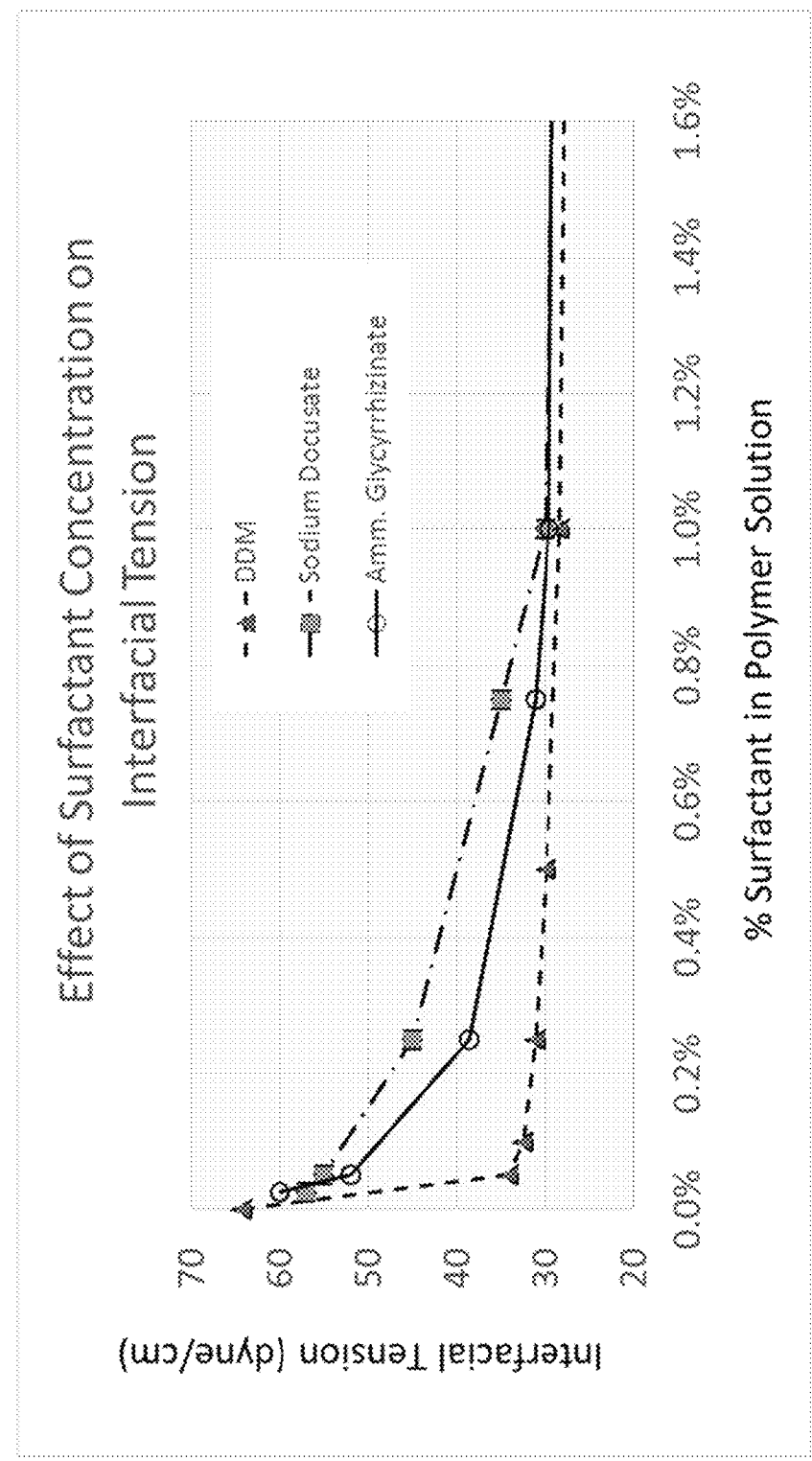
FIG. 6 is a line chart plotting interfacial tension in dyne/cm for three exemplary surfactants at different concentrations.

In the manufacturing method, the surfactant reduces the surface tension or interfacial tension of the composition allowing maximization of the surface area on the surface of the film when a dropwise deposition method is used for manufacturing, and the viscosity enhancing agent prevents the deposited droplet from flowing uncontrollably. In an embodiment, the composition has a surface or interfacial tension of about 20 dyne/cm to about 45 dynes/cm and a viscosity of about 50 cP to about 5000 cP. For example, the viscosity may range from about 50 cP to about 500 cP or from about 100 cP to about 400 cP. In another embodiment, the composition may be deposited as a droplet in a shallow well in the polymer film. Embodiments wherein the composition is deposited in a well can allow greater variation in composition viscosity and surface tension. For example, the surface or interfacial tension may be from 20 dynes/cm to lower than 45 dynes/cm, and the viscosity can be less than about 50 cP to 400 cP. The use of surfactant enables better process control of the droplet dimensions controlled by the interfacial properties of the pharmaceutical composition as long as the surfactant concentration is greater than the critical micelle concentration above which the interfacial tension remains constant as shown in FIG. 6.

As described herein, the surfactant serves as a wettability enhancing agent. It reduces the interfacial tension of the composition from its original non-surfactant state. Exemplary surfactants may include sodium lauryl sulfate, phospholipids, bile salts, ammonium glycyrrhizinate, alkyl maltosides, copovidone, chitobiose, chitosan, Brij(@), Tween® and their analogues. Additionally, exemplary surfactants may include n-dodecyl b-D maltoside, ammonium glycyrrhizinate NF, sodium docusate USP, β-dodecyl maltoside (an alkyl polyglycoside), sucrose-6-monolaurin (a saccharide fatty acid ester), polysorbate (ethoxylated sorbitan-oleic acid ester), 1-monolaurin (a monoacylglycerol), and α-tocopheryl polyethylene glycol succinate, and benzalkonium chloride. Additional examples may include anionic surfactants, such as: (a) carboxylates: alkyl carboxylates-fatty acid salts; carboxylate fluoro surfactants, (b) sulfates: alkyl sulfates (e.g., sodium lauryl sulfate); alkyl ether sulfates (e.g., sodium laureth sulfate), (c) sulfonates: docusates (e.g., dioctyl sodium sulfosuccinate); alkyl benzene sulfonates, and (d) phosphate esters: alkyl aryl ether phosphates; alkyl ether phosphates. The solvent may include a combination of one or more components. The solvent may be present in an amount of 0.001-5 wt. % of the total weight of the pharmaceutical composition.

Viscosity-enhancing agents or viscosity modifiers can change the thickness or texture of pharmaceutical ingredients. Viscosity modifiers can include such products as thickeners, texturizers, gelation agents and stiffening agents. Many viscosity modifiers can be used to convert liquids to gels, pastes or powders to aid formulators in creating the ideal product for end users. A viscosity modifier can also decrease the thickness of a liquid to improve pour ability and ultimately make it more palatable.

Typically polymers are used as viscosifying agents. In embodiments of the composition, aqueous or organic polar solvents are used. Thus, a variety of polymers can be used as viscosity-enhancing agents. The polymers may be water-soluble, water-swellable, water-insoluble fillers, or a combination thereof. Exemplary viscosity-enhancing agents may also include commonly used viscosity modifiers such as gums, e.g., xanthan gum, tragancanth gum, guar gum, acacia gum, arabic gum, hydrophilic and hydrohyphobic starches, pregelatinized starches, celluloses such as hydroxyethylcellulose, hydroxypropylmethylcellulose, methylcellulose, hydroxy ethyl cellulose, hydroxy propyl cellulose, polyvinyl pyrrolidone, polyvinyl alcohol, polyvinylpyrrolidone, carboxymethyl cellulose, polysaccharides, polyethylene oxide, pullulan, sodium alginate, polyethylene glycol, polyacrylic acid, methyl methacrylate copolymer, carboxyvinyl copolymers, starch, gelatin, and combinations thereof. For high viscosities, it may be desirable to incorporate a greater polymer content that provides a high level of viscosity as compared to lower dosages.

The pharmaceutical composition may further comprise one or more components selected from the group consisting of a fast dissolving polymer, a hydrogel polymer, a self-assembling or self-aggregating moiety, a dispersing agent, an oxygen scavenger, a bioenhancer, a flavoring agent, a colorant, and a taste masking agent. The fast dissolving polymer may include a polymer that will dissolve in about 1 minute to about 3 minutes when placed in the mouth of a subject. The self-assembling or self-aggregating moiety may include one or more of phospholipids, bile acids, bile salts, nano-platelet structures, and edible clays. Moreover, divalent salts such as calcium, magnesium and zinc salts, in combination with hydrogels such sodium alginate and kappa carrageenan may be used to form a self-assembling barrier layer. It will be appreciated that the divalent salt may be present in the pharmaceutical active composition or it may be present in the polymer film. Correspondingly, the hydrogel may be present in the pharmaceutical active composition or it may be present in the polymer film. In embodiments, one of the hydrogel and the divalent salt is in the pharmaceutical active composition and the other of the hydrogel and the divalent salt is in the polymer film, such that when the divalent salt and the hydrogel come into contact with one another, they form a barrier layer. The self-assembling or self-aggregating moiety may also include hydrophobic self-assembling moieties.

The term "bioenhancer" refers to a substance that increases the bioactivity, bioavailability, and/or efficacy of nalmefene. Suitable bioenhancers can include (but are not limited to) one or more fatty acids, alkaloids, Piperidine, allicin, curcumin, quercetin, and the like. In some embodiments, the bioenhancer can be present in an amount of about 0-5 weight percent of the total weight of the first domain (e.g., 0, 0.5, 1, 1.5, 2, 2.5, 3, 3.5, 4, 4.5, or 5 weight percent).

The term "flavoring agent" refers to any additive that gives the pharmaceutical composition a desired taste or smell. Suitable taste masking agents can include (but are not limited to) cellulose acetate, cellulose acetate butyrate, ethylcellulose, methylcellulose, and combinations thereof. Potential surfactants can also be used in combination above their critical micelle concentration to provide taste masking. Suitable flavoring agents can include (but are not limited to) natural and artificial flavors such as oil of peppermint, menthol, oil of spearmint, vanilla, oil of cinnamon, oil of wintergreen, lemon oil, orange oil, grape oil, lime oil, grapefruit oil, apple flavor oil, raspberry oil, strawberry oil, pear oil, blueberry oil, blackberry oil, watermelon flavor, cherry oil, licorice oil, apricot essence, clove oil, anise oil, cardamom oil, coriander oil, *eucalyptus* oil, fennel oil, lemongrass oil, nutmeg oil, and combinations thereof.

Colorants are primarily used to impart appearance to a pharmaceutical dosage form. The purpose of coloring varies with different formulations. Colorings may be used to increase aesthetic appearance, to prolong stability, to produce standard preparations, and/or for identification of a particular formulation. Suitable colorants for the composition described herein can include FD&C colorants, D&C pigments and Lake dyes.

In the delivery device, the pharmaceutical composition is disposed directly on the surface of a relatively thin polymer film at concentrations of 1-50% weight active ingredient/weight active composition or higher. The delivery device can provide high active bioavailability and fast-onset-of-action while avoiding first pass metabolism.

In a dispersed state, the average diameters of the active particles can range from 50 nanometers up to 5 micrometers in size before and after drying. While drying can be conducted by convective drying methods that are conventionally used in oven drying processes, the faster the rate of drying, the smaller the size dimension of the active ingredient in the film device. In a preferred embodiment, the drying time is less than about 5 minutes, and flash drying within less than about 1 minute offers the most suitable morphologies.

In embodiments, liquid droplet particles may be dispersed at a controlled continuous flow rate and evenly sprayed on the surface of the film. These liquid droplets may be deposited in a dry, semi-dry or wet film state.

The polymer film comprises a drug-free, dissolution rate-controlling, mucoadhesive polymer that offers residence time control from about 1 minute to about 30 minutes. The film may provide effective taste masking of the pharmaceutical active ingredient and adequate mucoadhesion when applied under the tongue (sublingual) or on to the inner lining of the cheek (buccal) inside a subject's mouth.

Advantageously, the active agent resides on the surface of the film of the delivery device at relatively high concentrations (i.e., an enriched drug domain), and in some embodiments, very high concentrations. Conventional film design and manufacturing processes are not able to prepare a film having the high active agent concentrations at the surface that are available in the described pharmaceutical active-containing delivery device. Moreover, the delivery device described herein can provide enhanced permeation, rapid on-set of action, high active absorption, and reduced metabolites when applied under the tongue (sublingually) or on the inner lining of the check (buccally) in a subject's mouth. Additionally, the polymers of the film can be selected to provide a suitable mucoadhesion with buccal mucosa. Polymer molecular weights can be adjusted to control residence time in the mouth (i.e., time to complete film dissolution). Polymer ratios can also be adjusted to control residence time and mucoadhesive attributes. Dissolution time can be balanced between a time that is too quick and a time that is too long. For example, if the polymer dissolves too quickly, the active ingredient can be swallowed, thereby resulting in delayed and oral drug delivery. If the polymer dissolves too slowly, transmucosal delivery of the active ingredient may be slow and delayed. In emergency medical scenarios, such as an opioid overdose, delay in delivery of active ingredient can be particularly problematic. In embodiments, a target residence time is between about 5 minutes and about 15 minutes, and preferably between about 5 minutes and about 10 minutes.

In an embodiment, exemplary polymers include sodium carboxymethylcellulose (NaCMC 7L2P) and different molecular weights of hydroxypropyl methylcellulose (HPMC). These polymers can provide a balance between mucoadhesive attributes of the film (i.e., sticking to the buccal mucosa), film-forming characteristics for blend processing, and residence time in the mouth.

In an exemplary embodiment, the product is a single layer delivery device comprising a polymer film and an enriched drug domain of pharmaceutical active composition comprising nalmefene or salt thereof. The pharmaceutical composition is not self-supporting and cannot be physically separated from the polymer film. The pharmaceutical composition in the enriched drug domain can be substantially thinner compared to the polymer film, such as at least an order of magnitude thinner than the overall thickness of the film. For example, the thickness of the polymer film can be about 200%, 500%, 750%, 1000%, 2000%, 3000%, 4000%, 5000%, 7500% or 10000% of the thickness of pharmaceutical composition. In some embodiments, the pharmaceutical composition in the enriched drug domain of the delivery device can be physically inseparable from the polymer film but remain circumscribed by the film composition in the film layer. For example, the enriched drug domain surface area can be about 5, 10, 15, 20, 25, 30, 35, 40, 45, 50, 55, 60, 65, 70, 75, 80, 85, 90, 95, or 100% of the polymer film.

The pharmaceutical active composition can comprise a fast dissolving polymer binding the composition to the surface of the polymer film.

In embodiments, the delivery device is a single layer. The term "single layer" refers to a structure that does not include multiple layers that can separated from each other, such as by peeling apart, wedging the regions away from each other, or have structural integrity. Thus, the disclosed delivery device includes a single layer with a polymer film having a pharmaceutical active composition disposed thereon, but is not a multi-layered, laminated structure. It should be appreciated that the polymer film and the pharmaceutical active composition can be discrete or contiguous in structure, unlike a layer that must be contiguous. In some embodiments, the delivery device comprises at least one component (i.e., polymer film or pharmaceutical active composition) with a thickness of no more than 500 μm in an unhydrated state. In some embodiments, each component in the delivery device has a thickness of 500 μm or less.

The polymer film comprises one or more polymer matrices and optionally one or more permeation enhancers, pH adjusting buffers or agents, taste masking agents, and/or flavors. Any desired polymer matrix can be used, including (but not limited to) water soluble, water swellable, and/or water erodible polymers. For example, in some embodiments, the polymer matrix can be selected from hydroxy propyl methyl cellulose (HPMC), methyl cellulose, hydroxyethyl cellulose (HPC), hydroxypropyl cellulose, polyvinyl pyrrolidone, sodium carboxymethyl cellulose, polyethylene oxide (PEO), pullulan, alginic acid, sodium alginate, polyethylene glycol, pectins, xanthan gum, tragancanth gum, guar gum, acacia gum, arabic gum, locust bean gum, gellan gum and combinations thereof, polyacrylic acid, Polycarbophil®, methyl methacrylate copolymer, carboxy vinyl copolymers, natural and hydrolyzed starch, gelatin type A and B, carrageenan, and combinations thereof.

As used herein the phrase "water soluble polymer" and variants thereof refer to a polymer that is at least partially soluble in water, fully or predominantly soluble in water, or absorbs water. Polymers that absorb water are often referred to as being water swellable polymers. In some embodiments, materials used in the polymer matrix of polymer film can be water soluble or water swellable at room temperature and/or other temperatures, such as temperatures exceeding room temperature.

In some embodiments, the polymer matrix can be present in an amount of about 5-100 weight percent of the total weight of the polymer film (e.g., about 5, 10, 15, 20, 25, 30, 35, 40, 45, 50, 55, 60, 65, 70, 75, 80, 85, 90, 95, or 100 weight percent, based on the total weight of the domain). The polymer matrix provides a self-supporting structure and desired residence time for improved bioavailability.

The polymer film can optionally include any permeation enhancer known or used in the pharmaceutical arts. The term "permeation enhancer" refers to a component used to enhance the penetration rate of a pharmaceutical active through the skin. Suitable permeation enhancers can include (but are not limited to) lipophilic solvents, surfactants, menthol, fatty acid esters and derivatives, polyhydric alcohols, bile salts, chelators, cyclodextrins and chitosan and combinations thereof. For example, suitable permeation enhancers can include (but are not limited to) chitobiose, chitosan, methyl sulfoxide (DMSO), linoleic acid (LA), isopropyl myristate (IPM), sodium glycodeoxycholate (GDC), beta-cyclodextrin, oleic acid (OA), and combinations thereof. In some embodiments, the permeation enhancer can be present in an amount of about 0 to about 5 weight percent of the total weight of the polymer film (e.g., 0, 0.5, 1, 1.5, 2, 2.5, 3, 3.5, 4, 4.5, or 5 weight percent).

The polymer film can further include one or more pH-adjusting buffers or agents. Any buffer that can resist a change in pH can be used. For example, in some embodiments, the buffer can be selected from phosphate, acetate, citrate, arginine, TRIS, and histidine buffers. For example, in some embodiments, a citric acid buffer can be used. In some embodiments, the buffer can be present in an amount of about 0 to about 5 weight percent of the total weight of the polymer film (e.g., 0, 0.5, 1, 1.5, 2, 2.5, 3, 3.5, 4, 4.5, or 5 weight percent).

The polymer film can optionally include taste masking agents and/or flavoring agents to improve the flavor of the film. The term "taste masking agent" refers to an agent that is added to a composition to mask the taste of one or more unpleasant tasting components. The term "flavoring agent" refers to any additive that gives the disclosed film a desired taste or smell. Suitable taste masking agents can include (but are not limited to) cellulose acetate, cellulose acetate butyrate, ethylcellulose, methylcellulose, and combinations thereof. Suitable flavoring agents can include (but are not limited to) natural and artificial flavors such as oil of peppermint, menthol, oil of spearmint, vanilla, oil of cinnamon, oil of wintergreen, lemon oil, orange oil, grape oil, lime oil, grapefruit oil, apple flavor oil, raspberry oil, strawberry oil, pear oil, blueberry oil, blackberry oil, watermelon flavor, cherry oil, licorice oil, apricot essence, clove oil, anise oil, cardamom oil, coriander oil, *eucalyptus* oil, fennel oil, lemongrass oil, nutmeg oil, and combinations thereof. In some embodiments, the taste masking agents and/or flavoring agents can be present in an amount of about 0-5 weight percent of the total weight of the polymer film (e.g., 0, 0.5, 1, 1.5, 2, 2.5, 3, 3.5, 4, 4.5, or 5 weight percent).

In some embodiments, the local pH of the polymer film is about 3.5 to about 8.5, such as about 3.5, 4, 4.5, 5, 5.5, 6, 6.5, 7, 7.5, 8, or 8.5. In some embodiments, the local pH of the pharmaceutical active composition is between 4 and 9, such as between 5 and 8, or between 6 and 7.5. In some embodiments, the pH of the delivery device is between 3 and 9, such as between 4.5 and 8 or between 5.5 and 7.5.

In embodiments of the device, the pH of the film and the composition can be tuned to provide a target solubility and permeability of the active ingredient. For embodiments wherein the active ingredient is nalmefene, the film pH can range from 5.5 to 8.0 and can be controlled using phosphate buffer salts. Based on the solubility of nalmefene, a target pH between 6.5 to 7.5 can be used to be close to the two-phase boundary thus allowing relatively instantaneous phase separation. Glycerin USP can be used as a plasticizer to reduce brittleness and maintain the self-supporting integrity of the film.

In embodiments, the pharmaceutical active composition comprises nalmefene or a salt thereof, which is present in a therapeutically effective amount. The term "therapeutically effective amount" refers to the amount of pharmaceutical active that is effective at treating or aiding in treating opioid overdose and/or reducing, eliminating, treating, and/or controlling the symptoms of chronic kidney disease-associated pruritus, cholestatic pruritus, and/or prurigo nodularis. The active composition can comprise about 1 to about 32 mg of nalmefene. Thus, the delivery device can comprise at least about (or no more than about) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 mg nalmefene.

In some embodiments, the alternative or additional pharmaceutical active can be a food or nutraceutical bioactive agent selected from one or more constituents in foods and/or dietary supplements that are responsible for changes in health status. For example, the additional pharmaceutical active can include (but is not limited to) components of plants, such as fruits and vegetables, e.g., isoflavones and phytoestrogens found in soy, lycopene found in tomatoes, flavonoids such as anthocyanins found in berries, epigallocatechin gallate (EGCG) found in green tea, resveratrol found in red grape products, soluble dietary fiber products such as *psyllium* seed husk, sulforaphane from broccoli, isoflavanoids from soy or clover, flavonoids, antioxidants, alpha-linolenic acid from flax seeds, extracts such as *ginseng*, garlic oil, etc.

In some embodiments, the alternative or additional pharmaceutical active can be a biological active (e.g., a biologically active substance in plants that has proven beneficial effects on health (such as the cholesterol-lowering effects of phytosterols) and/or potential beneficial effects on health (such as phytochemicals and/or phytonutrients)). For example, suitable biological actives can include (but are not limited to) phytochemicals in leaves, stems, roots, tubers, buds, fruits, seeds and flowers, and plant-derived foods and drinks (such as tea, coffee, alcoholic beverages). Suitable biological actives can further include flavonoids found in a range of plant-derived foods, including tea, wine, onions, apples and berries; phenolic acids found in tea and coffee; and/or carotenoids (some of which are precursors of vitamin A) prevalent in red, green, and orange fruits and vegetables.

The alternative or additional pharmaceutical active can further include one or more cosmetic agents, veterinary medicine agents, functional ingredients, and the like. Examples include alpha linoleic acid (ALA), cannabidiols (CBD), coenzyme Q10, curcumin, chondroitin, glucosamine, glutamine, hemp oils, lutein, L-Carnitine, melatonin, methionine, neem, omega-3 and -6 fish oil, St. John's Wort, saw palmetto, ubiquinone, vitamins, xylitol, or zeazanthin.

The pharmaceutical active can be a solid solution, amorphous, microencapsulated and/or in a monomorphic crystalline microparticle state. For example, the pharmaceutical active can be present as solid solution or a substantially-uniform, dispersed, amorphous microparticle in the pharmaceutical composition. The term "solid solution" as used herein refers to a solid that is molecularly dispersed in a domain to form a glassy state. The term "amorphous" as used herein refers to a solid material with molecular structures that do not have a definite geometric shape or a lattice pattern as assessed by XRD diffraction. Amorphous particles can have a glass point, a gel point, and can lack a crystalline lattice structure. In embodiments, amorphous particles are preferred for increasing bioavailability of the pharmaceutical active ingredient. A "microencapsulated" particle refers to a particle wherein the pharmaceutical active is contained within a thin polymeric coating, forming small particles called microcapsules. The polymer acts as a protective film, isolating the pharmaceutical active. The polymer film dissolves through a specific stimulus, releasing the active in the intended place or at the intended time. "Monomorphic crystalline state" refers to a crystal state of one lattice configuration. In embodiments, the term "microparticle" as used herein refers to a particle with a diameter of about 0.001-100 μm. In some embodiments, suitable amorphous microparticles have a diameter of less than about 25 μm, 10 μm, 5 μm, 1 μm, 0.5 μm or 0.1 μm.

In some embodiments, the pharmaceutical active composition can comprise one or more self-aggregating and/or self-assembling moieties that provide permeation enhancement characteristics. The term "self-assembling" as used herein refers to molecular structures that arrange themselves upon induced physical change and/or triggered phase transition to minimize the overall free energy of the system, resulting in a thermodynamically stable system. The term "self-aggregating" refers to a structure resulting from the ability of a molecule to aggregate into high concentration domains or "rich domains." In some embodiments, the self-aggregating and/or self-assembling moieties can be present in an amount of about 0-5 weight percent of the total weight of the pharmaceutical active composition (e.g., 0, 0.5, 1, 1.5, 2, 2.5, 3, 3.5, 4, 4.5, or 5 weight percent). The self-aggregating and/or self-assembling moieties provide directional permeation.

In some embodiments, suitable self-aggregating and/or self-assembling moieties can include (but are not limited to) phospholipids, bile salts, nanoplatelets, clays, polar lipids, or combinations thereof. For example, calcium chloride can be used in combination with sodium alginate to create a self-assembling barrier gel. It will be appreciated that calcium chloride may be present in the pharmaceutical active composition or it may be present in the polymer film. Correspondingly, the sodium alginate may be present in the pharmaceutical active composition or it may be present in the polymer film. In embodiments, one of the sodium alginate and the calcium chloride is in the pharmaceutical active composition and the other of the sodium alginate and the calcium chloride is in the polymer film, such that when they come into contact with one another, they form a barrier layer. Additionally, suitable examples of the self-aggregating and/or self-assembling moieties can include phosphatidylcholine, phosphatidic acid, phosphatidylcholine, phosphatidylethanolamine, phosphatidylglycerol, phosphatidylcholine, phosphatidylserine, phosphatidylinositol, phosphatidylinositol phosphate, phosphatidylinositol bisphosphate, phosphatidylinositol triphosphate, and/or sphingomyelin. More specifically, the self-aggregating and/or self-assembling moieties can comprise 1,2-didecanoyl-sn-glycero-3-phosphocholine, 1,2-dierucoyl-sn-glycero-3-phosphate (sodium salt), 1,2-dierucoyl-sn-glycero-3-phosphocholine, 1,2-dierucoyl-sn-glycero-3-phosphoethanolamine, 1,2-dierucoyl-sn-glycero-3-phospho-rac-(1-glycerol . . . ) (sodium salt), 1,2-dilinoleoyl-sn-glycero-3-phosphocholine, 1,2-dilauroyl-sn-glycero-3-phosphate (sodium salt), 1,2-dilauroyl-sn-glycero-3-phosphocholine, 1,2-dilauroyl-sn-glycero-3-phosphoethanolamine, 1,2-dilauroyl-sn-glycero-3-phospho-rac-(1-glycerol) (sodium salt), 1,2-dilauroyl-sn-glycero-3-phospho-rac-(1-glycerol) (ammonium salt), 1,2-dilauroyl-sn-glycero-3-phosphoserine (sodium salt), 1,2-dimyristoyl-sn-glycero-3-phosphate (sodium salt), 1,2-dimyristoyl-sn-glycero-3-phosphocholine, 1,2-dimyristoyl-sn-glycero-3-phosphoethanolamine, 1,2-dimyristoyl-sn-glycero-3-phospho-rac-(1 glycerol) (sodium salt), 1,2-dimyristoyl-sn-glycero-3-phospho-rac-(1-glycerol) (ammonium salt), 1,2-dimyristoyl-sn-glycero-3-phospho-rac-(1-glycerol) (sodium/ammonium salt), 1,2-dimyristoyl-sn-glycero-3-phosphoserine (sodium salt), 1,2-dioleoyl-sn-glycero-3-phosphate (sodium salt), 1,2-dioleoyl-sn-glycero-3-phosphocholine, 1,2-dioleoyl-sn-glycero-3-phosphoethanolamine, 1,2-dioleoyl-sn-glycero-3-phospho-rac-(1-glycerol) (sodium salt), 1,2-dioleoyl-sn-glycero-3-phosphoserine (sodium salt), 1,2-dipalmitoyl-sn-glycero-3-phosphate (sodium salt), 1,2-dipalmitoyl-sn-glycero-3-phosphocholine, 1,2-dipalmitoyl-sn-glycero-3-phosphoethanolamine, 1,2-dipalmitoyl-sn-glycero-3-phospho-rac-(1-glycerol) (sodium salt), 1,2-dipalmitoyl-sn-glycero-3-phospho-rac-(1-glycerol) (ammonium salt), 1,2-dipalmitoyl-sn-glycero-3-phosphoserine (sodium salt), 1,2-distearoyl-sn-glycero-3-phosphate (sodium salt), 1,2-distearoyl-sn-glycero-3-phosphocholine, 1,2-distearoyl-sn-glycero-3-phosphoethanolamine, 1,2-distearoyl-sn-glycero-3-phospho-rac-(1-glycerol) (sodium salt), 1,2-distearoyl-sn-glycero-3-phospho-rac-(1-glycerol) (ammonium salt), 1,2-distearoyl-sn-glycero-3-phosphoserine (sodium salt), hydrogenated egg PC hydrogenated soy PC, 1-myristoyl-sn-glycero-3-phosphocholine, 1-palmitoyl-sn-glycero-3-phosphocholine, 1-stearoyl-sn-glycero-3-phosphocholine, 1-myristoyl-2-palmitoyl-sn-glycero 3-phosphocholine, 1-myristoyl-2-stearoyl-sn-glycero-3-phosphocholine, 1-palmitoyl-2-myristoyl-sn-glycero-3-phosphocholine, 1-palmitoyl-2-oleoyl-sn-glycero-3-phosphocholine, 1-palmitoyl-2-oleoyl-sn-glycero-3-phosphoethanolamine, 1-palmitoyl-2-oleoyl-sn-glycero-3-phospho-rac-(1-glycerol) (sodium salt), 1-palmitoyl-2-stearoyl-sn-glycero-3-phosphocholine, 1-stearoyl-2-myristoyl-sn-glycero-3-phosphocholine, 1-stearoyl-2-oleoyl-sn-glycero-3-phosphocholine, 1-stearoyl-2-palmitoyl-sn-glycero-3-phosphocholine, 1-stearoyl-2-palmitoyl-sn-glycero-3-phosphocholine; edible clay components such as sodium bentonite, polyphosphate, montmorillonite, kaolin, cloisite; bile acids and salts that include cholic acid, sodium and calcium cholates salts, chenodeoxycholic acid, sodium and calcium chenodeoxycholates salts, chenodeoxycholic acid, sodium and calcium chenodeoxycholates salts, glycocholic acid, sodium and calcium glycocholates salts, glycyrrhetinic acid, glycyrrhentinate sodium, taurocholic acid, sodium and calcium taurocholates salts, lithocholic acid, sodium and calcium lithocholates salts; nanoplatelets, bentonite, cloisite, and/or combinations thereof.

In some embodiments, the pharmaceutical active composition can optionally comprise one or more oxygen scavengers. The term "oxygen scavenger" as used herein refers to a composition that reduces or eliminates the generation of unwanted oxidation products. In some embodiments, the oxygen scavenger is effective to absorb oxygen. Suitable oxygen scavengers that can be incorporated into pharmaceutical active composition can include (but are not limited to) ascorbates, isoascorbates, tannins, sulfites, oxidizable polymers, polyacids, polynucleic acids, proteins, polysaccharides, polypeptides, ethylenediamine tetraacetic acid (EDTA) and salts thereof, organic glutamic acid and salts thereof, citric acid and salts thereof, phosphonates, histidine, phytochelatin, hemoglobin, chlorophyll, humic acid, transferrin, desferrioxamine, vitamin E acetate, tocopherol, and combinations thereof. In some embodiments, the oxygen scavenger can be present in an amount of about 0-5 weight percent of the total weight of the pharmaceutical active composition (e.g., 0, 0.5, 1, 1.5, 2, 2.5, 3, 3.5, 4, 4.5, or 5 weight percent).

In some embodiments, the ratio of pharmaceutical active to oxygen scavenger is about 100:1 to about 1:10, such as about 100:1, 90:1, 80:1, 70:1, 60:1, 50:1, 40:1, 30:1, 20:1, 10:1, 1:1, 1:2, 1:3, 1:4, 1:5, 1:6, 1:7, 1:8, 1:9, or 1:10. It should be appreciated that the oxygen scavenger can improve the oxidative stability of the pharmaceutical active or a pharmaceutically acceptable salt thereof. The oxygen scavenger can further improve the oxidative stability of one or more self-aggregating and/or self-assembling moieties when present in the disclosed film or layer.

In some embodiments, the delivery device may comprise more than a polymer film and a pharmaceutical active composition. For example, the device can include a second polymer film comprising a self-assembling phospholipid and/or bile salts to provide permeation enhancement.

There is currently no commercially available single-layer delivery device that comprises a polymer film and a pharmaceutical active composition comprising nalmefene disposed thereon, wherein at least one of the pharmaceutical active composition or the polymer film provides effective taste masking and enhanced transmucosal absorption when the pharmaceutical active composition is placed in contact with the oral mucosa. In some embodiments, at least one of the pharmaceutical active composition or the polymer film provides enhanced transmucosal absorption. In some embodiments, the mucoadhesive polymer provides enhanced absorption when the polymer film is placed in contact with the mucosal tissue of a subject.

In embodiments, a method of manufacturing the pharmaceutical active-containing transmucosal delivery device comprises blending a polymer matrix and a pH adjusting agent; solubilizing the blend; casting the blend into a wet polymer film; drying the polymer film; applying a pharmaceutical active composition onto a surface of the polymer film, wherein a viscosity of the composition is from about 1 cP to about 400 cP; and heating the polymer film with the pharmaceutical active composition applied thereto in order to form the pharmaceutical active-containing transmucosal delivery device. The manufacturing process includes two significant steps—casting the polymer film and depositing the active ingredient(s). The two steps can be subdivided into multiple unit operations. A schematic flow diagram is provided in FIG. 1.

In an exemplary embodiment, the manufacturing procedure may proceed as follows. Prepare a bubble-free film blend. Subsequently, cast the film. The blend can be coated on top of a non-siliconized side of a release liner using a knife-blade coater. Films with a thickness value ranging from about 100 micrometers to 140 micrometers can be prepared. The coated polymer can be dried overnight with a minimum drying time of about 12 hours. The water in the film can be captured by measuring the drying loss in the weight of the film. The dried films can be stored for later use.

Figure 2:
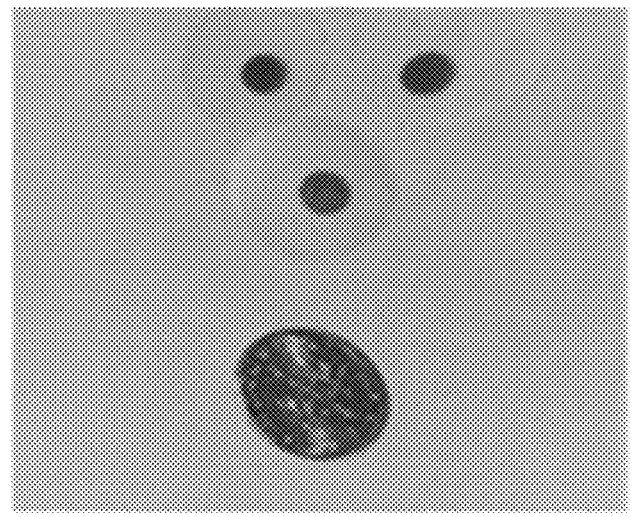
FIG. 2 is a photograph showing an exemplary delivery device.
Figure 3A:
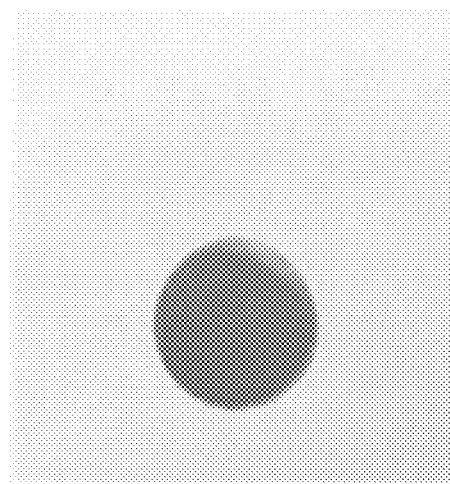
FIGS. 3A and 3B are photographs showing exemplary delivery devices.
Figure 3B:
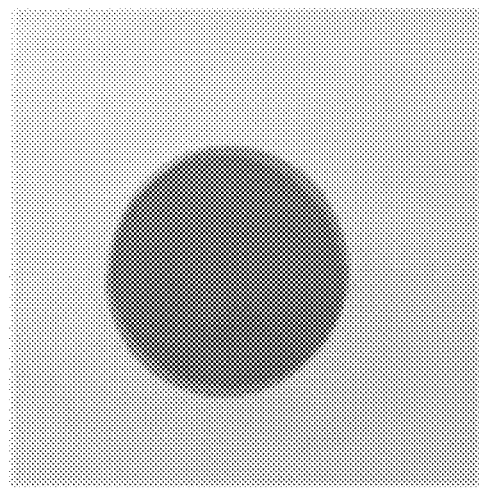

Pharmaceutical active composition can be deposited on the laminate film. In exemplary embodiments, the pharmaceutical active composition can be deposited in different ways. For example, the active can be deposited using drop-wise deposition or a spray-type deposition. For the drop-wise deposition, different nozzle configurations can be used. For example an 8G to 24G needle assembly can be used. For drop-wise deposition, the number of discrete drops placed on the film determines the dose strength of the pharmaceutical active. In embodiments, the viscosity of the pharmaceutical active composition used with a drop-wise deposition method is about 100 cP to about 400 cP. The viscosity and surface tension of the pharmaceutical active composition affect the size of the droplets, and thus, the dosage amount of the pharmaceutical active. For spray deposition, different spray devices may be used. For example, a 130-kHz ultrasonic spray nozzle can be used. For spray deposition, the dispensed pharmaceutical active is uniformly coated on the film. Thus, the dose depends on the surface area of the film coated with the active and the rate at which the active is dispensed. In embodiments, the viscosity of the pharmaceutical active composition used with a spray deposition method is about 1 cP to about 100 cP. The viscosity and surface tension of the pharmaceutical active composition also affect the dosage amount of the pharmaceutical active when a spray deposition method is used. FIGS. 2, 3A and 3B are photographs showing exemplary delivery devices prepared using different deposition methods. The embodiments shown in FIG. 2 were prepared using a drop-wise method. For these embodiments, the dose strength depends on the number of drops. The embodiments shown in FIGS. 3A (2 mg) and 3B (4 mg) were prepared using atomized spray on a film. For these embodiments, the dose depends on the surface area of the film.

Figure 4:
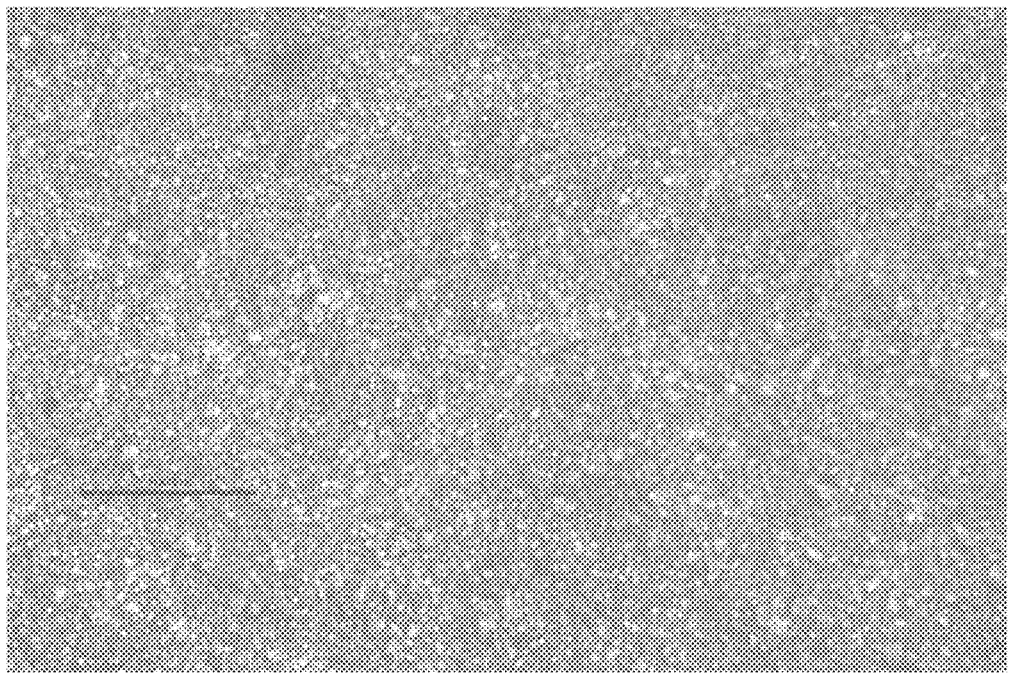
FIG. 4 is a micrograph of an exemplary embodiment of the delivery device using ultrasonic spray to deposit nalmefene on a film.
Figure 5:
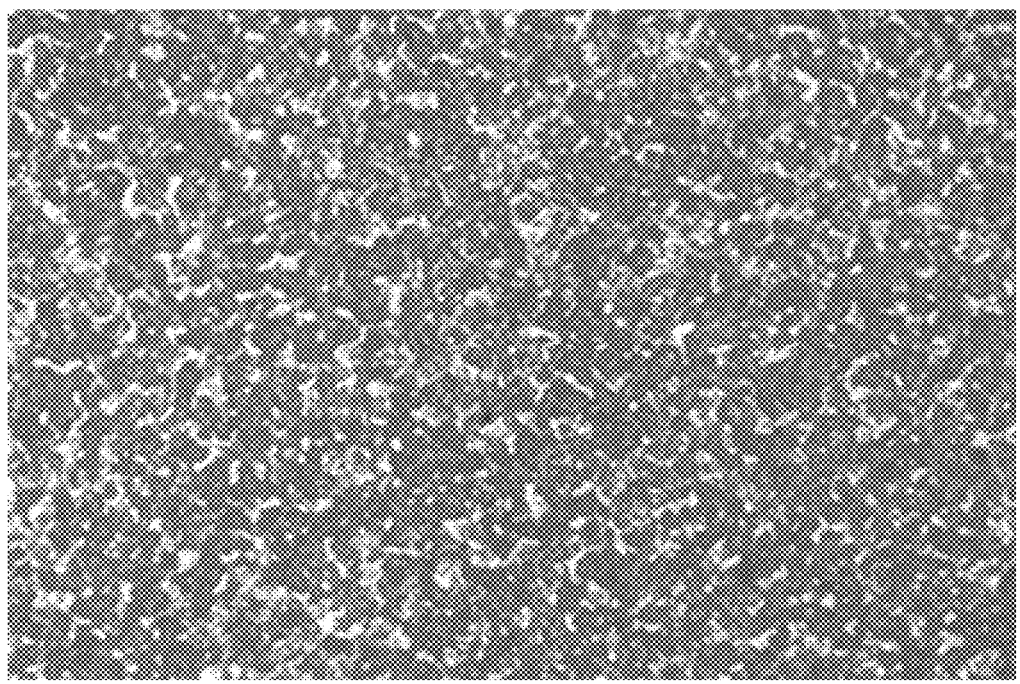
FIG. 5 is another micrograph of an exemplary embodiment of the delivery device using ultrasonic spray to deposit nalmefene on a film.

Micrographs of exemplary embodiments using ultrasonic spray to deposit nalmefene on a film are provided in FIGS. 4 and 5. The micrographs show amorphous drug-polymer clusters. FIG. 4 shows a single layer of an ultrasonic spray-coated film. FIG. 5 shows an embodiment wherein four passes of ultrasonic spray coating was used.

In embodiments, the method of manufacture may include a method of forming a continuous and uniform single layer active delivery device comprising domain polymer film and a pharmaceutical active composition, wherein the polymer film and the composition are substantially inseparable. For example, a delivery device can be constructed by preparing a polymer film comprising a wet polymer matrix and one of more of a permeation enhancer, pH adjusting buffer, taste masking agent, and/or flavor agent using a first solvent. A wet polymer film is formed by casting the wet polymer matrix. A drying apparatus can be used to dry the wet polymer matrix and expose the wet polymer film to a temperature sufficient to flash off the first solvent and thereby dry the polymer film as a continuous single layer film laminate. A second wet solution or suspension comprising a pharmaceutical active can then be prepared using a second solvent. A predetermined amount of the second wet solution can be applied via spraying, electro-spraying, atomized coating, ultra-thin web-coating processes, or dropwise deposition onto selected areas on a surface of the first dry polymer film. The second wet solution can be applied by continuous, constant, flow-controlled spraying. The film with the pharmaceutical active composition applied thereto is then dried in a drying apparatus and exposed to a temperature sufficient to flash off the second solvent to form a pharmaceutical active-containing delivery device. In some embodiments, the heating and drying temperature can range from about room temperature to about 250° C. For example, the temperature may be from about 50° C. to about 150° C.

In embodiments, the method of manufacture may include a method of forming a continuous and uniform single layer active delivery device comprising domain polymer film and a pharmaceutical active composition, wherein the pharmaceutical active composition is deposited dropwise onto the polymer film. For example, a delivery device can be constructed by preparing a polymer film comprising a wet polymer matrix and one of more of a permeation enhancer, pH adjusting buffer, taste masking agent, and/or flavor agent using a first solvent. A wet polymer film is formed by casting the wet polymer matrix. A drying apparatus can be used to dry the wet polymer matrix and expose the wet polymer film to a temperature sufficient to flash off the first solvent and thereby dry the polymer film as a continuous single layer film laminate. A second wet solution or suspension comprising a pharmaceutical active can then be prepared using a second solvent or continuous phase. A predetermined amount of the second wet solution is applied via dropwise deposition onto selected areas on a surface of the first dry polymer film. The film with the pharmaceutical active composition applied thereto is then dried in a drying apparatus and exposed to a temperature sufficient to flash off the second solvent to form a pharmaceutical active-containing delivery device. In some embodiments, the heating and drying temperature can range from about room temperature to about 250° C. For example, the temperature may be from about 50° C. to about 150° C.

In embodiments where the delivery device is a transmucosal single layer film device, the film delivery device can be prepared by procuring a dry, drug-free web-coated polymer matrix laminate roll from a suitable vendor (such as Lohmann Therapie Systeme (LTS), Tapemark Inc, Aquestive Therapeutics, Tesa GmbH, or ARx LLC). The second wet solution or suspension comprising a pharmaceutical active can then be prepared using a second solvent. A predetermined amount of the second wet solution or suspension can be applied onto selected areas of the surface of the dry polymer film by spraying, electro-spraying, atomized coating, and/or ultra-thin web-coating processes. The second wet solution can be applied by continuous, constant, flow-controlled spraying. The wet film with the pharmaceutical active composition applied thereto can then be deposited in a drying apparatus and exposed to a heating temperature sufficient to flash off the second solvent (e.g., about room temp to 250° C.) to form a pharmaceutical active-containing delivery device. In some embodiments, the pharmaceutical active composition comprising the pharmaceutical active is substantially thinner than the polymer film.

In some embodiments, the transmucosal single layer delivery device can be constructed by preparing a first wet polymer matrix and one or more of a permeation enhancer, pH adjusting buffer, taste masking agent, and/or a flavor using a first solvent. A first wet film can be formed by casting the wet polymer matrix. A second wet solution or suspension comprising the pharmaceutical active (or a salt thereof) and an oxygen scavenger and/or a drug solubilizer can be prepared in a second solvent. A predetermined amount of the second wet solution or suspension can then be applied on a surface of the first wet polymer film in a dropwise manner or in a manner to form a wet multi-domain film using spraying, electro-spraying, atomized coating, and/or ultra-thin web-coating processes. The wet multi-domain film can be deposited in a drying apparatus and exposed to a heating temperature sufficient to flash off the first and second solvents (e.g., about room temp to 250° C.) to form a delivery device comprising a polymer film and a pharmaceutical active composition. For example, the temperature may be from about 50° C. to about 150° C. In some embodiments, the pharmaceutical active composition is substantially thinner than the polymer film.

In some embodiments, the delivery device can be constructed by preparing a first wet polymer matrix and one or more of a permeation enhancer, pH adjusting buffer, taste masking agent, self-aggregating moiety (such as bentonite) and/or a flavor using a first solvent. A first wet film can be formed by casting the wet polymer matrix. The first wet polymer matrix can be deposited in a dryer apparatus and exposed to a temperature sufficient to flash off the first solvent to form a first dry film cast as a continuous single layer film laminate. A second wet solution or suspension comprising the pharmaceutical active (or a salt thereof) and optionally an oxygen scavenger and/or a drug solubilizer (such as a self-assembling phospholipid and/or bile salts) can then be prepared in a second solvent. A predetermined amount of the second wet solution or suspension can be applied on a surface (or onto selected areas of a surface) of the polymer film using a drop-wise method, spraying, electro-spraying, atomized coating, and/or ultra-thin web-coating processes. The second wet solution can be applied by continuous, constant, flow-controlled spraying The wet multi-domain film can be deposited in a drying apparatus and exposed to a heating temperature sufficient to flash off the first and/or second solvents (e.g., about room temp to 250° C.) to form a dry continuous single layer pharmaceutical active-containing delivery device. For example, the temperature may be from about 50° C. to about 150° C. In some embodiments, the pharmaceutical active composition is substantially thinner than the polymer film. Since the pharmaceutical active composition is applied on the surface of the film, and the enriched drug domain is not self-supporting, it can be created by rapid evaporation or flashing of the solvent. Such a process is different from conventional film manufacturing processes, which require controlled drying to maintained film integrity.

The delivery device can be configured in any desired form, such as (but not limited to) film strips, sheets, discs, wafers, and the like. The delivery device can have any desired thickness, such as about 50 to about 1000 μm, and preferably about 50 to 500 μm, although films with greater or lesser thicknesses are included within the scope of the presently disclosed subject matter. The delivery device can be configured in any desired shape, such as rectangular, square, rounded, triangular, abstract, and the like. It should be appreciated that the delivery device can have any desired thickness and/or size suitable for the intended use. For example, the delivery device can be a single-dosage sized unit that is to be placed into the oral cavity of the user.

The delivery device can be formed from a continuous roll of film or can be sized to a desired length and width.

An exemplary embodiment of a pharmaceutical active-containing transmucosal delivery device includes a delivery device comprising nalmefene. The delivery device comprising nalmefene can be used for treatment of or aid in treatment of opioid overdose.

Varying dose strengths are contemplated. For example, dosage strengths may include 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 37.5 mg, 40 mg, 50 mg, 60 mg, 75 mg, 100 mg, 150 mg of nalmefene in a pharmaceutical active composition.

The excipients contemplated for use in the compositions have been used in existing commercial products and are in the FDA's inactive ingredient database. The excipients include; hydroxy propyl methylcellulose USP, polyethylene oxide NF, sodium carboxy methyl cellulose NF, sodium saccharin USP, sorbitol NF, mannitol, blue FD&C dye, peppermint oil NF, monobasic sodium phosphate USP, dibasic sodium phosphate USP, PEG400 NF, glycerine USP, propylene glycol NF, ammonium glycyrrhizinate NF, Brij® O2, ethanol NF and water NF.

Another exemplary embodiment of a pharmaceutical active-containing transmucosal delivery device includes a delivery device comprising nalmefene for use in treating Prurigo Nodularis (PN), Chronic Liver disease associated Pruritus (CLD-aP) and Chronic Kidney Disease associated Pruritus (CKD-aP). Prurigo Nodularis is a chronic dermatologic condition characterized by severely pruritic nodules on the skin. Individuals suffering from Prurigo Nodularis usually have multiple excoriated lesions.

Intermittent moderate-to-severe-pruritus (itch) is a common comorbid symptom of chronic liver diseases, such as primary biliary cholangitis (PBC), primary sclerosing cholangitis (PSC), alcoholic liver disease (ALD), fatty liver disease (FLD), hepatitis (B/C), and liver cirrhosis. It is estimated that over 2.5 million patients suffer from intractable, persistent pruritus in liver disease patients with no FDA approved therapies currently available. Pruritus in liver disease is a refractory symptom that reduces the patient's quality of life (QOL) causing insomnia, anxiety, depression, nocturnal scratching, excoriation, and bleeding.

Pruritus is also common in atopic dermatitis (eczema), where 91% of the 15.6 million patients experience pruritus. However, despite new therapies to treat atopic dermatitis, approximately 31% do not find relief for their pruritus. Pruritus is common with patients suffering from chronic liver and kidney disease, which results in a 'scratch-itch' cycle that forms discrete, nodular, excoriated, hyperpigmented/purpuric lumps with scaly or crusted surfaces. Varying dose strengths are contemplated. For example, dosage strengths may include 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 37.5 mg, 40 mg, 50 mg, 60 mg, 75 mg, 100 mg, 150 mg of nalmefene in a pharmaceutical active composition.

The excipients contemplated for use in these compositions have been used in existing commercial products and are in the FDA's inactive ingredient database. The excipients include; hydroxy propyl methylcellulose USP, polyethylene oxide NF, sodium carboxy methyl cellulose NF, sodium saccharin USP, sorbitol NF, mannitol, blue FD&C dye, peppermint oil NF, monobasic sodium phosphate USP, dibasic sodium phosphate USP, PEG400 NF, glycerine USP, propylene glycol NF, ammonium glycyrrhizinate NF, Brij® O2, ethanol NF and water NF.

Exemplary films can be packaged in bulk in a zip-sealed, lined, opaque pouch containing 10 to 30 films per pouch, or in opaque, individual sealed chevron pouches that are 2.5 inches wide and 3.5 inches long. Each pouch can include 1 piece of SteriFlex 301 foil that has been heat sealed to 1 piece of 301P foil. The films can be stored at room temperature at 25° C. The heat seal width can be 0.25 inches, which would require a peel strength force of between 0.6 to 3.0 pounds to open the pouch. The pouch is opened by cutting with scissors below the heat seal.

After removal from the pouch, the delivery device can be administered buccally onto the inner lining of the cheek or sublingually (under the tongue). In case of the buccal administration, the enriched drug domain must be oriented to be in contact with the mucosa, while in the sublingual route, the film can be placed oriented up or down independent of directionality.

Unlike conventional oral film manufacturing, the active ingredient is not incorporated within the matrix of the polymer film or within the delivery device. Instead, the active composition is either sprayed, or deposited directly onto the surface of the polymer film, which does not have active incorporated therein. Upon rapid evaporation of the solvent in which the active ingredient is dissolved (in the pharmaceutical active composition), a compositional quench takes place thereby causing the active to phase separate in the binding polymer without undergoing nucleation and growth or Ostwald's ripening.

Typical methods of creating nanoparticles are complex, expensive, and time consuming. The typical processes are multi-step and are often challenged by particle agglomeration concerns. The described method circumvents these concerns by using a single step process wherein nano- or microparticles are created using an application method that prevents agglomeration of pharmaceutical active during application and are then subsequently locked-in-place on the surface of the polymer film.

Advantageously, the described method can be scaled for commercial use. Offering single-step manufacturing significantly reduces the costs-of-goods. Moreover, the described method provides advantageous uniformity and consistency to the manufacturing process. The manufacturing method consistently produces delivery devices having a dosage that is within 90%-110% of the target dosage. For example, for a target dosage of 3.75 mg, delivery devices made using the described method will have a dosage within the range of 3.375 mg to 4.125 mg. Uniformity and consistency in the manufacturing process provides efficiency in production time and raw material usage thus leading to cost savings, increased profitability and reduced production time.

In use, the described delivery device comprising the pharmaceutical active can be administered to a subject in need thereof. For example, the device comprising the polymer film and the pharmaceutical active (e.g., nalmefene) is placed under the tongue of a subject (e.g., in the sublingual or buccal space). The film rapidly sticks, disintegrates, and dissolves, allowing the nalmefene to dissolve and subsequently be absorbed directly into the bloodstream.

The pharmaceutical active resides at a high concentration in a molecular state in the microenvironment in immediate proximity of the subject's mucosa when administered. In this way, rapid transmucosal absorption of the pharmaceutical active is provided. In some embodiments, the rate of dissolution of the pharmaceutical active is significantly faster that the dissolution rate of the matrix.

In some embodiments, in acute or emergency situations of opioid overdose, the delivery device can be administered one or more times to a subject in need thereof. It should be appreciated that dosage can depend on many factors, such as severity of the condition, concentration of the nalmefene, weight of the subject, etc. The term "subject" as used herein refers to an animal, including primates (monkey, ape, human, etc.) or non-primate (cow, horse, pig, cat, dog, rat, mouse, bird, fish, etc.).

The transmucosal film can be administered buccally or sublingually to deliver about 1-32 mg of nalmefene to the subject. For example, in some embodiments, the nalmefene can be transmucosally administered at a dosage unit of about 1-5 mg one time as a part of emergency life-saving measures.

In this embodiment, the nalmefene is in an immediate release transmucosal dosage form administered through the buccal or sublingual route that provides in the patient an in vivo mean plasma concentration of at least 1 ng/ml within about 10 minutes after administration. For example, the dosage form may deliver an in vivo mean plasma concentration of at least 0.5 ng/mL nalmefene within 5 minutes after administration and/or at least 1 ng/mL nalmefene within 10 minutes after administration. The nalmefene may be in an immediate release transmucosal dosage form administered through the buccal or sublingual route that provides in the patient an in vivo mean $C_{max}$ from about 100-300 ng/mL. "$C_{max}$" refers to the maximum plasma, serum, or blood concentration of a drug (e.g., nalmefene or a pharmaceutically acceptable salt thereof) following administration.

The disclosed delivery device can be used to treat or aid in treatment of opioid overdose. To date, no oral transmucosal formulations of nalmefene exist for the treatment of this condition. As a result, the presently disclosed subject matter provides life-saving benefits to patients in need thereof.

In some embodiments, the delivery device can be administered about 1-2 times per day to a subject in need thereof. It should be appreciated that dosage can depend on many factors, such as severity of the condition, concentration of the nalmefene, weight of the subject, etc.

The transmucosal film can be administered buccally or sublingually to deliver about 1-32 mg of nalmefene to the subject. For example, in some embodiments, the nalmefene can be transmucosally administered at an initial dose of about 1-5 mg once or twice a day and then titrated to an effective dose (such as about 4-32 mg). In some embodiments, the nalmefene can be transmucosally administered with a first dosage at a first timepoint (e.g., in the morning) and a second dosage at a second timepoint (e.g., in the afternoon), wherein the first and second doses are equal or unequal.

The delivery device can be used to treat chronic liver and kidney disease-associated pruritus, cholestatic pruritus, and/or prurigo nodularis in a subject. To date, no oral transmucosal formulations of nalmefene exist for the treatment of these conditions. As a result, the presently disclosed subject matter provides life-changing relief to afflicted patients.

Due at least in part to the safe pharmacology of nalmefene and/or the suitable oral transmucosal route of administration, nalmefene has the potential to be the standard-of-care for the treatment of chronic pruritus, chronic kidney disease associated pruritus, and cholestatic pruritus.

The delivery device can provide effective taste masking, directional permeation, rapid absorption, and/or enhanced bioavailability of the pharmaceutical active. In some embodiments, the polymer film comprises a film-forming polymeric matrix, a pH adjusting buffer, taste masking agent, self-assembling phospholipid or bile salts, and/or a flavoring agent to provide effective taste masking and/or directional permeation. In some embodiments, the polymer film domain has slower rate of dissolution compared to the pharmaceutical composition domain.

Advantageously, the delivery device includes a plurality of discrete domains, where the at least one of the discrete domains is rich in pharmaceutical active or its salts thereof. Further, the delivery device includes single-layer film structures that comprise a plurality of discrete domains, wherein at least one of the domains is rich in pharmaceutical active or its salts thereof, and wherein the pharmaceutical active exists in a solid solution glassy, amorphous, microencapsulated or monomorphic crystalline microparticle state.

The disclosed single-layer film structure further includes at least one discrete domain that provides effective taste masking and/or enhanced transmucosal absorption when the discrete domain comprising the pharmaceutical active is placed in contact with the oral mucosa of a subject.

In embodiments, the delivery device may comprise a polymer film comprising a polymer matrix, and a pharmaceutical composition disposed on a surface of the polymer film, wherein the composition has a pH in a range of about 4 to about 9 and wherein the composition comprises nalmefene in the form of particles, and wherein the particles have an average particle size of about 100 nm to about 5 microns. The composition may further comprise an anti-crystallization agent, a pH adjusting agent, wherein the concentration of nalmefene is at least 20% w/w relative to the total weight of the pharmaceutical composition, and a binding polymer. The delivery device may exhibit a residence time in the mouth of a subject ranging from about 5 minutes to about 30 minutes and may be substantially mucoadhesive to a mucosal surface when placed sublingually under the tongue or placed buccally at the inner lining of the cheek.

The delivery device may further comprise a gelling agent. The nalmefene may attain a maximum plasma concentration in the subject in less than about 60 to about 120 min and have greater than 125% bioavailability as compared to the same active ingredient administered orally to the subject. The anti-crystallization agent may comprise a component selected from the group consisting of sorbitol, mannitol, and xylitol. The pH adjusting agent may comprise a component selected from the group consisting of phosphate buffers, acetate buffers, citrate buffers, arginine buffers, TRIS buffers, histidine buffers, ammonium glycyrrhizinate, and mixtures thereof.

The pharmaceutical composition may further comprise one or more components selected from the group consisting of a fast dissolving polymer, a self-assembling or self-aggregating moiety or components thereof, a dispersing agent, an oxygen scavenger, a drug solubilizing agent, a bioenhancer, a flavor agent, and a taste masking agent. The fast dissolving polymer may comprise a polymer that will dissolve in about 1 minute to about 3 minutes when placed in the mouth of a subject. The self-assembling or self-aggregating moiety may be selected from one or more of phospholipids, bile acids, bile salts, nano-platelet structures, divalent salts in combination with ionic hydrogel polymers, and edible clays. The self-assembling or self-aggregating moiety may comprise hydrophobic self-assembling moieties. The dispersing agent may comprise a component selected from the group consisting of Tween 20, Tween 80, Gelucire® 34/44, Kolliphor® HS 15, Solutol® NF, Labrafil® M2125 CS, Labrafil® M1944 CS, and mixtures thereof. The divalent salts may comprise calcium chloride, calcium citrate, calcium lactate or other Ca++, Mg++, Zn++ based GRAS acceptable salts and the ionic hydrogel polymer is sodium alginate or kappa carrageenan and mixtures thereof. The drug solubilizing agent or solubilizing solvent may comprise a component selected from the group consisting of ethanol NF, propylene glycol USP, glycerol USP, methanol, water and mixtures thereof. The dispersing agent and the drug solubilizing agent may comprise a solvent system for the pharmaceutical active ingredient and the solvent system comprises mixtures of one or more dispersing agents and one or more solubilizing agents. The solvent system may comprise one or more of ethanol, water, propylene glycol, Tween 20, Tween 80, Glycerine, Gelucire, Labrafil M2125 CS, and/or M1944 CS in varying ratios. The oxygen scavenger may be selected from one or more polyacids, polynucleic acids, proteins, polysaccharides, polypeptides, ethylenediamine tetraacetic acid (EDTA) and salts thereof, glutamic acid and salts thereof, citric acid and salts thereof, phosphonates, histidine, phytochelatin, hemoglobin, chlorophyll, humic acid, transferrin, desferroxamine, vitamin E acetate, tocopherol, and combinations thereof.

The taste masking agent may be selected from cellulose acetate, cellulose acetate butyrate, ethylcellulose, methylcellulose, and combinations thereof. The flavoring agent may be selected from oil of peppermint, menthol, oil of spearmint, vanilla, oil of cinnamon, oil of wintergreen, lemon oil, orange oil, grape oil, lime oil, grapefruit oil, apple, apricot essence, clove oil, anise oil, cardamom oil, coriander oil, *eucalyptus* oil, fennel oil, lemongrass oil, nutmeg oil, and combinations thereof. The pH of the pharmaceutical composition may be in a pH range of about 5 to about 8.

The polymer film may have a viscosity of about 10,000 cP to about 35,000 cP, including about 15,000 cP to about 25,000 cP, and about 18,000 cP to about 22,000 cP. The polymer matrix may comprise a film forming polymer and a mucoadhesive polymer. The film forming polymer may comprise water soluble, water swellable, and/or water erodible polymers. The polymer matrix may comprise hydroxy propyl methyl cellulose (HPMC), methyl cellulose, hydroxyethyl cellulose (HPC), hydroxypropyl cellulose, polyvinyl pyrrolidone, sodium carboxymethyl cellulose, polyethylene oxide (PEO), pullulan, alginic acid, sodium alginate, polyethylene glycol, pectins, xanthan gum, tragancanth gum, guar gum, acacia gum, arabic gum, locust bean gum, gellan gum, polyacrylic acid, polyacrylic acid crosslined with divinyl glycol, methyl methacrylate copolymer, carboxy vinyl copolymers, natural and hydrolyzed starch, gelatin type A and B, carrageenan, or combinations thereof. The polymer film may further comprise a permeation enhancer, a pH adjusting agent, a taste masking agent, and a flavoring agent. The permeation enhancer may be selected from one or more of lipophilic solvents, surfactants, menthols, fatty acid esters, and polyhydric alcohols. The pH adjusting agent may be selected from one or more of phosphate, acetate, citrate, arginine, TRIS, and histidine buffers.

The pH of the pharmaceutical active composition at the surface is independent of the pH of the polymer matrix. The pH of the pharmaceutical active composition may be different than or may be the same as the pH of the polymer matrix that constitutes the film. The taste masking agent may be selected from cellulose acetate, cellulose acetate butyrate, ethylcellulose, methylcellulose, and combinations thereof. The flavoring agent may be selected from oil of peppermint, menthol, oil of spearmint, vanilla, oil of cinnamon, oil of wintergreen, lemon oil, orange oil, grape oil, lime oil, grapefruit oil, apple, apricot essence, clove oil, anise oil, cardamom oil, coriander oil, *eucalyptus* oil, fennel oil, lemongrass oil, nutmeg oil, and combinations thereof.

Surfactants play an important role in procuring drop and spray droplet consistency. Surfactants such as tween 20, tween 40, tween 80, sodium docusate, n-dodecyl b-D maltoside, and ammonium glycyrrhizinate can be used. Critical micelle concentrations needed for each of the surfactants to ensure uniformity in droplet size and ability to wet the film layer once deposited on the surface of the film have been identified.

FIG. 6 is a line chart plotting interfacial tension in dyne/cm for three exemplary surfactants at different concentrations. FIG. 6 shows the concentrations at which consistent surface tension is enabled for each of the three exemplary surfactants. As can be seen, the data suggests that the concentration of surfactant that enables uniformity in surface tension was 0.1%, 0.75%, and 1.0% for n-dodecyl b-D maltoside, ammonium glycyrrhizinate and sodium docusate, respectively.

The delivery device may further comprise an intermediate layer disposed between the polymer film and the pharmaceutical active composition, the binding layer comprising a self-assembling or self-aggregating moiety, wherein the self-assembling or self-aggregating moiety is selected from one or more of phospholipids, bile acids, bile salts, nanoplatelet structures, and edible clays. The self-assembling or self-aggregating moiety may comprise hydrophobic self-assembling moieties.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1—Solvent Selection

Testing was performed to evaluate the solubility of nalmefene HCl at 100 mg/mL in solubility enhancing polar solvents and solubilizing agents. Ethanol, propylene glycol, glycerol, methanol, and water were considered. Table 1 shows the solubility evaluation observations.

TABLE 1

Solubility of Nalmefene in Polar Solvents

| Polar Solvent | Solubility of Nalmefene HCl Monohydrate | Test Concentration (mg/mL) |
| --- | --- | --- |
| Ethanol NF | Partially | 100 |
| Propylene glycol USP | Partially | 100 |
| Glycerol USP | Partially | 100 |
| Methanol | Highly | 100 |
| Water NF | Moderately high | 100 |

In addition, the solubility of nalmefene in varying concentrations was evaluated using different combinations of solvent systems. The solvent systems included combinations of polar solvents with different surface active agents. The solvent systems provided different volatilization rates. The solvent systems formed completely soluble, colorless pale beige solutions. Exemplary surface active agents included: Tween 20, Tween 80, Gelucire® 34/44, Kolliphor® HS 15, Solutol® NF, Labrafil® M2125 CS and Labrafil® M1944 CS.

TABLE 2

Solubility evaluation observations.

| ID | Solvent System | Ratio | Nalmefene Concentration (mg/mL) | Observation |
|---|---|---|---|---|
| 1 | Ethanol:Water | 75:25 | 200 | Completely Soluble, pale yellowish beige |
| 2 | Ethanol:Water:Tween 20 | 75:24.5:0.5 | 250 | Completely Soluble, pale yellowish beige |
| 2 | Ethanol:Water:Propylene Glycol | 82.5:12.5:5 | 200 | Completely Soluble, colorless to pale beige |
| 3 | Ethanol:Water:Propylene Glycol | 68:22:10 | 350 | Completely Soluble, yellowish beige |
| 5 | Ethanol:Water:Propylene Glycol:Tween 80 | 70:25:4:1 | 350 | Completely Soluble, yellowish beige |
| 6 | Ethanol:Water:Glycerine | 70:20:10 | 300 | Completely Soluble, yellowish beige |
| 7 | Ethanol:Water:Gelucire 34/14 | 75:20:5 | 200 | Completely Soluble, pale yellowish beige |
| 8 | Ethanol:Water:Labrafil M2125 OS | 80:17.5:2.5 | 200 | Completely Soluble, pale yellowish beige |
| 9 | Ethanol:Water:Labrafil M1944 CS | 80:17.5:2.5 | 200 | Completely Soluble, pale yellowish beige |

Example 2—Nalmefene Solubility

Figure 7:
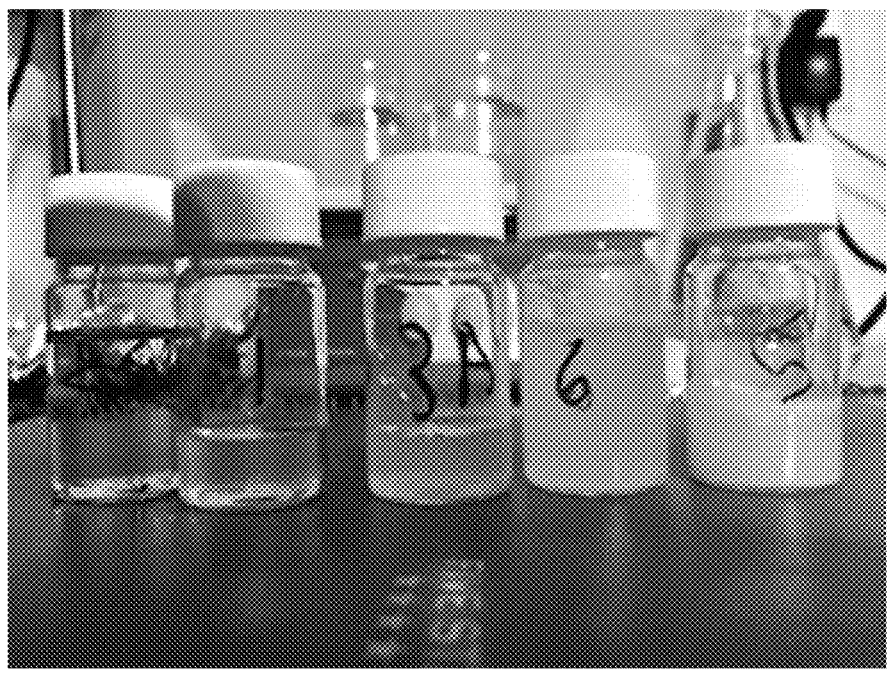
FIG. 7 is a photograph of samples at five tested pH levels.
Figure 8:
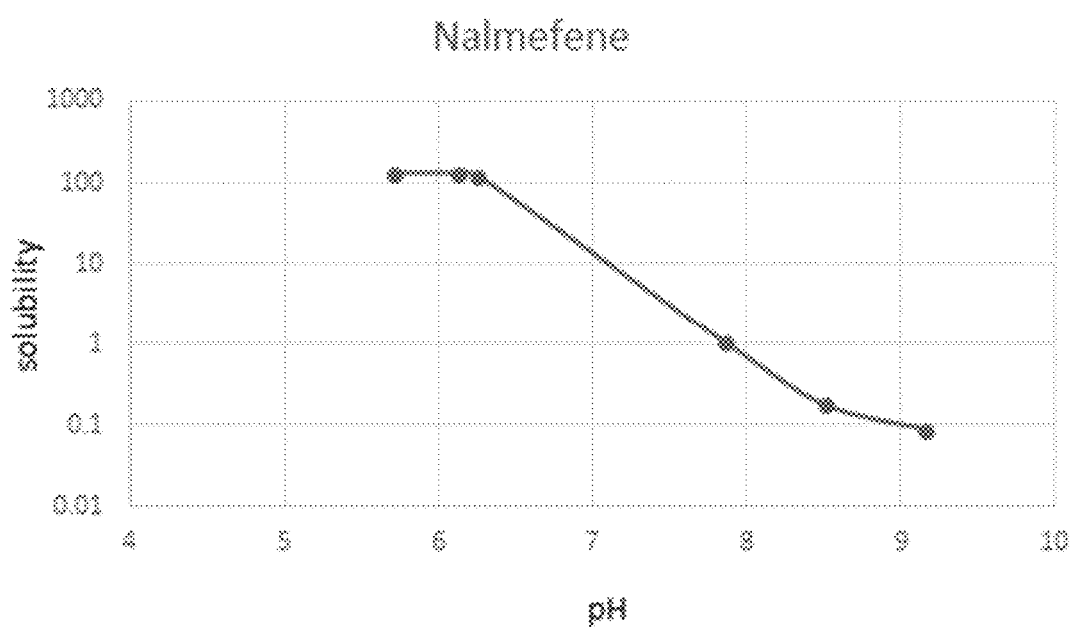
FIG. 8 is a chart of solubility data for nalmefene, which is provided in the Merck Index.

The solubility of nalmefene as a function of pH was evaluated. To determine the solubility of nalmefene, a visual assessment study (mimicking cloud point) was performed at five different pH conditions—pH 2.25, 4.0, 6.8, 8.0, 9.6 with 100 mg/mL. Experiments were conducted to determine the cloud point. FIG. 7 is a photograph of samples at the five tested pH levels. As shown, FIG. 7 illustrates the cloud point at various tested pH levels. From left to right, the pH of the aqueous media increased. An observed cloud point at 6.8 (vial 3A) demonstrated the solubility inflexion pH, which is consistent with data presented in the Merck Index, 19th Edition, (2001) for nalmefene. A chart of the solubility data provided in the Merck Index is shown in FIG. 8. Thus, a pH between 6 and 7.5 was defined as the two-phase boundary of nalmefene in suspension.

Example 3—Buffering Agents

Figure 9:
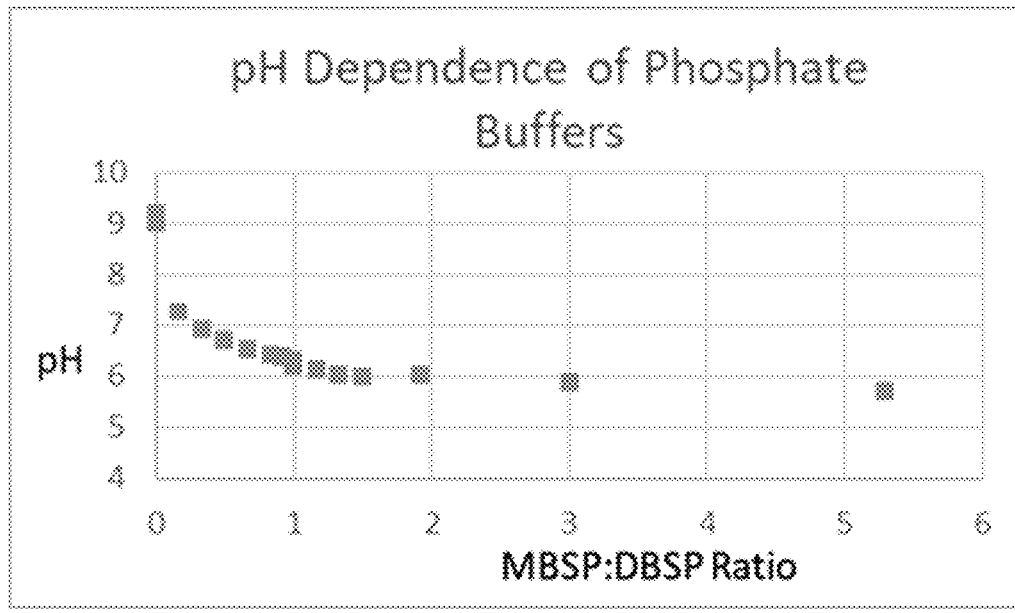
FIG. 9 is a graph showing pH control of exemplary buffering agent combinations that include combinations of monobasic sodium phosphate and dibasic sodium phosphate in varying ratios.

Testing was performed to evaluate buffer combinations for controlling pH of nalmefene in a range from 5.75 to 9. Combinations of monobasic sodium phosphate and dibasic sodium phosphate in varying concentration ratios were tested. The results are shown in FIG. 9.

Figure 10:
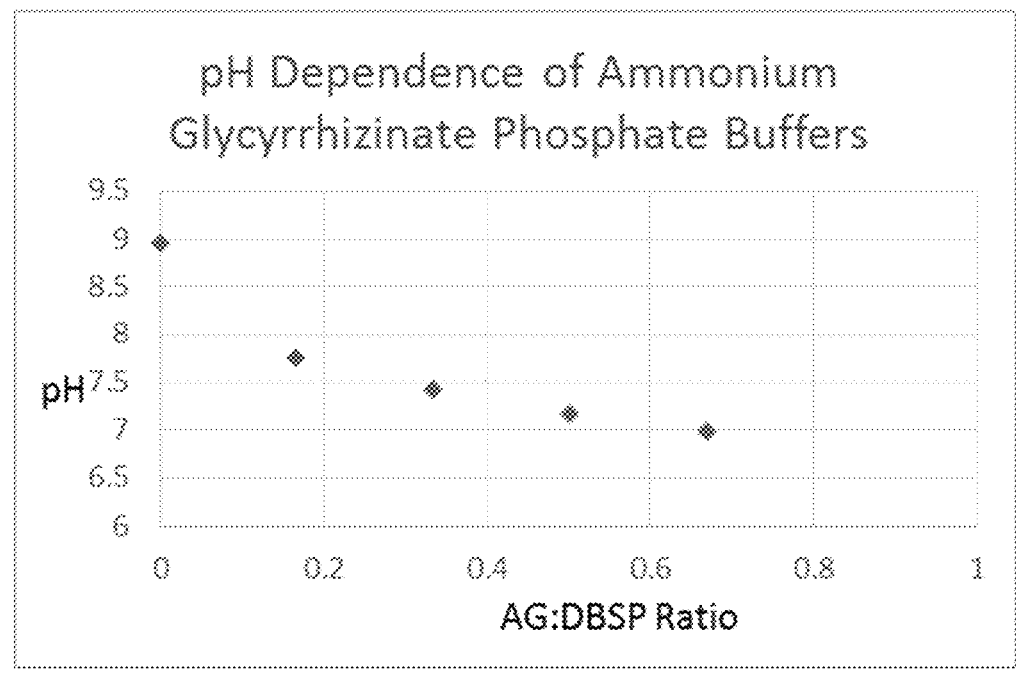
FIG. 10 is a graph showing pH control of exemplary buffering agent combinations that include combinations of ammonium glycyrrhizinate and dibasic sodium phosphate in varying ratios.

Surprisingly, it was determined that ammonium glycyrrhizinate, which is more conventionally used as a taste masking agent, can be used in combination with dibasic sodium phosphate as a suitable buffering agent in a buffering range between 6.25 and 9. FIG. 10 is a graph showing pH control of exemplary buffering agent combinations that include combinations of ammonium glycyrrhizinate and dibasic sodium phosphate in varying ratios. As can be seen, the combinations provided pH control at relatively high pH conditions. The buffer combination of ammonium glycyrrhizinate and dibasic sodium phosphate can be used to control pH at higher pH conditions, such as 7.0 or higher. pH dependency and surfactant properties are critical quality attributes for the describe delivery devices. The slope of ammonium glycyrrhizinate with dibasic sodium phosphate forms an excellent buffer that is more gradual at higher pH values in comparison to phosphate buffers. Thus, a delivery device comprising ammonium glycyrrhizinate can provide improved pH control while offering mucosal protection and improved taste masking.

Example 4. Method of Preparing Device

Films of desired thicknesses were created using conventional polymer matrices. The exemplary formulation in Table 3 is one such formulation. Table 3 provides the composition on a dry basis.

TABLE 3

Film Composition

| Material | Functionality | Example formula % w/w (dry) |
|---|---|---|
| Hypromellose 2910 HPMC E50, USP | Film Forming Polymer | 4-5.5% |
| HPMC K100LV | Film Forming Polymer | 35-43% |
| NaCMC 7L2P | Mucoadhesive Polymer | 17-22% |
| Peppermint Oil, NF | Flavorant | 3-6% |
| Vitamin E Acetate, USP | Antioxidant | 0.6-1% |
| Sodium Saccharin, USP | Sweetener | 1-2.5% |
| Sorbitol, NF | Humectant | 5.5-9% |
| Polyethylene glycol 400, NF | Plasticizer | 2.5-4% |
| Glycerin, USP | Humectant | 12.5-19% |
| Monobasic sodium phosphate, Anhyd, USP | pH adjusting buffer | 1-2% |
| Dibasic Sodium Phosphate, Anhyd. USP | pH adjusting buffer | 1-2% |
| Purified Water, USP | Solvent | n/a |

The film was designed with the following performance attributes: (1) the film hydrates slowly and remains in the mouth of a human with a residence time of about 6 minutes to about 10 minutes; (2) the film offers excellent mucoadhesion when placed on the cheek or under the tongue, as it cannot be dislodged after about less than one minute of application, (3) the film offers taste masking and palatability attributes, and (4) the film offer suitable pH control for maximization of drug absorption. The prepared films were approximately 130 micrometers in thickness (dry).

Subsequently, a pharmaceutical active composition was prepared. Table 4 provides the composition used for preparation of the exemplary pharmaceutical active composition.

TABLE 4

Drop Composition

| MATERIAL | FUNCTION | % WET |
|---|---|---|
| Nalmefene HCl monohydrate | Drug | 17-21% |
| Purified water USP | Solvent | 10-15% |
| Ethanol (190Proof), NF | Solvent | 46-70% |
| Sorbitol, NF | humectant | 0.2-0.4% |
| Mannitol, USP | humectant | 0.15-0.2% |
| Propylene glycol, USP | solubilizer | 0.8-1.3% |
| nDodecylβDmaltoside | surfactant | 0.12-0.2% |
| Sensient Blue #1 FD&C | colorant | 0.03-0.04% |
| Monobasic sodium phosphate, Anhy USP | buffer | 0.13-0.2% |
| Dibasic sodium phosphate, anhy, FCC | buffer | 0.15-0.2% |
| Peppermint Oil, NF | flavor | 0.18-0.3% |
| HPMC E5, NF | Polymer binder | 5.6-8.4% |
| Glycerol, NF | plasticizer/solubilizer | 0.5-0.9% |

Figure 11:
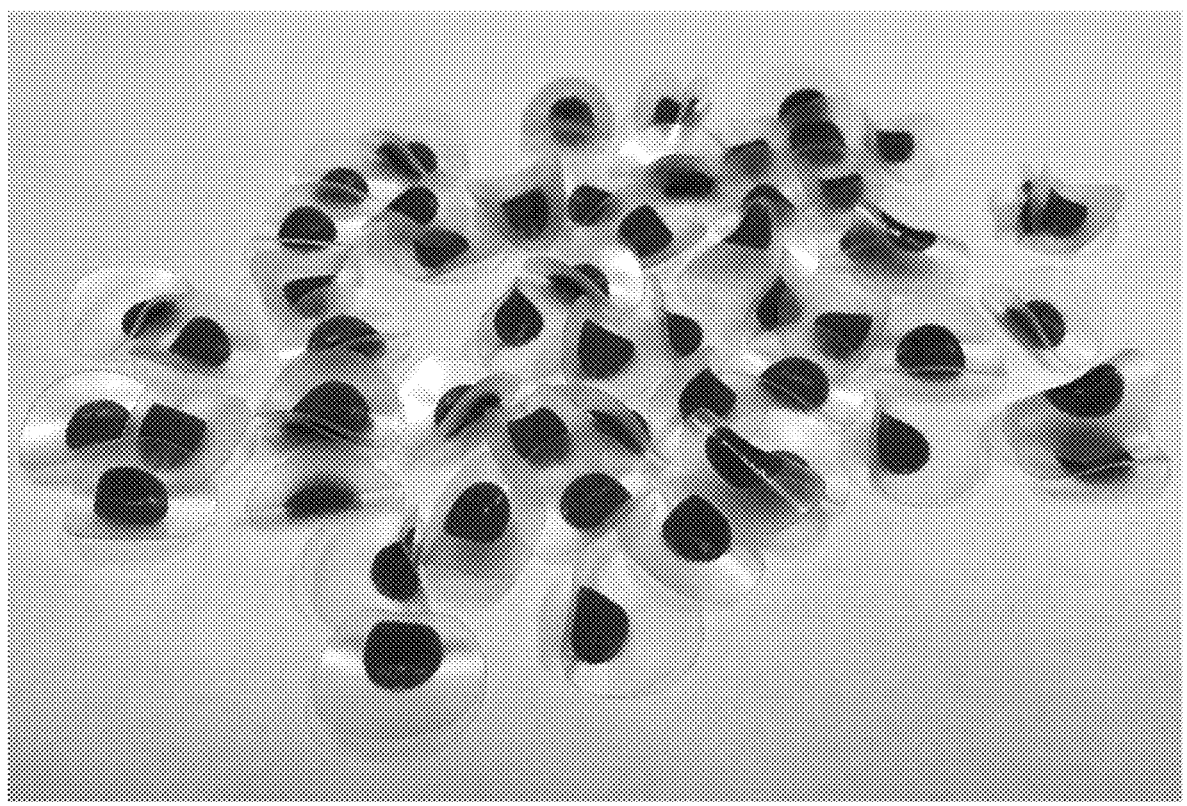
FIG. 11 is a photograph showing a representation of an exemplary dosage form.

Subsequently, the liquid composition provided in Table 4 was placed drop-by-drop on the surface of the film using a fixed 8G hypodermic needle at a flow rate of 0.4 mL/min. The drops were subsequently dried by conventional drying techniques. FIG. 11 is a photograph showing a representation of the created dosage form.

Example 5. Assessment of Surface Area

Testing was performed to assess the uniformity of drop diameter for an exemplary composition. A fixed 8G needle and a fixed flow rate of 0.4 mL/min were used. The composition was dropped onto a polymer film.

N=41 were used for each condition. Four drops were deposited at four distinct locations on the surface of the polymer films. The drops were dried for 36 hours and measured for their surface area. This was compared to the size of four drops placed on top of each other. The mean diameter (i.e. surface area) of the four drops placed separately was compared to four drops placed on top of each other.

Figure 12:
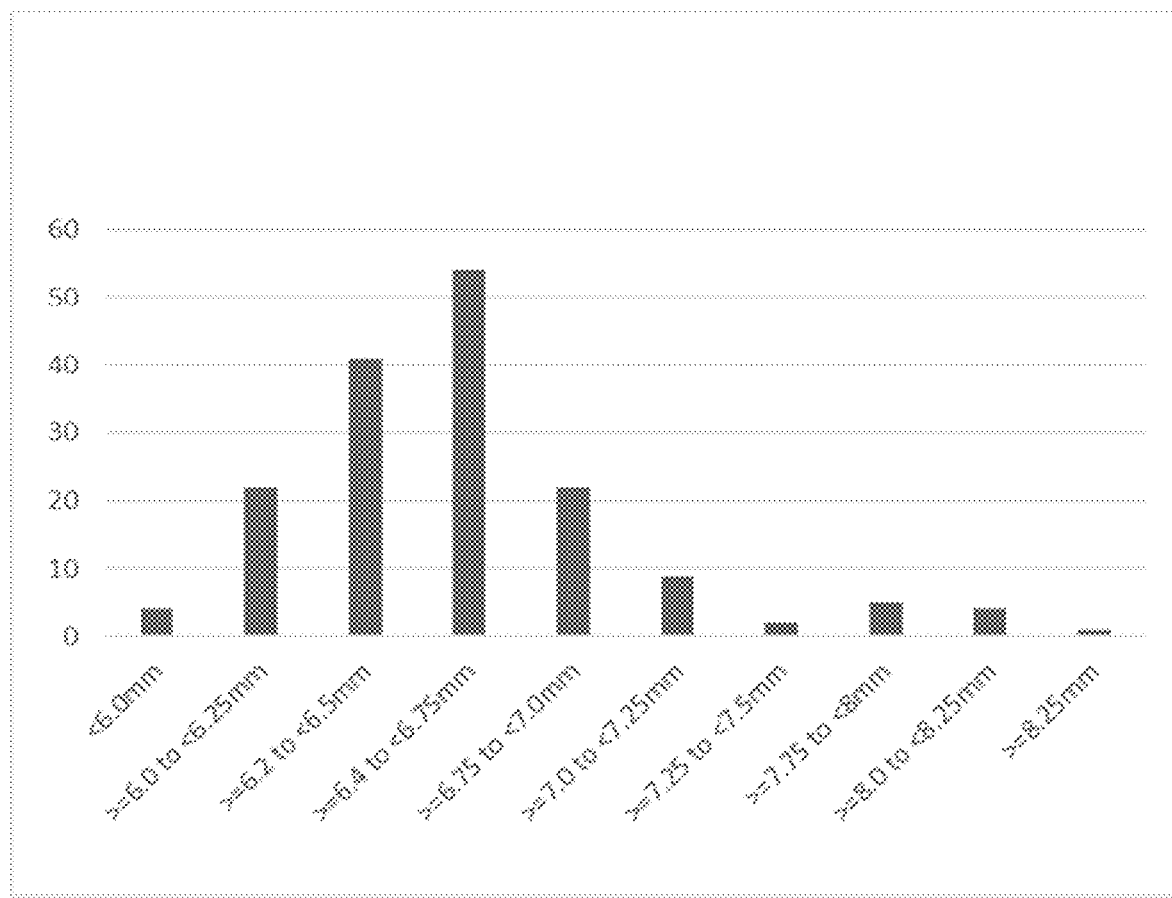
FIG. 12 is a chart showing results of a measured drop diameter test.

FIG. 12 shows the results of the measured drop diameter testing. As can be seen, the mean diameter and surface area for individual drops vary around a mean drop diameter of 6.610 mm with more variation around the minimum and maximum values of 5.7 and 8.18 mm. Variability in surface area may be mitigated by use of a shallow well of a fixed dimension that can be defined based on the viscosity and surface tension of the composition.

Example 6

Effect of Solvent Ratio on Drop Diameter

Testing was performed to ascertain the dimensions of a drop of composition on polymer film as an effect of dilution. Polymer film was manufactured, debossed, and cut into 4 cm$^2$.

Figure 13A:
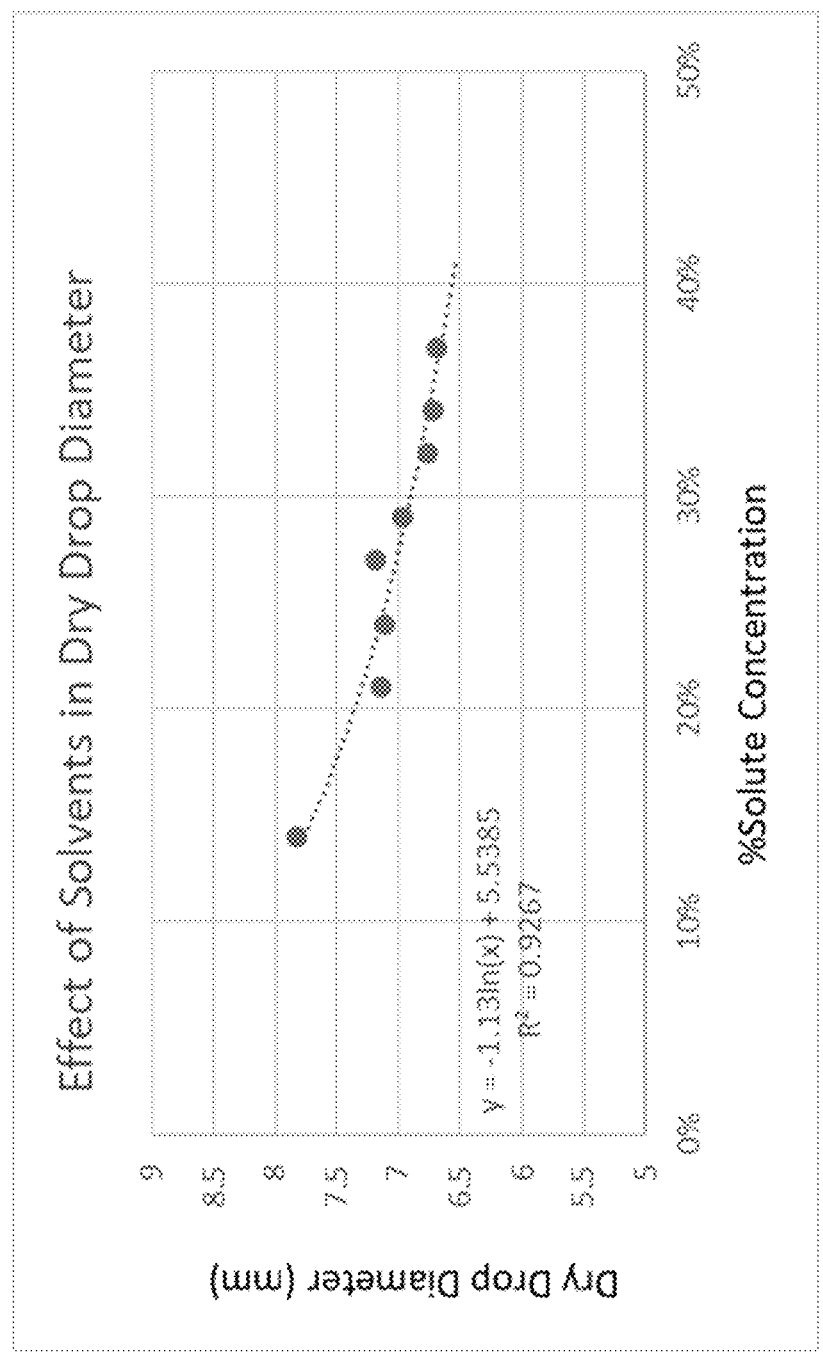
FIG. 13A is a chart showing the relationship between diameter and solute concentration for varying dilutions.
Figure 13B:
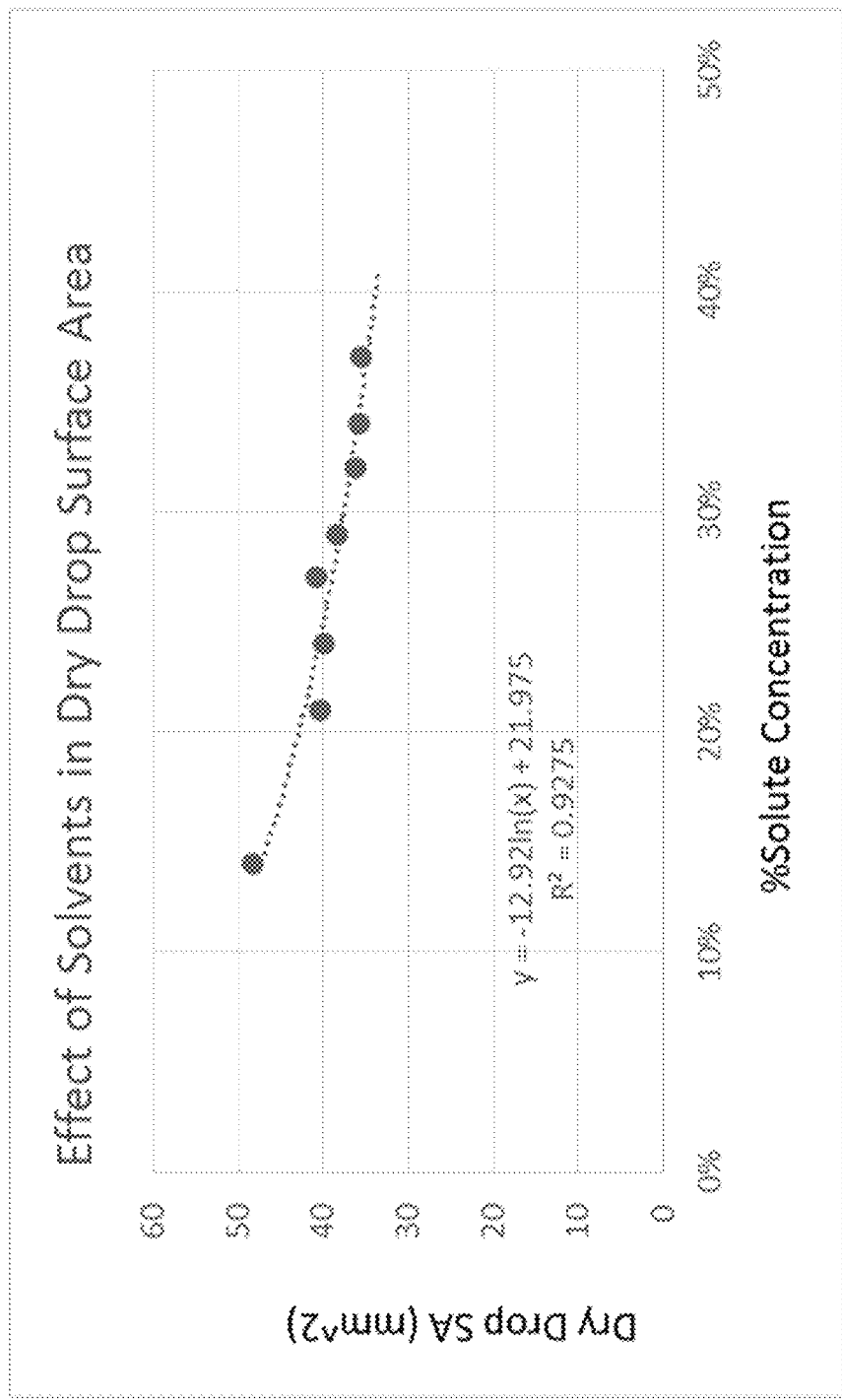
FIG. 13B is a chart showing the relationship between surface area and solute concentration for varying dilutions.
Figure 22:
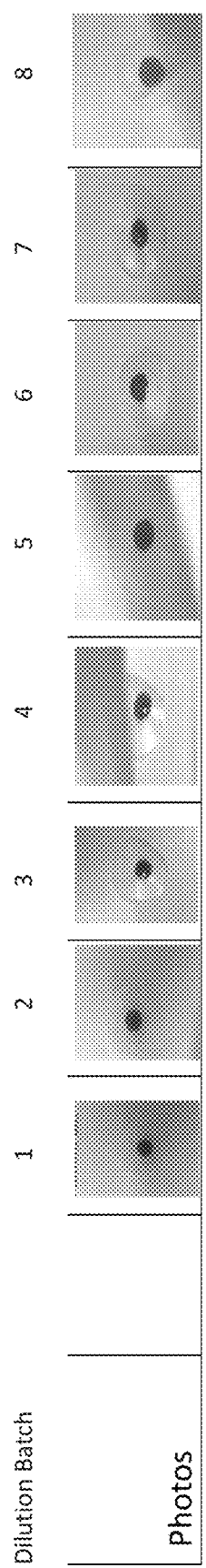
FIG. 22 is series of photographs accompanying Table 5, which depicts the conditions of a representative sample of each dilution in the Table.

Using the standard solvent ratio of the present formulation, each sample was diluted from 10% to as high as a 200% dilution. After each condition was created, 2 drops were deposited onto debossed sublingual films (n=25) and allowed to dry under conventional drying conditions. Diameter size from N=25 was captured as a function of sequential dilutions. Table 5 and FIGS. 13A and 13B present the diameter and surface area relation with respective to dilutions. As can be seen, as dilution increased, the surface area of the droplet increased. Table 5 depicts the conditions of a representative sample of each dilution. FIG. 22 is a series of photographs of a representative sample of each dilution.

TABLE 5

Representation of the Film with Dilution

| | | Dilution Batch | | | | | | | |
|---|---|---|---|---|---|---|---|---|---|
| | | 1 | 2 | 3 | 4 | 5 | 6 | 7 | 8 |
| Dilution | CONTROL | 10% | 20% | 30% | 40% | 50% | 70% | 100% | 200% |
| Solute Conc | 41% | 37% | 34% | 32% | 29% | 27% | 24% | 21% | 14% |

FIG. 13A shows that as the dilution increases (i.e. decrease in solute concentration), dry drop diameter increases exponentially. The logarithm correlation is plotted above which allows predicting and verifying the drop diameter. Based on this graph, the exemplary formulation is predicted to have a mean dry drop diameter according to the following formula:

$$Y = -1.13 \ln(41.1\%) + 5.5385 = 6.5432 \text{ mm, with an } R^2 = 0.9267.$$

A similar assessment of the surface area was performed. The results are shown in FIG. 13B.

Example 7. Assessment of Dry Drop Weight

Dry drop weight using an exemplary formulation using a fixed 8G needle was assessed for process control uniformity in drop deposition.

An exemplary formulation was created and dropped on a pan and on the surface of exemplary polymer films. N=30 were used for each condition. The drops were dried for 36 hours and the weight of dry drop within each pan was recorded and plotted as a function of number of drops (as N=30 for each condition) in FIG. 14. The reported standard deviation was less than 1.0%.

Figure 14:
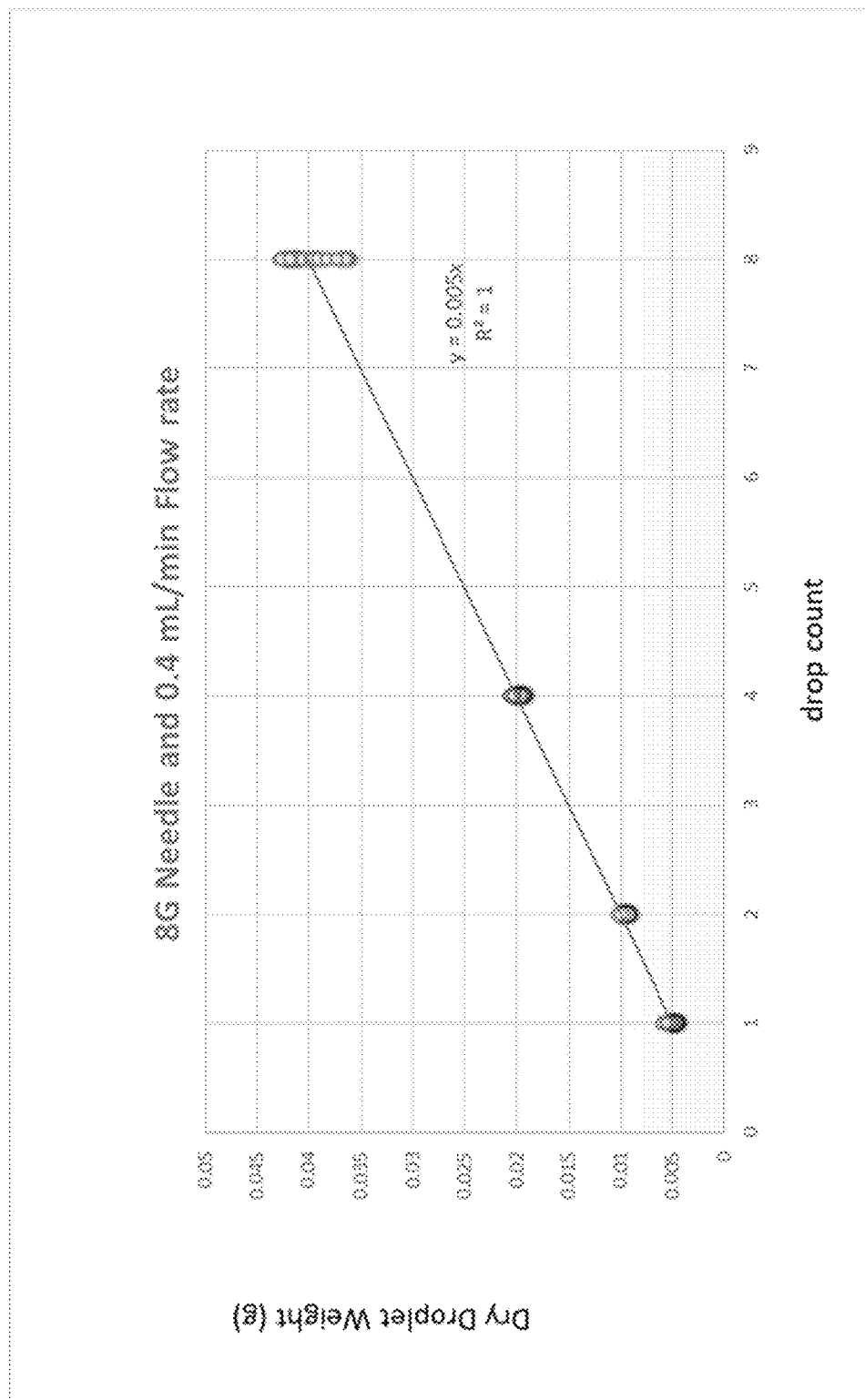
FIG. 14 is a chart plotting the weight of dry drop as a function of number of drops (as N=30 for each condition) in Example 7.

Excellent droplet proportionality was observed from 1 to 8 drops using a 8G needle and at a flow rate of 0.4 mL/min. In the testing, the standard deviation on low drop count was better than high drop count. This result may be attributed to variability in loss on drying and product wettability (as shown in FIG. 14).

Example 8

The effects of varying droplet nozzle size were assessed. Droplet nozzle sizes of 8G, 10G, and 14G were evaluated. Flow rates of 0.4 ml/min and 1.0 ml/min were used. Number of drops, mean drop weight and associated variability were considered. The results are shown below in Table 6.

TABLE 6

Number of drops, mean drop weight and associated variability

| Nozzle Gauge | Solution Flow Rate (ml/min) | Number of Drops | Mean Weight (mg) n = 10 | % RSD | Mean Weight per Drop (mg) |
|---|---|---|---|---|---|
| 8 | 0.4 | 1 | 10.86 | 2.54 | 10.86 |
| | | 3 | 29.37 | 1.43 | 9.79 |
| | | 5 | 47.93 | 1.29 | 9.59 |

TABLE 6-continued

Number of drops, mean drop weight and associated variability

| Nozzle Gauge | Solution Flow Rate (ml/min) | Number of Drops | Mean Weight (mg) n = 10 | % RSD | Mean Weight per Drop (mg) |
|---|---|---|---|---|---|
| | 1 | 1 | 11.29 | 1.76 | 11.29 |
| | | 3 | 31.35 | 0.81 | 10.45 |
| | | 5 | 50.72 | 1.24 | 10.14 |
| 10 | 0.4 | 1 | 10.18 | 3.29 | 10.18 |
| | | 3 | 26.2 | 1.5 | 8.73 |
| | | 5 | 41.35 | 1.13 | 8.27 |
| | 1 | 1 | 10.03 | 2.85 | 10.03 |
| | | 3 | 27.39 | 2.21 | 8.73 |
| | | 5 | 43.48 | 0.86 | 8.27 |
| 14 | 0.4 | 1 | 6.88 | 9.39 | 6.88 |
| | | 3 | 16.98 | 1.95 | 5.66 |
| | | 5 | 28.17 | 3.09 | 5.63 |
| | 1 | 1 | 6.95 | 10.47 | 6.95 |
| | | 3 | 17.68889 | 2.06 | 5.9 |
| | | 5 | 28.32 | 2.80 | 5.66 |

The 8-gauge nozzle appeared to deliver the most consistent droplet weight. It appeared that the solution flow rates of 0.4 ml/min and 1 ml/min were not significantly different.

Example 9

A drop study was conducted to assess content uniformity of deposited drops and actual drop weight uniformity for a varying amount of drops (1, 2, 3 and 4 drops). A series of 10 tests were run. The results are shown below in Table 7. As can be seen, the uniformity results for all examples were favorable.

| | 1 drop (assigned LC = 4 mg/film) | | 2 drops (assigned LC = 8 mg/film) | | 3 drops (assigned LC = 12 mg/film) | | 4 drops (assigned LC = 16 mg/film) | |
|---|---|---|---|---|---|---|---|---|
| prep # | % LC | weight (mg) | % LC | weight (mg) | % LC | weight (mg) | % LC | weight (mg) |
| 1 | 102.4 | 7.856 | 102.1 | 15.794 | 99.1 | 23.027 | 100.9 | 31.174 |
| 2 | 101.2 | 7.849 | 103.7 | 15.977 | 99.5 | 22.933 | 100.7 | 31.151 |
| 3 | 101.1 | 7.751 | 102.4 | 15.805 | 99.1 | 22.929 | 100.4 | 30.945 |
| 4 | 101.8 | 7.798 | 102.3 | 15.749 | 99.5 | 22.979 | 101.1 | 31.174 |
| 5 | 101.5 | 7.755 | 102.1 | 15.682 | 97.1 | 22.229 | 101.2 | 31.073 |
| 6 | 102.1 | 7.839 | 103.1 | 15.748 | 97.7 | 22.624 | 101.6 | 30.887 |
| 7 | 101.1 | 7.755 | 103.2 | 15.741 | 97.5 | 22.442 | 100.7 | 30.575 |
| 8 | 100.2 | 7.693 | 103.5 | 15.843 | 99.3 | 22.888 | 100.9 | 30.832 |
| 9 | 100.2 | 7.686 | 103.1 | 15.689 | 98.5 | 22.726 | 101.0 | 30.627 |
| 10 | 101.0 | 7.760 | 103.2 | 15.603 | 98.9 | 22.840 | 100.9 | 30.531 |
| Mean | 101.3 | 7.77 | 102.9 | 15.76 | 98.6 | 22.76 | 100.9 | 30.90 |
| % RSD | 0.7 | 0.8 | 0.6 | 0.6 | 0.9 | 1.1 | 0.3 | 0.8 |
| AV | 1.7 | (Limit = 15) | 2.8 | (Limit = 15) | 2.1 | (Limit = 15) | 0.8 | (Limit = 15) |

Example 10

Figure 15:
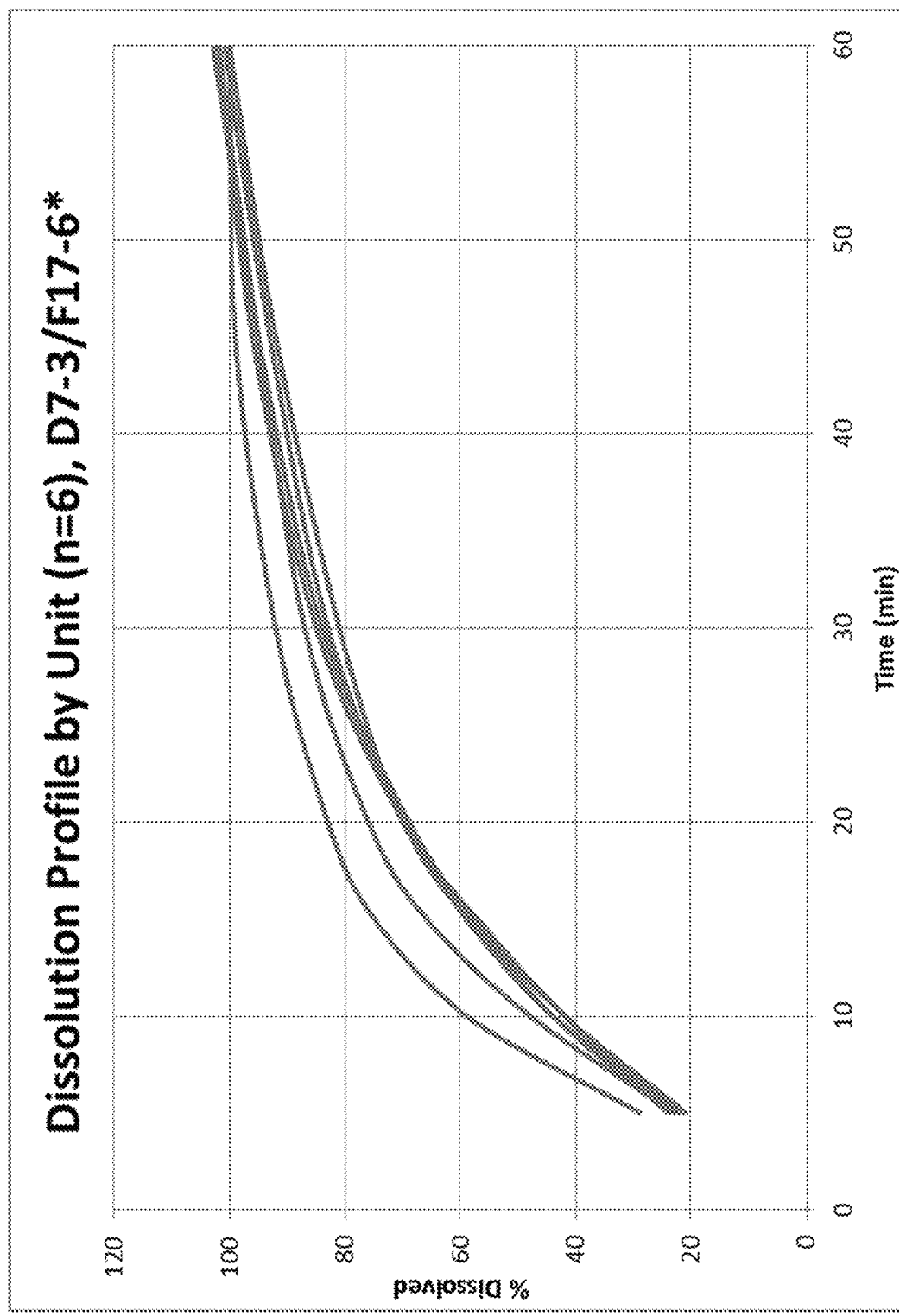
FIG. 15 is a chart showing a dissolution profile for an exemplary pharmaceutical active containing transmucosal delivery device.

An exemplary delivery device was tested using USP 711 tests. The device demonstrated very consistent release in N=6 films reflecting a profile where greater than 80% was released in 30 minutes, as shown in FIG. 15.

Example 11—Excipients for Pharmaceutical Active Compositions

Exemplary compositions including varying components were considered and evaluated. Varying anticrystallization agents for reducing and/or preventing nucleation and growth of the active in an oral film dosage form were considered. Additionally, excipients affecting residence time in the mouth with suitable mucoadhesive and pH attributes were considered. Residence times may range from about 1 minute to about 30 minutes, such as for example about 5 minutes to about 10 minutes. Additionally, divalent calcium ions that instantaneously gel sodium alginate thereby preventing active migration into the polymer film was tested. Moreover, different flavoring agents and/or taste masking agents were tested.

Exemplary formulations having varying selections of polymers, molecular weights, and polymer ratios were prepared. Additionally, exemplary formulations were prepared having varying selections and amounts of flavoring agents, coloring agents, taste masking agents, sweeteners, plasticizers, humectants, bioenhancers, and buffering agents.

A summary of components, amounts, and compositional relationships for exemplary compositions is provided in Table 3.

TABLE 8

Summary of components, amounts, and compositional relationships

| Functionality | Exemplary Ingredient | Amount Range (mg) | Compositional Relationship |
|---|---|---|---|
| Drug | Nalmefene HCl monohydrate | 1 to 75 mg | 10 to 90% of drug in the delivery device composition, 20% concentration or higher at the surface of the film |
| Anticrystallization agent(s) (AC) | Sorbitol, mannitol | 0.5 to 25 mg | Ratio range of AC agent:drug of 1:1.5 to 1:20 |
| Polymer(s) | Aquaion NaCMC, Low and medium MW PEO, and Low and Medium MW HPMC | 25 to 250 mg | 10 to 90% of polymer in the delivery device composition |
| Bioenhancer, | docusate sodium USP and Brij O2 | 0.1 to 15 mg | <5% in the delivery device composition |

TABLE 8-continued

Summary of components, amounts, and compositional relationships

| Functionality | Exemplary Ingredient | Amount Range (mg) | Compositional Relationship |
|---|---|---|---|
| pH adjusting agent(s) | monobasic sodium phosphate, dibasic sodium phosphate, ammonium glycyrrhizinate | 0.5 to 20 mg | <5% in the delivery device composition |
| Salt gelling agent | Calcium chloride, USP | 0.05 to 5 mg | <2% in the delivery device composition, calcium chloride: sodium alginate ratio ranges from 1:10 to 10:1 |
| Barrier polymer | Sodium Alginate, NF | 0.1 to 50 mg | <2% in the delivery device composition |
| Additional excipients | Peppermint Oil, Blue FD&C, sodium saccharin, glycerin | 0.2 to 50 mg | <1 to 20% in the delivery device composition |

Additional exemplary compositions using different drug concentrations are shown below in Table 9.

| Material | Functionality | Example 1 weight (mg) | Example 2 weight (mg) | Example 3 weight (mg) |
|---|---|---|---|---|
| Nalmefene HCl monohydrate | Drug | 4.350 | 8.700 | 17.415 |
| Sorbitol, NF | Anticrystallization agent | 5-10 | 5-10 | 5-10 |
| Mannitol NF | Anticrystallization agent | 0.01-1 | 0.01-1 | 0.01-1 |
| Glycerin, USP | plasticizer | 5-10 | 5-10 | 5-10 |
| Docusate sodium USP or Brij O2 | bioenhancer | 0.01-1 | 0.01-1 | 0.01-1 |
| Peppermint Oil, NF | flavor | 1-10 | 1-10 | 1-10 |
| Blue FD&C | colorant | 0.01-1 | 0.01-1 | 0.01-1 |
| HPLC, Vivapharm E5, NF | Polymer binder | 0.1-2 | 0.1-2 | 0.1-2 |
| Calcium chloride, USP | Salt gelling agent | 0.01-1 | 0.01-1 | 0.01-1 |
| Polyox N10 | Polymer binder | 0.1-2 | 0.1-2 | 0.1-2 |
| Benecel HPMC K100LV | Film Forming Polymer | 10-60 | 10-60 | 10-60 |
| Aquaion NaCMC 7L2P | Mucoadhesive Polymer | 10-60 | 10-60 | 10-60 |
| Sodium Alginate, NF | Barrier Polymer | 0.01-1 | 0.01-1 | 0.01-1 |
| Sodium Saccharin, USP | Sweetener | 0.5-3 | 0.5-3 | 0.5-3 |
| Polyethylene glycol 400, NF | Plasticizer | 0.5-3 | 0.5-3 | 0.5-3 |
| Monobasic sod phosphate, anhydrous | pH adjusting buffer | 0.5-3 | 0.5-3 | 0.5-3 |
| Dibasic Sod. Phosphate, USP | pH adjusting buffer | 0.5-3 | 0.5-3 | 0.5-3 |
| Total | | 90-120 | 90-120 | 90-120 |

Example 12—Testing Three Exemplary Delivery Devices

As will be described in greater detail below, nalmefene composition formulations were prepared and tested with three exemplary delivery devices. The delivery devices included rapidly-dissolving, oral mucoadhesive buccal films with uniformly distributed nalmefene nano- and microparticles residing on the surface of the film. The exemplary delivery devices included nalmefene formulations having a target dosage unit of 4 mg nalmefene. The three exemplary devices were prepared as follows:
1) using a high-precision ultrasonic spray at pH of 6.8, mannitol (anticrystallization agent) and ammonium glycyrrhizinate NF (CMC=0.11 mM and Mw=840 g/mol),
2) using a single liquid drop method at a pH of 7.0, mannitol (anticrystallization agent) and n-dodecyl β-D maltoside (CMC=0.15 mM and Mw=511 g/mol), and
3) using a single liquid drop method at a pH of 6.5, mannitol (anticrystallization agent), and sodium docusate NF (CMC=0.6 mM and Mw=444.55).

Table 10 provides a summary of the Formulations.

| Material | Function | Nalmefene Buccal Film F1 Wt(g) | Nalmefene Buccal Film F2 Wt(g) | Nalmefene Buccal Film F3 Wt(g) |
|---|---|---|---|---|
| Film laminate | | | | |
| Hypromellose HPMC E50 | film forming polymer | 0-2 | 3-4 | 3-4 |
| HPMC K100LV | film forming polymer | 25-31 | 25-32 | 25-32 |

| Material | Function | Nalmefene Buccal Film F1 Wt(g) | Nalmefene Buccal Film F2 Wt(g) | Nalmefene Buccal Film F3 Wt(g) |
|---|---|---|---|---|
| NaCMC 7L2P | mucoadhesive polymer | 12-16 | 12-16 | 12-16 |
| Peppermint Oil | flavorant | 2.5-4.5 | 2.5-4.5 | 2.5-4.5 |
| Vitamin E Acetate | antioxidant | 0-0.4 | 0.4-0.7 | 0-0.4 |
| Sodium Saccharin | sweetener | 1-2 | 1-2 | 1-2 |
| Sorbitol | humectant | 4-6.5 | 4-6.5 | 4-6.5 |
| Polyethylene glycol 400 | plasticizer | 1.5-3 | 1.5-3 | 1.5-3 |
| glycerin | humectant | 4.5-7 | 9-14 | 9-14 |
| Monobasic sodium phosphate, anhydrous | pH adjusting buffer | 0.8-1.4 | 0.8-1.4 | 0.8-1.4 |
| Dibasic sodium phosphate, anhydrous | pH adjusting buffer | 1-1.5 | 1-1.5 | 1-1.5 |
| Active Formulation | | | | |
| Nalmefene HCl | drug | 3.8-5 | 3.8-5 | 3.8-5 |
| sorbitol | Humectant | 0.05-0.15 | 0.05-0.15 | 0.05-0.15 |
| mannitol | Humectant | 0.03-0.05 | 0.03-0.05 | 0.03-0.05 |
| propylene glycol | Solubilizer | 0.2-0.3 | 0.2-0.3 | 0.2-0.3 |
| ndodecylβDmaltoside | Surfactant | 0-0.02 | 0.02-0.04 | 0-0.02 |
| ammonium glycyrrizhinate | Surfactant | 0.02-0.04 | 0-0.02 | 0-0.02 |
| sodium docusate | Surfactant | 0-0.02 | 0-0.02 | 0.02-0.04 |
| sensient blue | Colorant | 0.007-0.011 | 0.007-0.011 | 0.007-0.011 |
| monobasic sodium phosphate | Buffer | 0 | 0.03-0.05 | 0.03-0.05 |
| dibasic sodium phosphate | Buffer | 0.03-0.053 | 0.03-0.053 | 0.03-0.053 |
| peppermint oil | Flavor | 0.1-0.2 | 0.1-0.2 | 0.1-0.2 |
| Hypromellose HPMC E5 | Polymer binder | 1.3-2 | 1.3-2 | 1.3-2 |
| glycerin | Plasticizer/solubilizer | 0.13-0.21 | 0.13-0.21 | 0.13-0.21 |

The exemplary delivery devices were tested to assess the pharmacokinetics, safety, and tolerability in a beagle dog model.

All three exemplary nalmefene delivery devices showed excellent bioavailability in comparison to commercially available nalmefene IV dose. Notably, each of the three exemplary nalmefene delivery devices reached a target plasma concentration of greater than 1 ng/mL in less than 10 min. Formulation 1 reached mean plasma concentrations of 7.39 ng/mL, 1.07 ng/mL, and 0.237 ng/mL at 10, 5, and 2.5 min, respectively. Formulation 2 reached mean plasma concentrations of 4.54 ng/mL, 0.726 ng/mL, and no detectable levels at 10, 5, and 2.5 min, respectively. Formulation 3 reached mean plasma concentrations of 3.94 ng/mL, 0.346 ng/mL, and 0.025 ng/mL at the 10, 5, and 2.5 min, respectively. Furthermore, the rescue levels of nalmefene were maintained for at least 4 hr for each formulation and only dropped below 1 ng/mL between the 4 and 8 hr collection times.

Formulation 1 demonstrated the highest blood level of nalmefene of 1.07 ng/mL at 5 min post-administration, compared to concentrations of 0.726 and 0.346 ng/mL for formulations 2 and 3 at 5 min, respectively.

Drug Substance/Active Ingredient

The drug substance used in the exemplary delivery devices was Nalmefene hydrochloride (CAS #58895-64-0). Nalmefene hydrochloride is available as a white to off-white crystalline powder, which is freely soluble in water up to 130 mg/mL and slightly soluble in chloroform up to 0.13 mg/mL. Nalmefene hydrochloride exhibits two dissolution constants, pKa1=8.38 (amine); pKa2=10.00 (phenol), and a log P is 2.66.

Additional Components

Different kinds and amounts of flavor, sweeteners, antioxidants, and polymers were evaluated. The two polymers used in the film formulations were sodium carboxymethylcellulose (Aqualon NaCMC 7L2P) and different molecular weights of hydroxypropyl methylcellulose (HPMC). These polymers provide a balance between mucoadhesive attributes of the film sticking to the buccal mucosa and film-forming characteristics for blend processing. Phosphate buffers were used to control pH. Additionally and unexpectedly, ammonium glycyrrhizinate NF was used to control pH and provide taste masking. The delivery devices also included antioxidants to provide better oxidative stability for the flavor during shelf life.

The exemplary delivery devices were able to adhere immediately when placed against the buccal mucosa with a residence time of approximately 8 to 10 min.

Pharmacokinetic Analysis

A pharmacokinetic study in N=12 beagle dogs was conducted where the three nalmefene buccal film formulations were assessed along with a nalmefene IV 4 mg control using an open-label, Latin-square design. Blood plasma was collected at t=0, 2.5 min, 5 min, 10 min, 15 min, 30 min, 1 h, 2 h, 4 h, 8 h, 12 h and 24 h, and nalmefene and metabolite concentrations were determined by LC/MS.

Dogs, (n=6/sex/dose) were treated in a Latin Square design as follows through four dosing periods. The purpose of the study was to determine the pharmacokinetic profiles of nalmefene and a metabolite, nornalmefene, after administration of three unique buccal film formulations or administration of intravenous nalmefene doses to dogs. This study was conducted in accordance with standard operating procedures (SOPs). All procedures were in compliance with the Animal Welfare Act Regulations (9 CFR 3). The test articles used in the study are provided in Table 11A. Table 11B shows the dosing experimental design.

TABLE 11A

Nalmefene Film Formulations Studied in Beagle Dogs

| Test Article | Storage | Correction Factor |
| --- | --- | --- |
| Nalmefene Buccal Film F1 | Ambient | None |
| Nalmefene Buccal Film F2 | Ambient | None |
| Nalmefene Buccal Film F3 | Ambient | None |
| Nalmefene (for IV route) | 2-8° C. | None |

Nalmefene IV and exemplary buccal film doses were administered on a fixed-dose basis with a design target dose of 4 mg/animal. Due to filtration processes typically used in the manufacturing of sterile products, the actual dose strength of the IV was 3.67 mg per 4 mL injection. Similarly the film products for Formulations F1, F2 and F3 were 4.25, 4.5 and 4.4 mg, respectively.

Animals were fasted overnight through approximately 2 hours post dose for all phases. Feed was returned after collection of the 2-hour blood sample collection.

The IV dose was administered by bolus injection into a cephalic vein at a fixed volume of 4 mL/animal. After dose administration, but before the needle was removed from the animal, the dosing apparatus was flushed with approximately 2 mL of saline. IV dose sites were marked and maintained throughout the study phase.

For buccal film administration, animals were anesthetized by IV co-injection of midazolam (0.2 mg/kg) and dexmedetomidine (0.02 mg/kg) administered in the same syringe. The buccal film was applied to the cleaned, moistened buccal (mucosal) surface, briefly held in place, and examined. Upon completion of dosing (approximately 40 to 45

TABLE 11B

Dosing Experimental Design

| Animal | Group | Sex | Body Weight (kg) | Dose Route | Formulation | Actual Dose Concentration (mg/buccal film) | Target Dose Level (mg/animal) | Actual Dose Amount (film/animal) | Calculated Dose Administered (mg/animal) | (mg/kg) |
| --- | --- | --- | --- | --- | --- | --- | --- | --- | --- | --- |
| | | | | | | Phase 1 | | | | |
| D001 | 1 | M | 10.2 | IV | IV | 0.9175[a] | 4 | 4[b] | 3.67 | 0.360 |
| D002 | 1 | M | 9.4 | IV | IV | 0.9175[a] | 4 | 4[b] | 3.67 | 0.390 |
| D401 | 1 | F | 8.1 | IV | IV | 0.9175[a] | 4 | 4[b] | 3.67 | 0.453 |
| D101 | 2 | M | 10.3 | Buccal | F1 | 4.25 | 4 | 1 | 4.25 | 0.413 |
| D501 | 2 | F | 8.7 | Buccal | F1 | 4.25 | 4 | 1 | 4.25 | 0.489 |
| D503 | 2 | F | 7.0 | Buccal | F1 | 4.25 | 4 | 1 | 4.25 | 0.607 |
| D201 | 3 | M | 9.1 | Buccal | F2 | 4.49 | 4 | 1 | 4.49 | 0.493 |
| D202 | 3 | M | 9.4 | Buccal | F2 | 4.49 | 4 | 1 | 4.49 | 0.478 |
| D601 | 3 | F | 8.0 | Buccal | F2 | 4.49 | 4 | 1 | 4.49 | 0.561 |
| D301 | 4 | M | 9.5 | Buccal | F3 | 4.39 | 4 | 1 | 4.39 | 0.462 |
| D701 | 4 | F | 8.3 | Buccal | F3 | 4.39 | 4 | 1 | 4.39 | 0.529 |
| D702 | 4 | F | 8.9 | Buccal | F3 | 4.39 | 4 | 1 | 4.39 | 0.493 |
| | | | | | | Phase 2 | | | | |
| D001 | 1 | M | 10.0 | Buccal | F1 | 4.25 | 4 | 1 | 4.25 | 0.425 |
| D002 | 1 | M | 9.5 | Buccal | F1 | 4.25 | 4 | 1 | 4.25 | 0.447 |
| D401 | 1 | F | 7.8 | Buccal | F1 | 4.25 | 4 | 1 | 4.25 | 0.545 |
| D101 | 2 | M | 10.4 | Buccal | F2 | 4.49 | 4 | 1 | 4.49 | 0.432 |
| D501 | 2 | F | 8.6 | Buccal | F2 | 4.49 | 4 | 1 | 4.49 | 0.522 |
| D503 | 2 | F | 7.2 | Buccal | F2 | 4.49 | 4 | 1 | 4.49 | 0.624 |
| D201 | 3 | M | 9.3 | Buccal | F3 | 4.39 | 4 | 1 | 4.39 | 0.472 |
| D202 | 3 | M | 9.7 | Buccal | F3 | 4.39 | 4 | 1 | 4.39 | 0.453 |
| D601 | 3 | F | 8.0 | Buccal | F3 | 4.39 | 4 | 1 | 4.39 | 0.549 |
| D301 | 4 | M | 9.5 | IV | IV | 0.9175[a] | 4 | 4[b] | 3.67 | 0.386 |
| D701 | 4 | F | 8.0 | IV | IV | 0.9175[a] | 4 | 4[b] | 3.67 | 0.459 |
| D702 | 4 | F | 8.8 | IV | IV | 0.9175[a] | 4 | 4[b] | 3.67 | 0.417 |
| | | | | | | Phase 3 | | | | |
| D001 | 1 | M | 9.9 | Buccal | Buccal | 4.49 | 4 | 1 | 4.49 | 0.454 |
| D002 | 1 | M | 9.6 | Buccal | Buccal | 4.49 | 4 | 1 | 4.49 | 0.468 |
| D401 | 1 | F | 7.8 | Buccal | Buccal | 4.39 | 4 | 1 | 4.39 | 0.576 |
| D101 | 2 | M | 10.5 | Buccal | Buccal | 4.39 | 4 | 1 | 4.39 | 0.418 |
| D501 | 2 | F | 8.6 | Buccal | Buccal | 4.39 | 4 | 1 | 4.39 | 0.510 |
| D503 | 2 | F | 7.1 | Buccal | Buccal | 4.49 | 4 | 1 | 4.39 | 0.618 |
| D201 | 3 | M | 9.6 | IV | IV | 0.9175[a] | 4 | 4[b] | 3.67 | 0.382 |
| D202 | 3 | M | 9.9 | IV | IV | 0.9175[a] | 4 | 4[b] | 3.67 | 0.371 |
| D601 | 3 | F | 8.0 | IV | IV | 0.9175[a] | 4 | 4[b] | 3.67 | 0.459 |
| D301 | 4 | M | 9.5 | Buccal | Buccal | 4.25 | 4 | 1 | 4.25 | 0.447 |
| D701 | 4 | F | 8.0 | Buccal | Buccal | 4.25 | 4 | 1 | 4.25 | 0.531 |
| D702 | 4 | F | 9.0 | Buccal | Buccal | 4.25 | 4 | 1 | 4.25 | 0.472 | minutes post dose), the buccal surface was again examined and observations were recorded. For each phase of buccal dose administration, it was observed that a blue residue (consistent with the color of the formulation disc) remained at the dose site for each animal.

Blood (approximately 1 mL) was collected from each animal from a jugular or cephalic vein (not used for dosing, as applicable, with the following exception) into tubes containing $K_2$EDTA predose and at approximately 0.0417, 0.083, 0.167, 0.25, 0.5, 1, 2, 4, 8, 12, and 24 hours post dose. Post dose collection times were based on the time of buccal film placement, as applicable.

Blood was maintained in chilled cryogenic racks before centrifugation to obtain plasma. Centrifugation began within 1 hour of collection. Plasma was placed into 96-well tubes with barcode labels and maintained on dry ice before storage at approximately −70° C.

Calculations were performed using Microsoft Excel Version 14.0. Statistical analyses were limited to descriptive statistics such as mean and standard deviation, if applicable.

Noncompartmental analysis was applied to the individual plasma nalmefene concentration data for male and female dogs. The following parameters were estimated whenever possible:

The majority of nornalmefene concentrations were below the limit of quantitation; therefore, no pharmacokinetic analysis was conducted on the nornalmefene results.

| Parameters | Definition |
|---|---|
| $C_0$ | Back-extrapolated concentration at time 0 (IV bolus only). |
| $C_{max}$ | Maximum observed concentration. |
| $T_{max}$ | Time of maximum observed concentration. |
| $C_{first}$ | First observed concentration. |
| $T_{first}$ | Time of first observed concentration. |
| $AUC_{0-t}$ | Area under the concentration-time curve from hour 0 to the last measurable concentration, estimated by the linear trapezoidal rule. |
| $AUC_{0-24}$ | Area under the concentration-time curve from hour 0 to hour 24, estimated by the linear trapezoidal rule. |
| $AUC_{0-inf}$ | Area under the concentration-time curve from hour 0 to infinity, and calculated as follows: $AUC_{0-inf} = AUC_{0-t} + Ct/\lambda_z$ Where $C_t$ is the last measurable concentration and $\lambda_z$ is the elimination rate constant estimated using log-linear regression during the terminal elimination phase. The number of points used in $\lambda_z$ calculation was determined by visual inspection of the data describing the terminal phase. At least the last three time points with measurable values were used in $\lambda_z$ calculation. |
| $t_{1/2}$ | Elimination half-life, determined by $\ln(2)/\lambda_z$. |
| CL | Clearance, calculated as Dose/$AUC_{0-inf}$ (IV bolus dose only). |
| CL/F | Apparent clearance, calculated as Dose/$AUC_{0-inf}$ (extravascular doses). |
| $V_{ss}$ | Volume of distribution at steady-state, calculated as CL * $MRT_{0-inf}$ (IV bolus dose only). |
| VZ/F | Apparent volume of distribution during the terminal phase, calculated as CL/$\lambda_z$ (extravascular doses). |
| $DNC_{max}$ | Dose normalized $C_{max}$, calculated as $C_{max}$/dose level. |
| $DNAUC_{0-24}$ | Dose normalized $AUC_{0-24}$, calculated as $AUC_{0-24}$/dose level. |

Formulation and bioavailability comparison, calculated as:

([$C_{max}$ or $AUC_{0-24}$F1,F2, or F3buccal]/[$C_{max}$ or $AUC_{0-24}$F1, or F2buccal or IV bolus]).

Actual doses based on body weight on the day of dosing were used in the calculation of all PK parameters. Nominal sampling times were used, except where deviations were noted. Concentration values below the lower limit of quantitation (<0.1 ng/mL) were treated as zero for descriptive statistics and pharmacokinetic analysis. Embedded zeros were excluded from the pharmacokinetic analysis. Predose concentrations were excluded to allow for back extrapolation for IV bolus administration.

Figure 16:
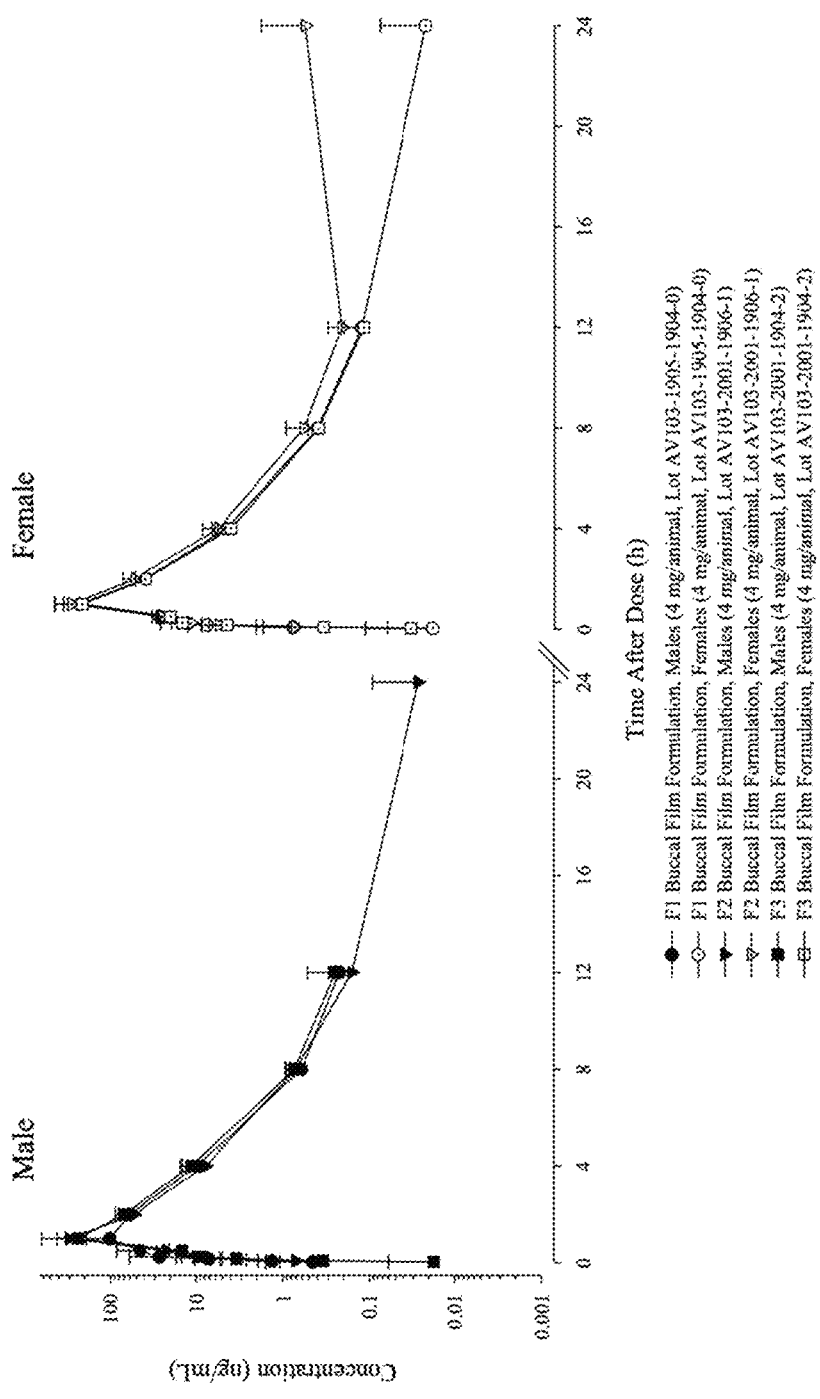
FIG. 16 is a chart of mean concentration-time profiles of nalmefene in dog plasma for male species in Example 12.
Figure 17:
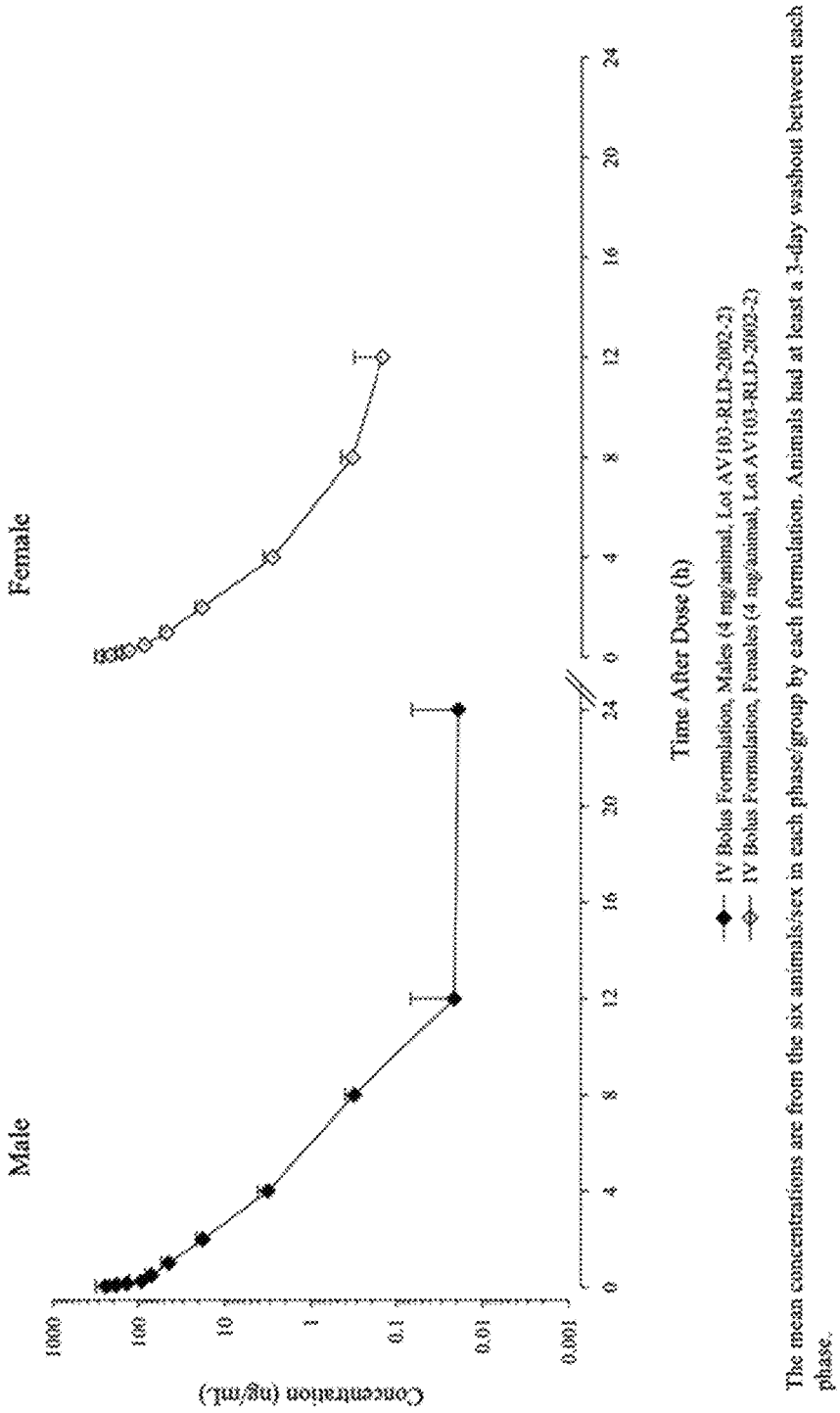
FIG. 17 is a chart of mean concentration-time profiles of nalmefene in dog plasma for female species in Example 12.

The mean concentration-time profiles of nalmefene in dog plasma separated for male and female species are presented graphically in FIG. 16 and FIG. 17 for the buccal films and intravenous routes of administration.

The mean concentration-time profiles for males and females were similar. In general, sex differences in nalmefene mean $C_{max}$ and $AUC_{0-24}$ values were less than 2-fold. Exposure, as assessed by nalmefene mean $C_{max}$ and $AUC_{0-24}$ values, were similar between all F1, F2, and F3 buccal film formulation administrations and the IV bolus administration. Bioavailability between the buccal film administrations was significant.

In IV dose, males appeared to have a slightly faster elimination than females as represented by the 12-hour timepoint. However, this may have resulted from standard error closer to the lower limits of quantification (LLOQ). Results also show that the majority of nornalmefene concentrations were below the limit of quantitation; therefore, no pharmacokinetic analysis was conducted on the nornalmefene results.

Figure 18:
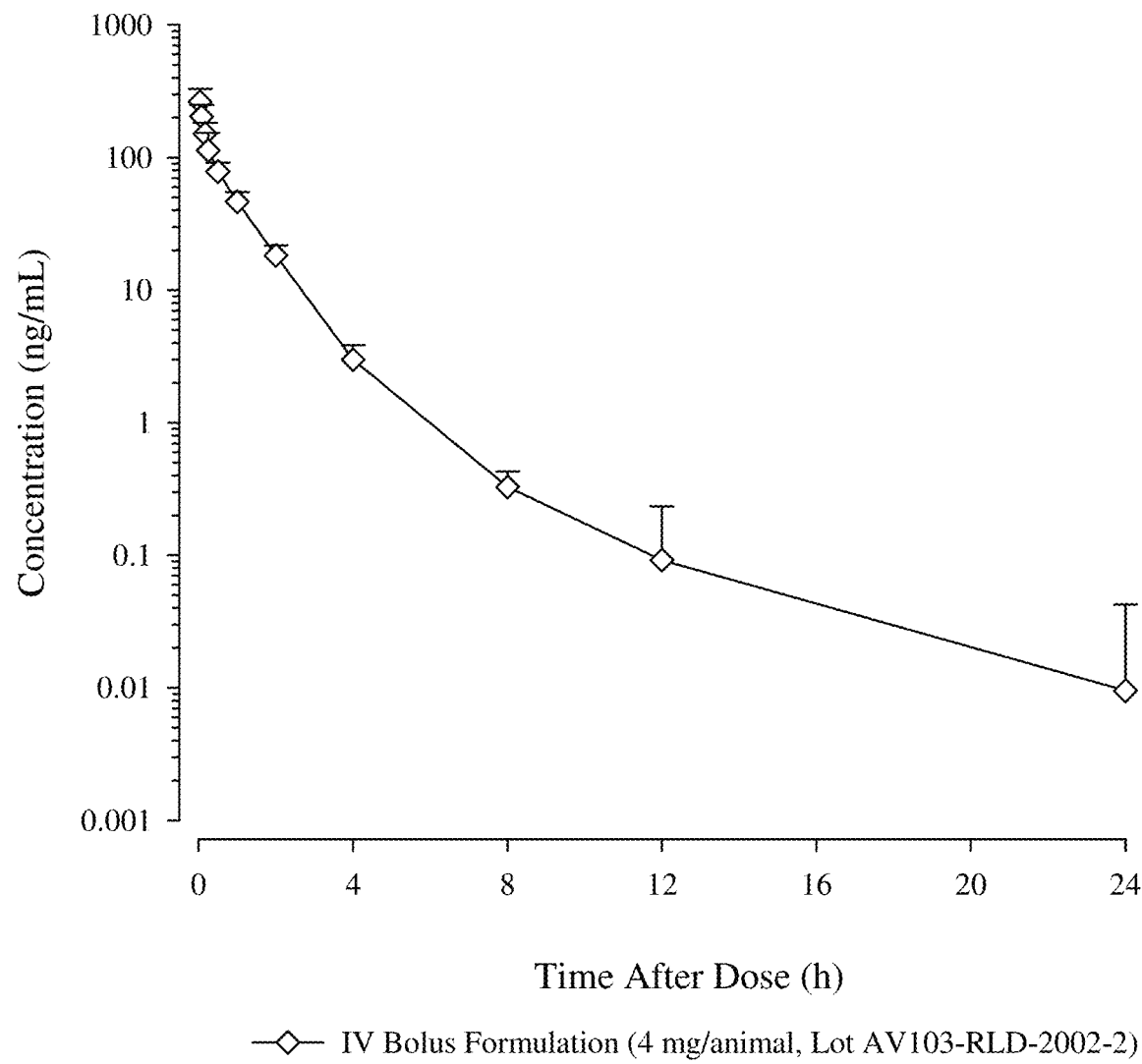
FIG. 18 is a graph showing the mean (+SD) concentrations (ng/mL) of nalmefene in combined male and female dog plasma following Nalmefene IV dose administration.
Figure 19:
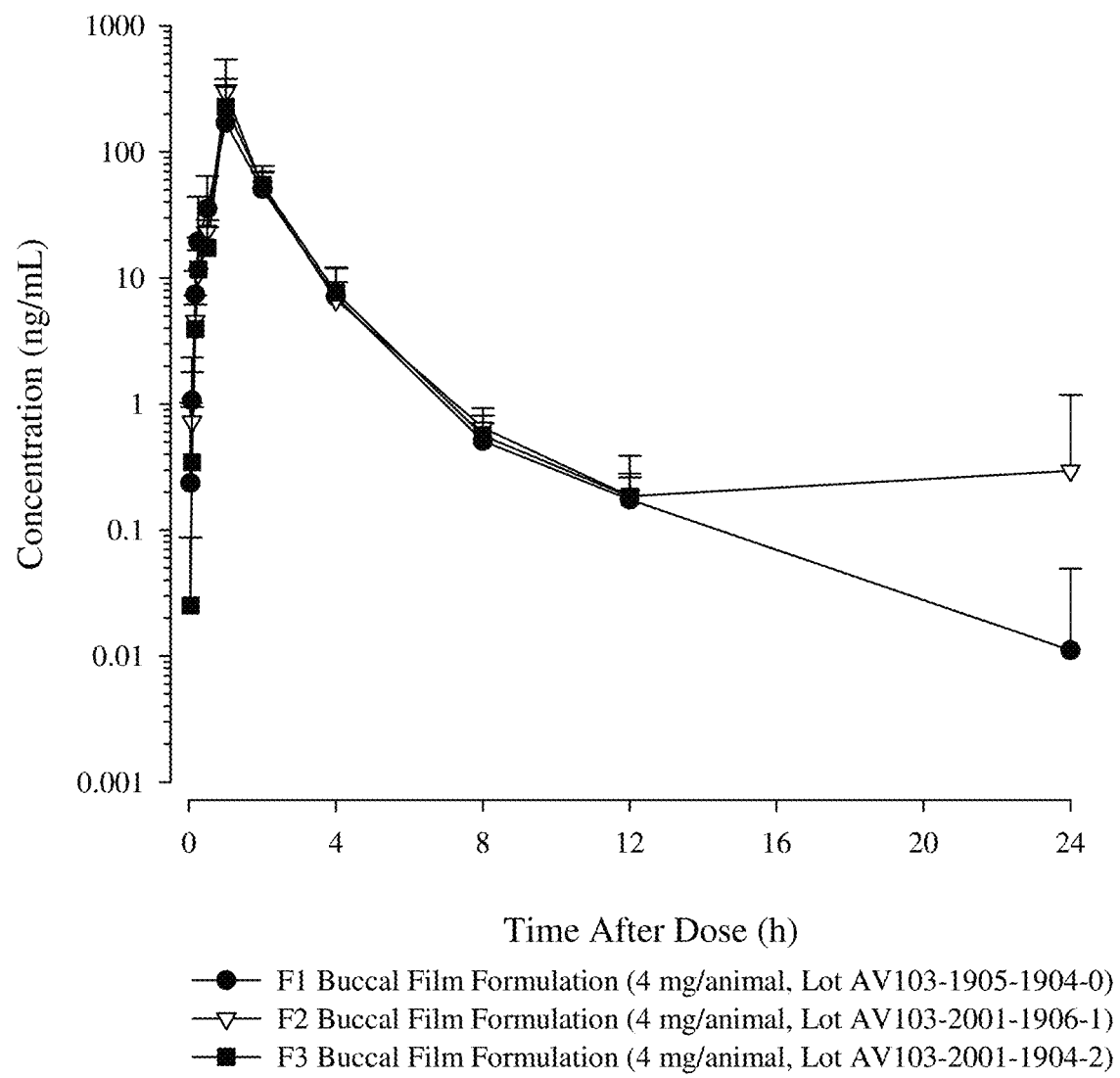
FIG. 19 is a graph showing the mean (+SD) concentrations (ng/mL) of Nalmefene in combined male and female dog plasma following buccal film formulation administrations.

FIGS. 18 and 19 are graphs showing combined results for the male and female groups. FIG. 18 presents the mean (+SD) concentrations (ng/mL) of nalmefene in combined male and female dog plasma following Nalmefene IV dose administration. FIG. 19 presents mean (+SD) concentrations (ng/mL) of Nalmefene in combined male and female dog plasma following buccal film formulation administrations. The formulations appear consistent and similar with minor differences in the onset of speed. The $T_{max}$ for each of the formulations remains at 1 h. F2 formulation had an anomalous result at 24 h which is deemed inconsequential since it is below the 1 ng/ml to provide therapeutic action.

The 24-hour mean nalmefene concentration for the F2 (buccal) formulation was higher than the preceding mean concentrations and was due to the higher than expected concentration for Animal D0503. There was no reason to exclude this sample value. However, it does appear to be anomalous, as this trend was not observed in any other animal.

The single-dose exposure measured over 12-hours for formulations F1, F2, and F3 buccal film formulations were marginally different across the single dose. After F1, F2, and F3 buccal film formulation administrations, nalmefene was absorbed, with median $T_{max}$ values of 1.00 hour. After reaching $C_{max}$, nalmefene concentrations declined, with mean half-life ($t_{1/2}$) values of 1.51, 1.47, and 1.34 hours after F1, F2, and F3 buccal film formulation administrations, respectively. Mean concentration values for nalmefene were generally measurable through 12 hours postdose. The mean CL/F values ranged from 1800 to 2420 mL/hr/kg and the mean $V_Z$/F values ranged from 3660 to 5230 mL/kg. After IV bolus administration, nalmefene concentrations readily declined generally in a biexponential manner, with the mean $t_{1/2}$ value of 1.34 hours. Mean concentration values for nalmefene were generally measurable through 12 hours postdose. The mean CL value was 2770 mL/hr/kg and the mean $V_{SS}$ value was 2770 mL/kg.

All animals appeared healthy before dosing and throughout the testing. No irritation of the buccal mucosa was observed after a single buccal dose of the film formulations.

Figure 20:
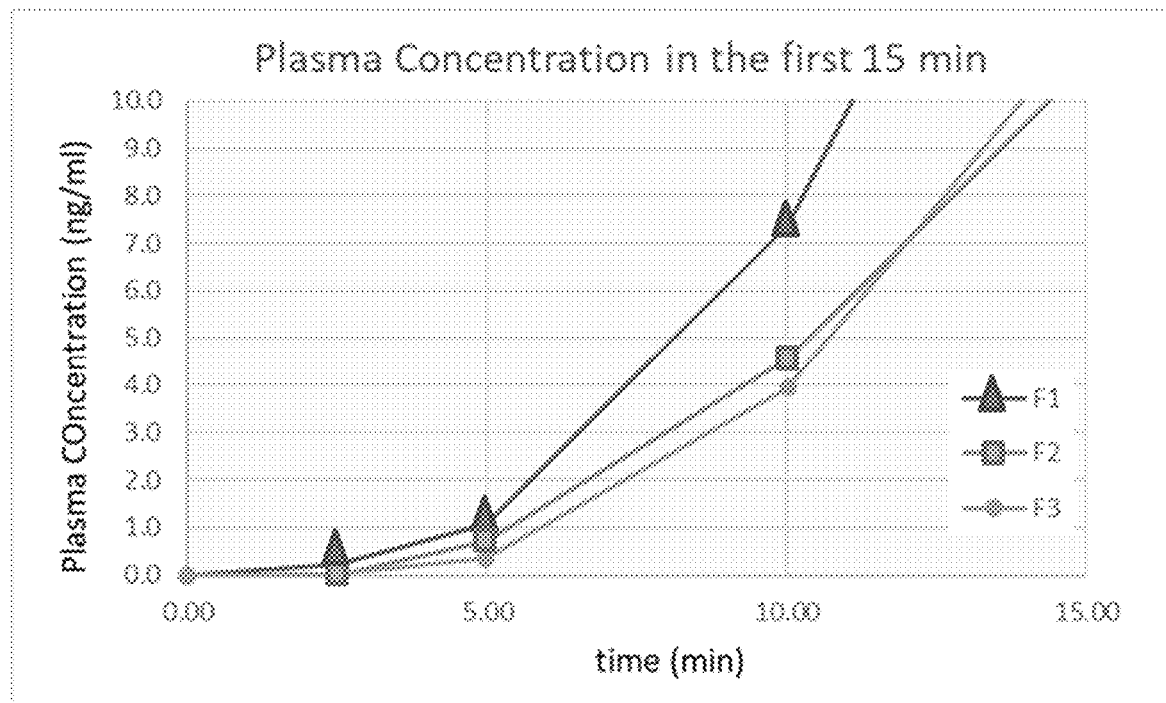
FIG. 20 is a chart showing the mean plasma concentration of three formulations for N=12 dogs (6M/6F) in the first 15 minutes post-dose exposure.
Figure 21:
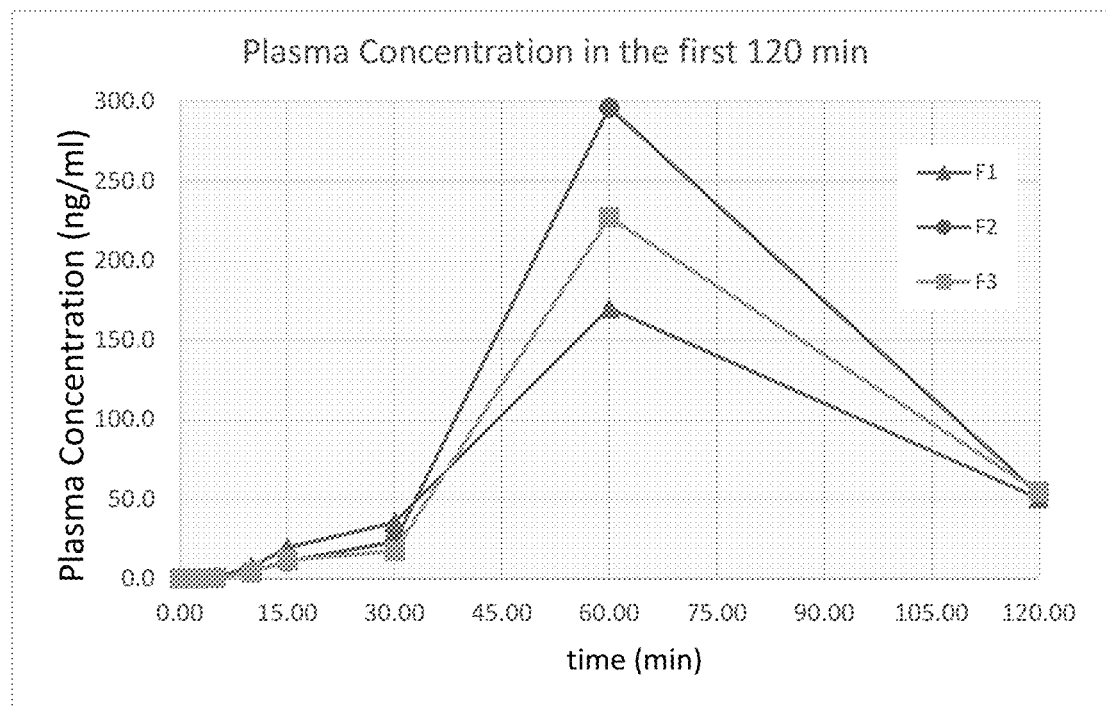
FIG. 21 is a chart showing the mean plasma concentration of three formulations for N=12 dogs (6M/6F) 2 hours post-dose exposure.

FIG. 20 and FIG. 21 show the mean plasma concentration of the three formulations for N=12 dog (6M/6F) in the first 15 minutes and 2 hours post-dose exposure. As can be seen, the plasma concentration increased faster when Formulation 1 was administered in comparison to administration of Formulation 2 or 3. Film formulation 1 reached a mean plasma level of 7.39 ng/mL at the 10 min time point. Film formulation 2 reached a mean plasma level of 4.58 ng/mL at the 10 min time point, and film formulation 3 reached a mean plasma level of 3.94 ng/mL at the 10 min time point. Additionally, formulation 1 had a lower $C_{max}$ which suggests a better safety profile by reducing the risk of precipitated withdrawal compared to the other two formulations.

The results of the experiments indicate that the exemplary buccal films offer a viable solution as a medical-counter measure and a treatment solution for the reversal of opioid-induced respiratory depression.

All three formulations showed excellent bioavailability in comparison to the IV dose. Notably, the time required to reach a plasma concentration greater than 1 ng/mL was less than 10 min for each buccal film. Film formulation 1 reached a mean plasma level of 7.39 ng/mL at the 10 min time point. Film formulation 2 reached a mean plasma level of 4.58 ng/mL at the 10 min time point. Finally, film formulation 3 reached a mean plasma level of 3.94 ng/mL at the 10 min time point. Furthermore, the rescue levels of nalmefene were maintained for at least 4 hr for each formulation and only dropped below 1 ng/mL between the 4 and 8 hr collection times.

Formulation 1 had a plasma concentration of greater than 5 ng/mL within 10 minutes. This result is significant in ensuring the reversal of opioid-induced respiratory depression in less than 10 minutes. Formulation 1 demonstrated the highest blood level of 1.07 ng/mL at 5 min post-administration, compared to concentrations of 0.726 and 0.346 ng/mL for films 2 and 3 at 5 min, respectively. Formulation 1 also provided a relatively lower $C_{max}$. The $T_{max}$ for all buccal formulation was 1 h.

Table 12 provides a summary of pharmacokinetic parameters. The mean $T_{first}$ for each of the Formulations F1, F2 and F3 are shown in Table 12.

TABLE 12

Pharmacokinetic Parameters

| Dose Level (mg/animal) | Formulation | | $C_0$ (ng/mL) | $C_{first}$ (ng/mL) | $T_{first}$ (h) | $C_{max}$ (ng/mL) | DN $C_{max}$ [(ng/mL)/(mg/animal)] | $T_{max}$ (h) | $AUC_{0-t}$ (h*ng/mL) | $AUC_{0-24}$ (h*ng/mL) |
|---|---|---|---|---|---|---|---|---|---|---|
| 4 | F1 (buccal) | Mean | NA | 1.52 | 0.0901 | 175 | 359 | 1.04 | 240 | 241 |
| | | SD | NA | 1.41 | 0.0392 | 167 | 336 | 0.334 | 122 | 122 |
| | | CV % | NA | 93.3 | 43.5 | 95.2 | 93.6 | 32.1 | 50.8 | 50.5 |
| | | Median | NA | 1.23 | 0.0830 | 94.3 | 193 | 1.00 | 214 | 215 |
| | | Min | NA | 0.110 | 0.0417 | 45.6 | 102 | 0.500 | 108 | 109 |
| | | Max | NA | 3.82 | 0.167 | 590 | 1250 | 2.00 | 476 | 477 |
| | | N | 0 | 12 | 12 | 12 | 12 | 12 | 12 | 12 |
| 4 | F2 (buccal) | Mean | NA | 1.77 | 0.118 | 298 | 578 | 1.17 | 336 | 337 |
| | | SD | NA | 1.17 | 0.0433 | 244 | 490 | 0.389 | 190 | 189 |
| | | CV % | NA | 66.2 | 36.7 | 82.1 | 84.7 | 33.4 | 56.4 | 56.2 |
| | | Median | NA | 1.80 | 0.0830 | 179 | 336 | 1.00 | 255 | 256 |
| | | Min | NA | 0.122 | 0.0830 | 55.2 | 118 | 1.00 | 140 | 141 |
| | | Max | NA | 3.73 | 0.167 | 728 | 1490 | 2.00 | 685 | 685 |
| | | N | 0 | 12 | 12 | 12 | 12 | 12 | 12 | 12 |
| 4 | F3 (buccal) | Mean | NA | 2.03 | 0.125 | 228 | 466 | 1.08 | 287 | 288 |
| | | SD | NA | 1.61 | 0.0535 | 153 | 328 | 0.289 | 135 | 135 |
| | | CV % | NA | 79.1 | 42.8 | 67.2 | 70.3 | 26.6 | 47.0 | 46.8 |
| | | Median | NA | 1.99 | 0.167 | 189 | 361 | 1.00 | 246 | 249 |
| | | Min | NA | 0.105 | 0.0417 | 63.4 | 134 | 1.00 | 149 | 150 |
| | | Max | NA | 5.92 | 0.167 | 507 | 1070 | 2.00 | 514 | 514 |
| | | N | 0 | 12 | 12 | 12 | 12 | 12 | 12 | 12 |
| 4 | IV | Mean | 244 | 263 | 0.0417 | 263 | 640 | 0.0417 | 162 | 163 |
| | | SD | 178 | 66.2 | 0.00 | 66.2 | 169 | 0.00 | 26.0 | 26.0 |
| | | CV % | 73.0 | 25.1 | 0.00 | 25.1 | 26.4 | 0.00 | 16.0 | 15.9 |
| | | Median | 275 | 255 | 0.0417 | 255 | 601 | 0.0417 | 164 | 165 |
| | | Min | 0.00 | 146 | 0.0417 | 146 | 374 | 0.0417 | 106 | 106 |
| | | Max | 490 | 377 | 0.0417 | 377 | 945 | 0.0417 | 208 | 209 |
| | | N | 12 | 12 | 12 | 12 | 12 | 12 | 12 | 12 |

| Dose Level (mg/animal) | Formulation | | DN $AUC_{0-24}$ [(h*ng/mL)/(mg/animal)] | $AUC_{0-inf}$ (h*ng/mL) | $t_{1/2}$ (h) | CL/F (mL/h/kg) | Vz/F (mL/kg) |
|---|---|---|---|---|---|---|---|
| 4 | F1 (buccal) | Mean | 504 | 223 | 1.51 | 2570 | 5560 |
| | | SD | 244 | 111 | 0.272 | 1200 | 2880 |
| | | CV % | 48.5 | 49.9 | 17.9 | 46.8 | 51.8 |
| | | Median | 470 | 197 | 1.51 | 2160 | 4460 |
| | | Min | 205 | 109 | 0.990 | 991 | 2320 |
| | | Max | 1010 | 476 | 2.14 | 4880 | 12300 |
| | | N | 12 | 11 | 11 | 11 | 11 |
| 4 | F2 (buccal) | Mean | 658 | 292 | 1.47 | 2020 | 4300 |
| | | SD | 380 | 159 | 0.119 | 726 | 1610 |
| | | CV % | 57.7 | 54.3 | 8.07 | 36.0 | 37.3 |
| | | Median | 518 | 232 | 1.50 | 2060 | 4760 |
| | | Min | 302 | 176 | 1.33 | 799 | 1590 |
| | | Max | 1450 | 617 | 1.60 | 3000 | 6510 |
| | | N | 12 | 7 | 7 | 7 | 7 |

TABLE 12-continued

| | | Pharmacokinetic Parameters | | | | | |
|---|---|---|---|---|---|---|---|
| 4 | F3 | Mean | 594 | 287 | 1.34 | 2120 | 4010 |
| | (buccal) | SD | 303 | 135 | 0.252 | 993 | 1940 |
| | | CV % | 51.1 | 47.0 | 18.9 | 46.9 | 48.3 |
| | | Median | 524 | 247 | 1.35 | 1930 | 3710 |
| | | Min | 266 | 149 | 0.929 | 899 | 1520 |
| | | Max | 1110 | 514 | 1.82 | 3770 | 7430 |
| | | N | 12 | 12 | 12 | 12 | 12 |
| 4 | IV | Mean | 397 | 166 | 1.34 | 2540 | 2540 |
| | | SD | 63.9 | 27.4 | 0.383 | 467 | 407 |
| | | CV % | 16.1 | 16.5 | 28.5 | 18.4 | 16.0 |
| | | Median | 398 | 166 | 1.14 | 2520 | 2480 |
| | | Min | 273 | 106 | 1.01 | 2020 | 2000 |
| | | Max | 495 | 209 | 2.06 | 3670 | 3390 |
| | | N | 12 | 10 | 10 | 10 | 10 | h Hours.
NA Not applicable.
Note:
The mean parameters are from the six animals/sex in each phase/group by each formulation. Animals had at least a 3-day washout between each phase.

That which is claimed is:

1. A single layer transmucosal delivery device comprising:
a polymer film comprising a polymer matrix, and
a pharmaceutical composition disposed on a surface of the polymer film, wherein the pharmaceutical composition is not a self-supporting layer and is not present in a self-supporting layer, the pharmaceutical composition comprising at least one pharmaceutical active, wherein the at least one pharmaceutical active comprises nalmefene or a salt thereof, a binding polymer, a surfactant, a solubilizing solvent, and an anti-crystallization agent, wherein a content of the nalmefene in the composition is about 1 to 25% w/w and the composition has a pH in a range of about 4 to about 8, and
wherein the delivery device exhibits a residence time in the mouth of a subject ranging from about 5 minutes to about 15 minutes and is substantially mucoadhesive to a mucosal surface when placed sublingually under the tongue or placed buccally at the inner lining of the cheek of the subject.

2. The single layer transmucosal delivery device of claim 1, further comprising an additional pharmaceutical active wherein the additional pharmaceutical active comprises a compound selected from one or more of Benazepril, Captopril, Enalapril, Lisinopril, Moxepril, Perindopril, Quinapril, Ramipril Trandolapril, buprenorphine, disulfiram, naltrexone, cannabidiol, nalfurafine, naltrexone, varenicline, alfuzosin, doxazosin, prazosin, tamsulosin, terazosin, riluzole, donepezil, galantamine, rivastigmine, memantine, allopurinol, azelastine, beclomethasone, budesonide, desmopressin, fluticasone, phenylephrine, barbiturates, metronidazole, carbamazepine, cimetidine, ibuprofen, penicillins, amoxicillin, cloxacillin, dicloxacillin, ticarcillin, phenyloin, quinidine, streptomycin, vancomycin, ketamine, pentozocine, propofol, buprenorphine, oxycodone, hydrocodone, nalbuphine; amlexanox, benzocaine, carbamide, peroxide, nystatin, lidocaine, pilocarpine, candesartan, eprosartan mesylate, olmesartan, telmisartin, valsartan, adenosine, amiodarone, atropine, epinephrine, mexiletine, moricizine, procainamide, propafenone, quinidine, sotalol, verapamil, hyoscyamine, scopolamine, darifenacin, oxybutynin, solifenacin, tolterodine, glycopyrrolate, hyoscyamine, oxybutynin, propantheline, scopolamine, promethazine, flavoxate, trospium, tolterodine, carbamazepine, clonazepam, diazepam, ethosuximide, felbamate, pregabalin, levetiracetam, lamotrigine, lorazepam, midazolam, oxcarbazepine, phenobarbital, tiagabine, topiramate, valproic acid, asenapine, buproprion, buprenorphine, citalopram, desipramine, doxepin, duloxetine, escitalopram, fluoxetine, fluvoxamine, imipramine, mirtazapine, nefazodone, nortriptyline, nortriptyline, sertraline, trazodone, venlafaxine, diphenoxylate, atropine, loparimide, bismuth subsalicylate, acarbose, miglitol, metformin, rosiglitazone maleate and metformin hydrochloride, glucovance, metaglip, metaglip, rosiglitazone, osiglitazone, repaglinide, chlorpropamide, glimepiride, glyburide, glipizide, tolazamide, tolbutamide, glucagon, extenatide, and/or pramlintide, adalimumab, anakinra, alitretinoin, becaplermin, calamine, doxepin, fluorouracil, masoprocol, pimecrolimus, tacrolimus, auranofin, azathioprine, etanercept, hydroxychloroquine, infliximab, leflunomide, methotrexate, sulfasalazine, aprepitant, dolasetron, droperidol, granisetron, metoclopramide, ondansetron, prochlorperazine, scopolamine, promethazine, trimethobenzamide, amphotericin B, anidulafungin, caspofungin, clotrimazole fluconazole, flucytosine, griseofulvin, itraconazole, ketoconazole, micafungin, nystatin, posaconazole, terbinafine, voriconazole, butenafine, ciclopirox, clotrimazole, econazole, ketoconazole, miconazole, naftifine, nystatin, oxiconazole terbinafine, butenafine, ciclopirox, clotrimazole, econazole, ketoconazole, miconazole, naftifine, nystatin, oxiconazole, terbinafine clindamycin, metronidazole, butoconazole, clotrimazole, miconazole, terconazole, tioconazole, tolnaftate, adefovir, entecavir, lamivudine, peginterferon alfa-2a, peginterferon alfa-2b, rebetron, ribavirin, acyclovir, famciclovir, valacyclovir, acyclovir, docosanol, penciclovir, cetirizine, desloratadine, fexofenadine, loratadine, chlorpheniramine, clemastine, cyproheptadine, dimenhydrinate, diphenhydramine, hydroxyzine, benazepril, captopril, enalapril, lisinopril, moexipril, losartan, valsartan, atenolol, chlorthalidone, bisoprolol, metoprolol, nadolol, bendroflumethazide, propranolol, timolol, amlodipine, benazepril, verapamil, trandolapril, amiloride, spironolactone, triamterene, clonidine, hydralazine, methyldopa, prazosin, polythiazide, aliskiren, aliskiren, epoprostenol, fenoldopam, hydralazine, minoxidil, nitroprusside, phentolamine, treprostinil, oseltamivir phosphate, rimantadine, zanamivir, atovaquone, chloroquine, Iodoquinol, mefloquine, primaquine, pyrimethamine, pyrimethamine, pyruvium, sulfadoxine, quinine, abciximab, dipyridamole/ ASA, anagrelide, cilostazol, clopidogrel, dipyridamole, eptifabatide, ticlopidine, tirofiban, aripiprazole, chlorpromazine, clozapine, fluphenazine, haloperidol, loxapine, molindone, amantadine, rimantadine, and memantine, olanzepine, perphenazine, pimozide, quetiapine, risperidone, thioridazine, thiothixine, trifluoperazine, ziprasidone, and/or lithium, dicyclomine, donnatal extentabs, propantheline, simethicone, hyoscyamine, Librax, tegaserod, baclofen, carisprodol, cyclobenzaprine, cyclobenzaprine, diazepam, metaxalone, orphenadrine, and/or bellergal-S, acyclovir, famciclovir, valacyclovir, docosanol, and/or penciclovir, captopril, clonidine, enalaprilat, esmolol, fenoldopam mesylate, hydralazine, labetalol, nicardipine, and/or nitroglycerin, benzonatate and/or guaifenesin, pimecrolimus and/or tacrolimus, benzodiazepines and non-benzodiazepine sedatives like alprazolam, buspirone, chlordiazepoxide, chlorazepate, clonazepam, diazepam, estazolam, eszcpiclone, flurazepam, lorazepam, midazolam, oxazepam, ramelteon, temazepam, triazolam, zaleplon and zolpidem; beta blockers, such as atenolol, betaxolol, bisoprolol, carvedilol, esmolol, labetalol, metoprolol, nadolol, pindolol, propranolol, sotalol, and/or timolol cholestyramine, colesevelam, and/or colestipol, alendronate, etidronate, pamidronate, risedronate, tiludronate and zoledronic acid, raloxifene, and/or teriparatide, alfuzosin, doxazosin, dutasteride, finasteride, tamsulosin, and/or terazosin, amlodipine, bepridil, diltiazem, felodipine, isradipine, nicardipine, nifedipine, and/or nisoldipine, cefadroxil, cefazolin, cephradine, cephalexin, cefaclor, cefotetan, cefoxitin, cefprozil, cefuroxime, cefuroxime, loracarbef, cefdinir, cefixime, cefoperazone, cefotaxime, cefpodoxime, ceftazidime, ceftibuten, ceftizoxime, and/or cefepime, darbepoietin alfa, erythropoietin, filgrastim, oprelvekin, pegfilgrastim, and/or sargramostim, budesonide, cortisone acetate, dexamethasone, fludrocortisones, hydrocortisone, methylprednisolone and prednisone, aclometasone diproprionate, desonide, flucinolone acetonide, Hydrocortisone, betamethasone dipropionate, betamethasone valerate, clocortolone pivalate, desoximetasone, fluocinolone acetonide, flurandrenolide, fluticasone propionate, chydrocortisone butyrate, hydrocortisone valerate, mometasone furoate, prednicarbate, triamcinolone, amcinonide, augmented betamethasone dipropionate, betamethasone dipropionate, desoximetasone, diflorasone diacetate, fluocinolone acetonide, fluocinonide, halcinonide, clobetasol propionate, diflorasone diacetate and halobetasol propionate, and/or triamcinolone acetonide, phenylephrine and/or pseudoephedrine, acetazolamide, amiloride, amiloride and HCTZ bendroflumethiazide, bumetanide, chlorothiazide, chlorthalidone, dichlorphenamide, eplenerone, ethacrynic acid, furosemide, hydrochlorothiazide, HCTZ/triampterene, hydroflumethiazide, indapamide, methazolamide, methyclothiazide, methyclothiazide, metolazone, polythiazide, spironolactone, spironolactone, HCTZ torsemide, trichlormethiazide, and/or triamterene, bromoc cinacalcet cosyntropin, riptine, cabergoline, calcitonin, desmopressin, Leuprolide, octreotide, and/or vasopressin, sildenafil, tadalafil, and/or vardenafil, clofibrate, fenofibrate, and/or gemfibrozil, ciprofloxacin, gatifloxacin, levofloxacin, moxifloxacin, norfloxacin, and/or ofloxacin, alosetron, infliximab, mesalamine, misoprostol, neomycin, octreotidev, osalazine, orlistat, sucralafate, vasopressinallopurinol, colchicine, probenecid, cimetidine, famotidine, nizatidine, ranitidine, balsalazide, budesonide, infliximab, mesalamine, olsalazine, and/or sulfasalazine, Interferon alfa-2A, Interferon alfa-2b, Interferon alfa-2b and ribavirin combo pack, Interferon alfa-N3, Interferon beta-1A, Interferon beta-1B, cilostazol, and/or pentoxifylline, Comvax, diphtheria-tetanus toxoid, hepatitis A vaccine, hepatitis B vaccine, influenza vaccine, Fluzone, lyme disease vaccine, and/or Pneumococcal Vaccine Polyvalent, dalteparin, danaparoid, enoxaparin, tinzaparin, and/or fondaparinux, azithromycin, clarithromycin, and/or erythromycin, almotriptan, eletriptan, frovatriptan, naratriptan, rizatriptan, sumatriptan, zolmitriptan, and/or dihydroergotamine, atracurium, cisatracurium, doxacurium, mivacurium, pancuronium, rocuronium, succinylcholine, vecuronium, mivacurium, rapacuronium, rocuronium, succinylcholine, atracurium, cisatracurium, pancuronium, vecuronium, doxacurium, pipecuronium, and/or tubocurarine, isosorbide dinitrate, isosorbide mononitrate, and/or nitroglycerin, arthrotec, diclofenac, etodolac, indomethacin, ketorolac, sulindac, tolmentin, diflunisal salsalate meloxicam, piroxicam, nabumetone flurbiprofen, ibuprofen, ketoprofen, naproxen, oxaprozin, celecoxib, rofecoxib, and/or valdecoxib, codeine, hydrocodone, hydromorphone, meperidine methadone, morphine, oxycodone, propoxyphene, tramadol, paracetomol, buprenorphine, butorphanol, nalbuphine, pentazocine, nalmefene, naloxone, ziconotide meperidine, and/or morphine, amantadine, benztropine, bromocriptine, entacapone, pergolide, pramipexole, ropinirole, selegiline, carbidopa and levodopa, tolcapone, and/or trihexyphenidyl, esomeprazole, lansoprazole, omeprazole, pantoprazole, and/or rabeprazole sodium, acitretin, alefacept, anthralin, calcipotriene, efalizumab, and/or tazarotene, ipratropium, tiotropium, albuterol, bitolterol, levalbuterol, pirbuterol, metaproterenol, formoterol, salmeterol, fluticasone/salmeterol, budesonide/formoterol, beclomethasone, budesonide, flunisolide, fluticasone, Mometasone furoate, triamcinolone, montelukast, zafirlukast, cromolyn sodium, nedocromil, acetylcysteine, and/or aminophylline/theophylline, atorvastatin, fluvastatin, lovastatin, pravastatin, rosuvastatin, simvastatin, and/or ezetimibe, atomoxetine, benzphetamine, caffeine, dexmethylphenidate, dextroamphetamine, diethylpropion, methylphenidate, modafinil, pemoline, phendimetrizine, phentermine and sibutramine, doxycycline, minocycline, and/or tetracycline, pentosan, bethanecol, and/or phenazopyridine, fenoldopam mesylate, hydralazine, nesiritide, nitroglycerin, dobutamine, dopamine, epinephrine, inaminone, milrinone, nicotine, norepinephrine, phenylephrine, and/or vasopressin.

3. The single layer transmucosal delivery device of claim 1, wherein the pharmaceutical composition is in the form of an amorphous or monocrystalline particle having a size less than 25 micrometers.

4. The single layer transmucosal delivery device of claim 1, wherein the surfactant comprises one or more components selected from the group consisting of sodium docusate USP, sodium lauryl sulfate, phospholipids, bile salts, ammonium glycyrrhizinate NF, copovidone, chitobiose, chitosan, n-dodecyl b-D maltoside, β-dodecyl maltoside, sucrose-6-monolaurin, polysorbate ethoxylated sorbitan-oleic acid ester, α-tocopheryl polyethylene glycol succinate, laureth-23, and polysorbate.

5. The single layer transmucosal delivery device of claim 1, wherein the solubilizing solvent comprises a component selected from the group consisting of ethanol NF, propylene glycol USP, glycerol USP, water and mixtures thereof.

6. The single layer transmucosal delivery device of claim 1, wherein the anti-crystallization agent comprises a component selected from the group consisting of sorbitol, mannitol, and xylitol.

7. The single layer transmucosal delivery device of claim 1, wherein the polymer film comprises one or more of sodium carboxymethylcellulose and hydroxypropyl methylcellulose.

8. The single layer transmucosal delivery device of claim 1, further comprising a pH adjusting agent, which is selected from the group consisting of one or more of phosphate, acetate, citrate, arginine, TRIS, and histidine buffers.

9. The single layer transmucosal delivery device of claim 8, wherein the pH of the pharmaceutical active composition at the surface is different than the pH of the polymer matrix that constitutes the film.

10. A method for treating or aiding in treating opioid overdose in a subject in need of such treatment, comprising transmucosally administering to the subject the transmucosal delivery device of claim 1, wherein the pharmaceutical active composition of the delivery device comprises nalmefene.

11. The method of claim 10, wherein the delivery device provides a mean plasma concentration of nalmefene of at least 1 ng/ml, within 10 minutes after administration.

12. A method of treating pruritus in a subject in need of such treatment, comprising transmucosally administering to the subject the transmucosal delivery device of claim 1, wherein the pharmaceutical active composition of the delivery device comprises nalmefene.

13. The method of claim 12, wherein the delivery device provides a mean plasma concentration of nalmefene of at least 1 ng/ml, within 10 minutes after administration.

14. A single layer transmucosal delivery device comprising:
a polymer film comprising a polymer matrix, and
a pharmaceutical composition comprising a taste masking agent and nalmefene or a salt thereof, wherein the composition is disposed on a surface of the polymer film in the form of a non-self-supporting domain, and wherein the pharmaceutical composition has a concentration of nalmefene such that upon administration of the composition to a subject, the subject has a mean plasma concentration of nalmefene of at least 1 ng/ml, within 30 minutes after administration,
wherein the delivery device exhibits a residence time in the mouth of a subject ranging from about 5 minutes to about 15 minutes and is substantially mucoadhesive to a mucosal surface when placed sublingually under the tongue or placed buccally at the inner lining of the cheek of the subject.

15. The single layer transmucosal delivery device of claim 14, wherein nalmefene or a salt thereof is the sole pharmaceutical active in the pharmaceutical composition.

16. The single layer transmucosal delivery device of claim 1, wherein nalmefene or a salt thereof is the sole pharmaceutical active in the pharmaceutical composition.

17. A single layer transmucosal delivery device comprising:
a polymer film comprising a polymer matrix, and
a pharmaceutical composition disposed directly on a surface of the polymer film, the composition comprising one pharmaceutical active, wherein the one pharmaceutical active is nalmefene or a salt thereof.

18. The single layer transmucosal delivery device of claim 1, wherein the pharmaceutical composition further comprises a buffering agent comprising ammonium glycyrrhizinate and dibasic sodium phosphate.

19. The single layer transmucosal delivery device of claim 18, wherein ammonium glycyrrhizinate and dibasic sodium phosphate are used as buffering agents for a pH range between 6.25 and 9.

* * * * *